US009115399B2

(12) United States Patent
Panigrahi et al.

(10) Patent No.: US 9,115,399 B2
(45) Date of Patent: Aug. 25, 2015

(54) RECOMBINATION SEQUENCE (RS) REARRANGEMENT FREQUENCY AS A MEASURE OF CENTRAL B CELL TOLERANCE

(75) Inventors: Anil K. Panigrahi, Philadelphia, PA (US); Eline Luning Prak, Malvern, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 884 days.

(21) Appl. No.: 13/120,324

(22) PCT Filed: Sep. 23, 2009

(86) PCT No.: PCT/US2009/058033
§ 371 (c)(1),
(2), (4) Date: Mar. 22, 2011

(87) PCT Pub. No.: WO2010/036706
PCT Pub. Date: Apr. 1, 2010

(65) Prior Publication Data
US 2011/0182902 A1 Jul. 28, 2011

Related U.S. Application Data

(60) Provisional application No. 61/099,392, filed on Sep. 23, 2008.

(51) Int. Cl.
*C12Q 1/68* (2006.01)
*C07H 21/04* (2006.01)

(52) U.S. Cl.
CPC ........ *C12Q 1/6883* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

2003/0228617 A1 12/2003 Aune et al.

OTHER PUBLICATIONS

Beishuizen et al. Heterogeneity in junctional regions of immunoglobulin kappa deleting element rearrangements in B cell leukemias: a new molecular target for detection of minimal residual disease. Leukemia 11:2200-2207 (1997).*

Carsetti et al., "Peripheral development of B cells in mouse and man." 2004, Immunol Rev 197:179-191.
Cines et al., "The ITP syndrome: pathogenic and clinical diversity." 2009, Blood 113(26):6511-21.
Duty et al., "Functional anergy in a subpopulation of naive B cells from healthy humans that express autoreactive immunoglobulin receptors." 2009, J Exp Med 206:139-151.
Klein et al., "Tracing the pre-B to immature B cell transition in human leukemia cells reveals a coordinated sequence of primary and secondary IGK gene rearrangement, IGK deletion, and IGL gene rearrangement." 2005, J Immunol 174(1):367-375.
Lamoureux et al., "Reduced receptor editing in lupus-prone MRL/lpr mice." 2007, J Exp Med 204(12):2853-2864.
Lefranc et al., "IMGT, the international ImMunoGeneTics information system." 2009, Nucleic Acids Res 37:D1006-12.
Li et al., "Autoreactive B cells in the marginal zone that express dual receptors." 2002, J Exp Med 195:181-188.
Prak et al., "Light chain editing in kappa-deficient animals: a potential mechanism of B cell tolerance." 1994, J Exp Med 180:1805-1815.
Silveira et al., "B cell selection defects underlie the development of diabetogenic APCs in nonobese diabetic mice." 2004, J Immunol 172(8):5086-5094.
Sutter et al., "A longitudinal analysis of SLE patients treated with rituximab (anti-CD20): factors associated with B lymphocyte recovery." 2008, Clin Immunol 126:282-290.
Van Dongen et al., "Design and standardization of PCR primers and protocols for detection of clonal immunoglobulin and T-cell receptor gene recombinations in suspect lymphoproliferations: report of the BIOMED-2 Concerted Action BMH4-CT98-3936." 2003, Leukemia 17:2257-2317.
Vela et al., "Rearrangement of mouse immunoglobulin kappa deleting element recombining sequence promotes immune tolerance and lambda B cell production." 2008, Immunity 28(2):161-170.
Wardemann et al., "Predominant autoantibody production by early human B cell precursors." 2003, Science 301:1374-1377.

* cited by examiner

*Primary Examiner* — Samuel Woolwine
(74) *Attorney, Agent, or Firm* — Riverside Law LLP

(57) ABSTRACT

The invention relates to methods and materials for diagnosing an autoimmune disease such as SLE, Type 1 diabetes, and the like. More particularly, the invention relates to methods and materials for assessing the frequency of recombination sequence (RS) rearrangement as a novel marker for an autoimmune disease. Such an assay can allow clinicians to diagnose an autoimmune disease based on the RS rearrangement frequency in an autoimmune patient as compared to an otherwise healthy control. In addition, the method includes identifying individuals who are at increased risk of developing autoimmunity. The method may also be helpful in directing the type of therapy and monitoring the effects of therapy in patients with autoimmune or non-autoimmune conditions.

7 Claims, 26 Drawing Sheets

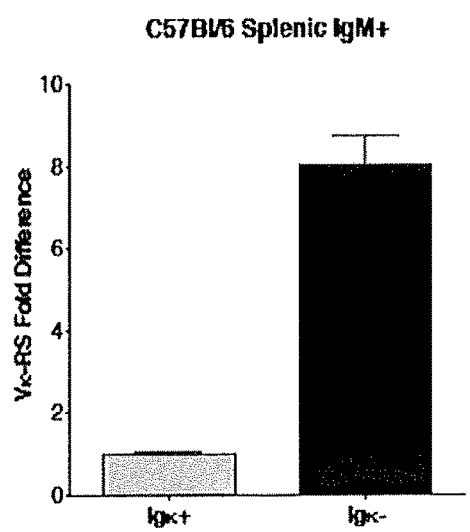 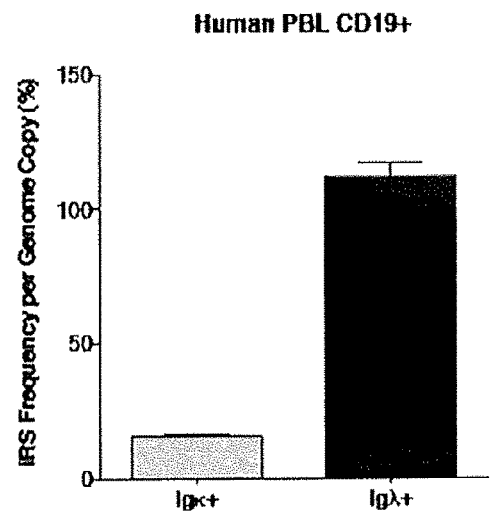
Figure 4A                    Figure 4B

Figure 7A
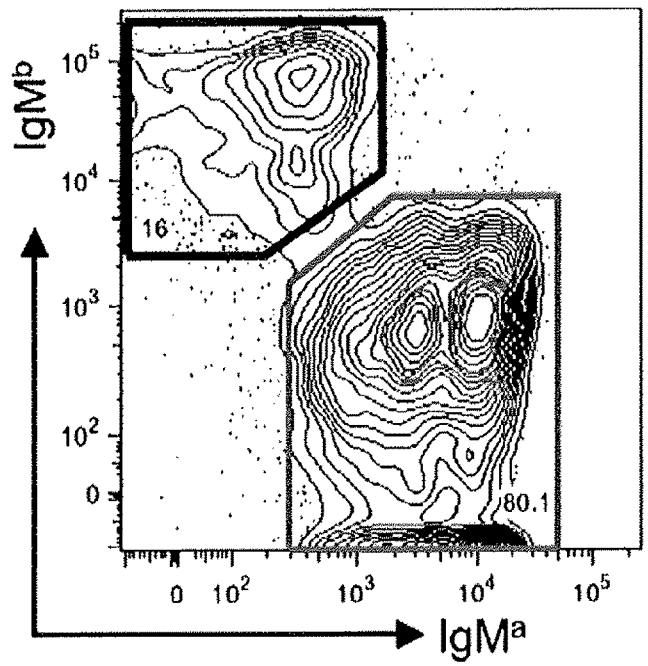
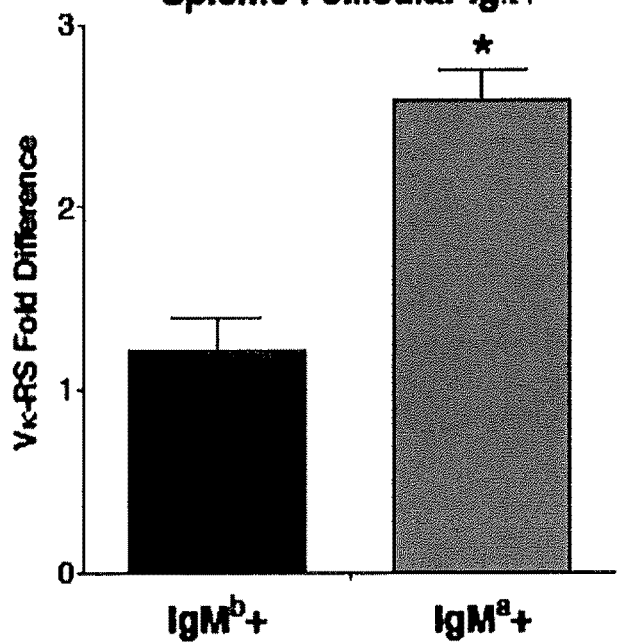
Figure 7B

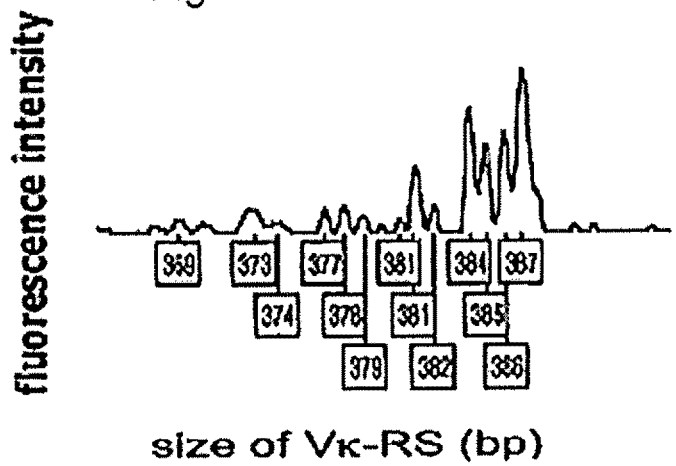
Figure 12A
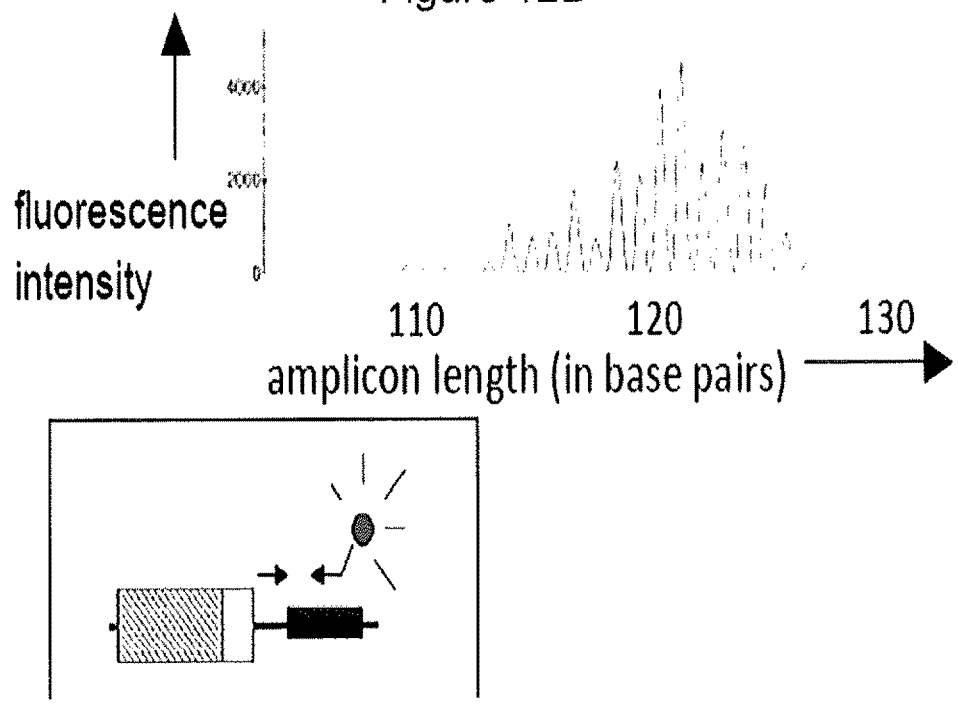
Figure 12B
Figure 12

Fig. 12c: Polyclonal vs. Clonal pattern on low-resolution spectratyping
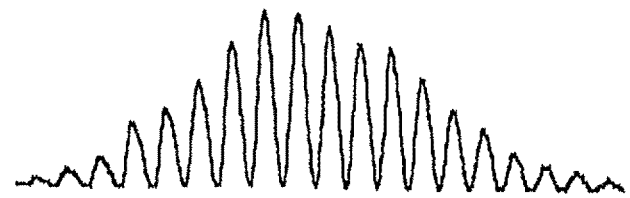
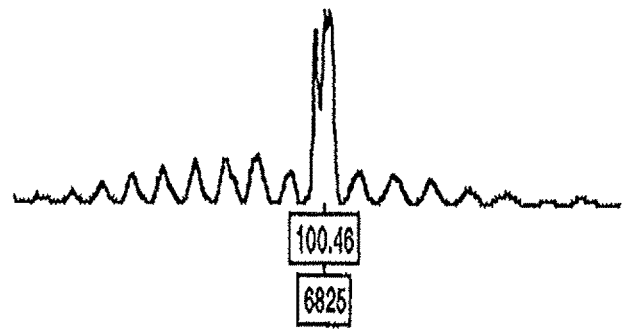
Figure 12c

B6: polyclonal pattern
B6.56R: oligoclonal pattern
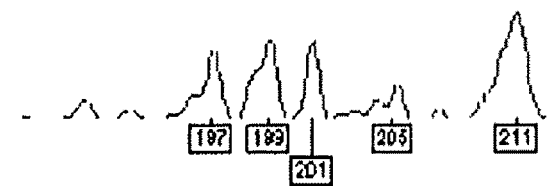
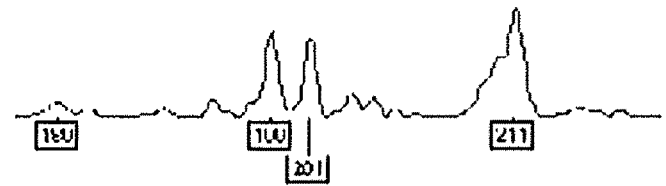
Figure 12d

```
                       SEQUENCE LISTING

<160> NUMBER OF SEQ ID NOS: 6

<210> SEQ ID NO 1
<211> LENGTH: 18
<212> TYPE: DNA
<213> ORGANISM: Artificial sequence
<220> FEATURE:
<223> OTHER INFORMATION: iRS-RS rearrangement primer

<400> SEQUENCE: 1
attgatgctg ccgtagcc                                               18

<210> SEQ ID NO 2
<211> LENGTH: 20
<212> TYPE: DNA
<213> ORGANISM: Artificial sequence
<220> FEATURE:
<223> OTHER INFORMATION: iRS-RS rearrangement primer

<400> SEQUENCE: 2
aggcttccta gggaggtcag                                             20

<210> SEQ ID NO 3
<211> LENGTH: 21
<212> TYPE: DNA
<213> ORGANISM: Artificial sequence
<220> FEATURE:
<223> OTHER INFORMATION: FAM-labeled hydrolysis probe

<400> SEQUENCE: 3
tctgcagctg cattttttgcc a                                          21

<210> SEQ ID NO 4
<211> LENGTH: 20
<212> TYPE: DNA
<213> ORGANISM: Artificial sequence
<220> FEATURE:
<223> OTHER INFORMATION: Beta -actin forward primer

<400> SEQUENCE: 4
cccagcacaa tgaagatcaa                                             20

<210> SEQ ID NO 5
<211> LENGTH: 20
<212> TYPE: DNA
<213> ORGANISM: Artificial sequence
<220> FEATURE:
<223> OTHER INFORMATION: beta -actin reverse primer

<400> SEQUENCE: 5
agtacttgcg ctcaggagga                                             20

<210> SEQ ID NO 6
<211> LENGTH: 20
<212> TYPE: DNA
<213> ORGANISM: Artificial sequence
<220> FEATURE:
<223> OTHER INFORMATION: Cy5-labeled hydrolysis probe

<400> SEQUENCE: 6
tgcctgagct gacctgggca                                             20
```

RECOMBINATION SEQUENCE (RS) REARRANGEMENT FREQUENCY AS A MEASURE OF CENTRAL B CELL TOLERANCE

STATEMENT REGARDING FEDERALLY SUPPORTED RESEARCH OR DEVELOPMENT

This invention was made with government support under grant no. U01DK070430 awarded by the National Institutes of Health. The government has certain rights in the invention.

CROSS-REFERENCE TO RELATED APPLICATIONS

The present application is a U.S. national phase application filed under 35 U.S.C. §371 claiming benefit to International Patent Application No. PCT/US2009/058033, filed on Sep. 23, 2009, which is entitled to priority under 35 U.S.C. §119(e) to U.S. Provisional Patent Application No. 61/099,392, filed on Sep. 28, 2008, which applications are incorporated by reference herein in their entireties.

BACKGROUND OF THE INVENTION

B cells are produced by and develop in bone marrow. During development, B cells progress through central tolerance checkpoints, rendering them non-self reactive. Central tolerance mechanisms include 1) clonal deletion, where B cells that recognize "self" (body antigens) are destroyed by apoptosis and 2) receptor editing where modifications in the B cell receptor are made to render the B cell no longer self reactive.

Throughout B cell development, signals transduced through the B cell antigen receptor (BCR) play an important role in regulating B cell maturation (Basten, A. R. et al. 1991. Immunol. Rev, 122:5; Nemazee, D. et al. 1991. Immunol. Rev, 122:117). However, BCR-induced signals can lead to dramatically different functional responses, depending on the maturational stage of the B cell. For instance, although both immature and mature B cells express the mature antigen-binding form of the BCR, immature B cells undergo negative selection, or are tolerized, in response to receptor ligation, while mature B cells are induced to proliferate and secrete immunoglobulin (Ig). Immature B cells in the bone marrow that have just begun to express surface IgM, as well as late-immature or transitional-stage B cells that have recently emigrated from the bone marrow to the spleen and that express high levels of surface IgM and low levels of surface IgD, are sensitive to this tolerization process (Carsetti, R. et al. 1995. J. Exp. Med. 181:2129; Allman, D. M. et al. 1992. J. Immunol. 149:2533; Allman, D. M. et al. 1993. J. Immunol. 151:4431). The sensitivity of immature B cells to tolerization following antigenic exposure is believed to be critical for the maintenance of immunological self-tolerance. Immature B cells are believed to be tolerized by a number of mechanisms including clonal anergy (Gooclnow, C. C. et al. 1988. Nature 334:676), receptor editing (Gay, D. et al. 1993. J. Exp. Med. 177:999), competition for follicular niches (Cyster, J. G. et al. 1994. Nature 371:389) and clonal deletion (Hartley, S. B. et al. 1993. Cell 72:325).

B cells undergo a random process of V(D)J recombination in order to generate the many distinct receptors needed to recognize a vast array of antigens. An inevitable consequence of this random process is the production of autoreactive B cells (Wardemann et al., 2003, Science 301(5638):1374-7). An important mechanism for tolerizing autoreactive B cells is receptor editing (Halverson et al., 2004, Nat Immunol 5(6):645-650). Receptor editing results in the alteration of B cell receptor specificity and is achieved by ongoing immunoglobulin (Ig) gene rearrangement, most commonly at the light chain loci (Gay et al., 1993, J Exp Med. 177(4):999-1008; Tiegs et al., 1993, J Exp Med. 177(4):1009-20; Radic et al., 1993, J Exp Med. 177(4):1165-73). Light chain rearrangement proceeds in an ordered fashion as B cells develop in the bone marrow, with κ genes recombining first, followed by rearrangement of the Recombining Sequence and λ (Lewis et al., 1982, Cell 30(3):807-816; Muller et al., 1988, J Exp Med. 168(6):2131-2137). The Recombining Sequence (known as the Kappa Deleting Element (KDE) in humans, hereafter RS) is a non-coding gene segment located 25 kb downstream of Cκ in the κ locus that is rearranged during continued Ig light chain gene rearrangement (Durdik et al., 1984, Nature 307 (5953):749-752; Siminovitch et al., 1985, Nature 316(6025): 260-262).

The recombining sequence (RS) of mouse and its human equivalent, the immunoglobulin (Ig) kappa deleting element (IGKDE), are sequences found at the 3' end of the Ig kappa locus (Igκ) that rearrange to inactivate Igκ in developing B cells. RS recombination correlates with Ig lambda (Igλ) light (L) chain expression and likely plays a role in receptor editing by eliminating Igκ genes encoding autoantibodies.

Systemic lupus erythematosus (SLE) is a chronic, inflammatory autoimmune disease characterized by the production of autoantibodies having specificity for a wide range of self-antigens. SLE autoantibodies mediate organ damage by directly binding to tissues and by forming immune complexes that activate immune cells. Organs targeted in SLE include the skin, kidneys, vasculature, joints, various blood elements, and the central nervous system (CNS). The severity of disease, the spectrum of clinical involvement, and the response to therapy vary widely among patients. This clinical heterogeneity makes it challenging to diagnose and manage lupus.

IDDM (Insulin-Dependent Diabetes Mellitus) otherwise known as Type 1 diabetes is another example of an autoimmune disease in which there is a need for better diagnostic assays. Three major theories have been advanced to account for the pathogenesis of the disease. The first is that IDDM is an inherited, or genetic disease. The second is that IDDM results from autoimmunity. The third theory states that IDDM is brought about by an environmental insult, presumably viral (Cotran, 1989 Robbins Pathologic Basis of Disease 994-1005; Foster, 1991 Harrison's Principles of Internal Medicine 1739-1759). Most agree that it is a combination of elements of all three theories that eventuates in IDDM, rather than each of the three acting independently in different individuals.

IDDM results from destruction of the insulin-producing β-cells of the pancreatic islets. Without insulin, glucose is not effectively taken up into such metabolically active tissues as muscle, liver or adipose tissue. The result is hyperglycemia. The hyperglycemia present in IDDM is thought to contribute to the major pathologies associated with the disease, such as those found in the peripheral nerves, retina, kidney, and vasculature.

Perhaps the most widely accepted therapy for treating IDDM involves daily injection of insulin in combination with blood glucose monitoring and eating behavior modification, indirectly reducing undesirable secondary side effects and the risk of life-threatening complications. Moreover, alternative therapies including pancreas and islet transplantation, autoantigen-based therapies (e.g., glutamic acid decarboxylase (GAD) therapy), and β cell-related peptide adjunctive therapies are being developed and tested.

There exists a need for new diagnostic tools aimed at identifying persons having or who are predisposed to diseases such as SLE or IDDM. The present invention addresses this need.

SUMMARY OF THE INVENTION

The invention provides a method of diagnosing an autoimmune disease in a mammal. The method comprises measuring the frequency of recombination sequence (RS) rearrangement in B cells from the mammal, wherein a reduced level of RS rearrangement compared to the level of RS rearrangement in an otherwise identical healthy mammal is an indication that the mammal has an autoimmune disease. Preferably, the mammal is a human.

In one embodiment, the reduced level of RS rearrangement confers an increased risk of the future development of autoimmunity.

In one embodiment, the autoimmune disease is type 1 diabetes. In another embodiment, the autoimmune disease is systemic lupus erythematosus (SLE).

In one embodiment, the RS rearrangement is measured based on quantitative PCR.

The invention provides a kit for diagnosing an autoimmune disease in a mammal comprising a nucleic acid molecule that is useful for measuring the frequency of RS rearrangement.

In one embodiment, the kit comprises a first primer that is directed to RS and second primer that is directed to Vκ.

In another embodiment, the kit comprises a first primer that is directed to RS and a second primer that is directed to iRS.

In another embodiment, the kit comprises a PCR-based calibrator for obtaining absolute RS frequency, wherein the calibrator is useful for controlling for DNA content, B cell fraction or κ/λ ratio.

The invention provides a method of assaying central B cell tolerance defect in a mammal. The method comprises measuring the frequency of recombination sequence (RS) rearrangements in B cells or B cell subsets from the mammal, wherein a reduced level of RS rearrangement compared to the level of RS rearrangement in an otherwise similar healthy mammal is an indication that said mammal has a central B cell tolerance defect.

The invention provides a method of identifying a mammal having an increased risk of developing autoimmunity. The method comprises measuring the frequency of recombination sequence (RS) rearrangements in B cells or B cell subsets from the mammal, wherein a reduced level of RS rearrangement compared to the level of RS rearrangement in an otherwise identical healthy mammal is an indication that said mammal has an increased risk of developing autoimmunity.

The invention provides a method for predicting a mammal's response to a type of B cell targeted therapy wherein the mammal has an autoimmune disease, the method comprising measuring the frequency of recombination sequence (RS) rearrangements in B cells or B cell subsets from the mammal, wherein a reduced level of RS rearrangement compared to the level of RS rearrangement in an otherwise identical healthy mammal provides a prediction of the response.

The invention provides a method of predicting development of autoimmunity in a mammal undergoing a type of B cell targeted therapy. The method comprising measuring the frequency of recombination sequence (RS) rearrangements in B cells or B cell subsets from the mammal, wherein a reduced level of RS rearrangement compared to the level of RS rearrangement in an otherwise mammal not undergoing B cell targeted therapy provides a prediction of the development of autoimmunity.

The invention provides a method for monitoring a shift in B cell tolerance in a mammal receiving therapy. The method comprising measuring the frequency of recombination sequence (RS) rearrangements in B cells or B cell subsets from the mammal, wherein a change in the level of RS rearrangement compared to the level of RS rearrangement in an otherwise identical mammal not receiving therapy is an indication of a shift in B cell tolerance.

The invention provides a method for monitoring shifts in B cell repertoire in a mammal receiving therapy. The method comprising measuring the frequency of recombination sequence (RS) rearrangements in B cells or B cell subsets from the mammal, wherein a change in the level of RS rearrangement compared to the level of RS rearrangement in an otherwise identical mammal not receiving therapy is an indication of a shift in B cell repertoire.

The invention provides a method of diagnosing an autoimmune disease in a mammal. The method comprising measuring the frequency of recombination sequence (RS) rearrangement in B cells from the mammal without the use of flow cytometry, wherein a reduced level of RS rearrangement compared to the level of RS rearrangement in an otherwise identical healthy mammal is an indication that said mammal has an autoimmune disease.

The invention provides a method of treating a mammal exhibiting a low RS level compared to the RS level from an otherwise identical healthy mammal. The method comprising administering an agent that targets B cells at the pre-B or transitional B cell stages.

The invention provides a method for evaluating bone marrow function in a mammal. The method comprising measuring the frequency of recombination sequence (RS) rearrangement in a test bone marrow cell, wherein a reduced level of RS rearrangement compared to the level of RS rearrangement in a control bone marrow cell is an indication of the developmental state of the test bone marrow cell.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 depicts the murine κ light chain locus illustrating successive Vκ-Jκ rearrangements followed by RS rearrangement. Two pathways of RS rearrangement are available. The first (1) involves recombination of an upstream unrearranged Vκ gene segment to RS, while the second (2) utilizes a non-canonical recombination signal sequence (iRS) in the Jκ-Cκ intron to rearrange to RS. Both result in functional inactivation of the Igκ locus. Exons are indicated by boxes, recombination signals are indicated by triangles and dashed lines with arrows illustrate the rearrangements.

FIG. 2, comprising

FIG. 3, comprising FIG. 3A is a schematic of the iRS-KDE rearrangements with respect to the PCR reaction. FIG. 3B depicts a standard curve for a cloned iRS-KDE rearrangement serially diluted in fibroblast DNA to 0.7% RS+ cells per 100 ng of input DNA. Also shown in FIG. 3B is a standard curve for Vκ-RS rearrangements.

FIG. 4, comprising FIGS. 4A and 4B, is a series of images demonstrating the correlation between RS rearrangement and extensive light chain rearrangement. Depicting are RS rearrangement levels as measured in Igκ+ (gray bars) and Igκ− (presumed to be λ+, black bars) from splenic B220+ IgM+ B cells of adult (3-4 month old) C57Bl/6 mice (n=5) (FIG. 4A) and CD19+9G4− peripheral B cells from healthy control subjects (n=26) (FIG. 4B). Murine data are presented as fold difference relative to the average RS level in C57Bl/6 splenic B220+ IgM+ Igκ+ B cells (+s.e.m.). Human data are depicted as rearrangement frequency per genome copy (+s.e.m.). RS rearrangement was observed to be increased by 8-fold amongst λ+ murine IgM+ B cells compared to κ+ cells.

FIG. 5, comprising FIG. 5A is a chart depicting Vκ-RS rearrangement levels in splenic Igκ+ follicular B cells from individual C57Bl/6 (black circles, n=5, r=0.8, p=0.1), MRL/lpr (white squares, n=4, r=−0.6, p=0.4), and NOD (gray triangles, n=5, r=−0.7, p=0.2) mice compared to frequency of Igκ+ splenic follicular B cells. RS rearrangement levels are calculated as fold difference relative to the average RS level in C57Bl/6 splenic B220+ IgM+ Igκ+ B cells, FIG. 5B depicts iRS rearrangement levels in CD19+ 9G4− Igλ+ (black diamonds, right y-axis) compared to CD19+ 9G4− Igκ/Igλ ratios (gray bars, left y-axis). iRS rearrangement levels are depicted from healthy control subjects (top panel, n=26), SLE patients (middle panel, n=23), and T1D patients (bottom panel, n=25) and are calculated as RS frequency per genome copy.

FIG. 6, comprising FIG. 6A is a chart depict Vκ-RS rearrangement levels quantified in bone marrow (BM) subsets from C57Bl/6 mice (n=5). Fr. D is the bone marrow pre-B cell fraction, as defined by Hardy and colleagues in the mouse (Shinton et al. J. Exp. Med. 1991). FIG. 6B depicts Vκ-RS rearrangement levels assayed in less mature (BP-1+, gray bar) and more mature (BP-1−, black bar) Fr, D B cells of C57Bl/6 mice (n=3). Data are depicted as fold difference relative to the average RS level in C57Bl/6 splenic B220+ IgM+ κ+ B cells (+s.e.m., **p≤0.01). FIG. 6C shows the tolerance checkpoints that are evaluated in the RS rearrangement assay and potential therapies for B cells at these stages of development. The RS assay monitors the level of antibody light chain gene rearrangement, which occurs mainly during the pre-B cell stage (Fr, D) in the bone marrow. If the Pre-B checkpoint is leaky, more autoreactive cells may make it to the naive/transitional stage. Also shown are two candidate drugs to target these two stages of early B cell development.

FIG. 7, comprising FIGS. 7A and 7B, is a series of images demonstrating that RS rearrangements are increased in B cells expressing an autoreactive heavy chain in self-tolerant mice. FIG. 7A is a flow cytometry of splenic follicular (B220+, AA4.1−, CD23+) κ+ B cells from heterozygous B6.56R mice depicting separation of B cells by immunoglobulin heavy chain allotype. FIG. 7B depicts Vκ-RS rearrangement frequencies measured in follicular B cells expressing endogenous heavy chains (IgM$^{b+}$, black bar) and the 56R anti-DNA heavy chain (IgM$^{a+}$, gray bar) from heterozygous B6.56R mice (n=2). Data are presented as fold difference relative to the average RS level in C57Bl/6 splenic B220+ IgM+ Igκ+ B cells (+s.e.m., *=p=0.03).

FIG. 8, comprising FIG. 8A depicts Vκ-RS rearrangement levels in bone marrow subsets of MRL/lpr mice (white bars, n=4) and NOD mice (gray bars, n=5). Data from C57Bl/6 mice are included for comparison. FIG. 8B depicts Vκ-RS rearrangement levels in κ+ splenic B cell subsets from C57Bl/6 (black bars, n=5), MRL/lpr (white bars, n=4), and NOD (gray bars, n=5) mice. Data are represented as fold difference relative to the average RS level in C57Bl/6 splenic B220+ IgM+ κ+ B cells (+s.e.m., *=p<0.05 relative to B6; **=p<0.01).

FIG. 9, comprising FIG. 9A depicts Vκ-RS rearrangement levels in B cell fractions of the MRL/lpr control strain, MRL/MpJ (n=4, white bars) compared to MRL/lpr (n=4, gray bars). FIG. 9B depicts Vκ-RS levels in B cell fractions of NOR mice (n=4, white bars) compared to NOD mice (n=5, gray bars). Data are represented as fold difference relative to the average RS level in C57B116 splenic B220+ IgM+ Igκ+ B cells (+s.e.m., *=p<0.05). FIG. 9 shows that the autoimmune-prone genetic background, rather than a deficiency in fas per se, contributes to the low level of RS rearrangement. This finding is relevant for the application of the assay as a predictor of future autoimmune disease development, since neither of the control strains had any symptoms or signs of autoimmunity at the time that RS levels were measured, yet both control strains develop future autoimmune disease.

FIG. 10, comprising FIG. 10A depicts iRS rearrangement levels in CD19+ 9G4− Igλ+ peripheral B cells from healthy controls (black circles, n=26), SLE patients (white squares, n=23), and T1D patients (gray triangles, n=25) compared to CD19+ Igκ/Igλ ratios. FIG. 10B depicts iRS rearrangement levels in CD19+ 9G4− Igλ+ peripheral B cells from healthy controls (black circles, n=26), SLE patients (white squares, n=23), and T1D patients (gray triangles, n=25) compared to subject age in years. FIG. 10C depicts mean iRS rearrangement frequencies compared between male (n=17) and female (n=57) subjects (+s.e.m., p=0.84). FIG. 10D depicts mean IRS rearrangement frequencies among Caucasian (n=45), African-American (n=18), and other (n=11, includes Asian, Hispanic, and Native American) ethnic groups (+s.e.m., p=0.67). Data are depicted as iRS rearrangement frequency per genome copy (r-values represent Spearman correlation coefficients).

FIG. 11, comprising FIGS. 11A and 11B depict iRS rearrangement frequencies as quantified in peripheral CD19+ 9G4− κ+ and CD19+ 9G4− κ+ B cells, respectively. Data represent the iRS levels in healthy control subjects (black circles, n=26), SLE patients (white squares, n=24 for κ+, n=23 for λ+), and T1D patients (gray triangles, n=25). Mean values are depicted as horizontal lines. The 10$^{th}$ percentile of iRS frequencies among control subjects is depicted as a dashed line. FIG. 11C depicts iRS rearrangement frequencies in CD19+ 9G4− κ+ peripheral B cells compared to frequencies in CD19+ 9G4− λ+ cell from healthy controls (black circles, n=26) and SLE and T1D patients (white squares, n=48). Data are depicted as iRS rearrangement frequency per genome copy. Trend lines are depicted for control (solid line, slope=5.4) and autoimmune patients (dashed line, slope=3.3; r-values indicate Spearman correlation coefficients, **=p<0.01).

FIG. 12A is an image depicting a spectratype of Vκ-RS rearrangements in DNA from κ+ splenocytes of a B6 (wild type) mouse. The image shows the diversity of RS rearrangements in IgM+, κ+ splenocytes from a B6 mouse.

FIG. 12B is an image demonstrating that human RS rearrangements also exhibit length diversity. Rearrangement length is given on the x-axis and fluorescence intensity of the PCR product is given on the y-axis. The PCR assay, which uses a fluorophore tagged primer, is also diagrammed.

FIG. 12C is an image demonstrating how the spectratyping technique can be used to distinguish polyclonal samples from those which contain an expanded clone of B cells. Spectratypes plot the fluorescence intensity as a function of the amplicon size in base pairs. The upper panel shows peripheral blood from a healthy human subject amplified with primers in VH framework region 3 and the introns of multiple JHs. The lower panel shows DNA from a lymphoblast line diluted 1:100 into normal polyclonal B cell DNA. The sensitivity of this assay for clonal expansion based on serial dilution experiments is approximately 1:500 in a sample of 100 ng. The top box in the lower spectratype indicates the product size in base pairs and the bottom box its fluorescence.

FIG. 12D is an image demonstrating how oligoclonal samples can be distinguished from polyclonal samples. Although the spectratyping assays highlighted in FIGS. 12C and 12D use primers that amplify the antibody heavy chain CDR3, FIGS. 12A and 12B show that RS rearrangements, like heavy chain rearrangements, also exhibit length diversity. Thus a similar approach can be used for RS rearrangements in the determination of clonal expansion. This is important, because the level of RS rearrangement could be influenced by clonal expansion and clonal expansions of B cells are more common in certain autoimmune diseases including lupus and Sjogren's syndrome.

FIG. 13, comprising FIG. 13A is a ten-color flow cytometric analysis of transitional cells in a normal adult human. CD19+ lymphocytes are analyzed for CD27 and CD38 and further for IgM, IgD, CD24 and CD10. Transitional cells (black), naive mature (grey), resting memory (aqua) and mature activated (purple). This analysis demonstrates that CD19+ lymphocytes staining brightly for CD38 and not staining for CD27 have immature features, consistent with transitional cells. The extended phenotype for human transitional cells based upon this and similar analyses and the published literature is: CD19+, CD38++, CD27−, IgD+, CD24++, CD10+/−. FIG. 13B is an image depicting Ki67 analysis in peripheral blood. CD19+ lymphocytes were separated into different subsets based upon CD27 vs. CD38 expression and analyzed individually for Ki67 staining (blue line=B cell subset; red line=isotype control). Plotted is the average percent of cells in each subset that is positive for Ki67 staining. Error bars+S.D. n=5 healthy adults. FIG. 13C is an image summarizing eleven SLE patients and thirteen adult control subjects analyzed for the transitional B cell fraction (percentage of CD19+ peripheral blood lymphocytes that stain as CD27−, CD38++). Four SLE patients (SLE group 1) have an elevated relative fraction of transitional B cells.

DETAILED DESCRIPTION OF THE INVENTION

Figure 1:
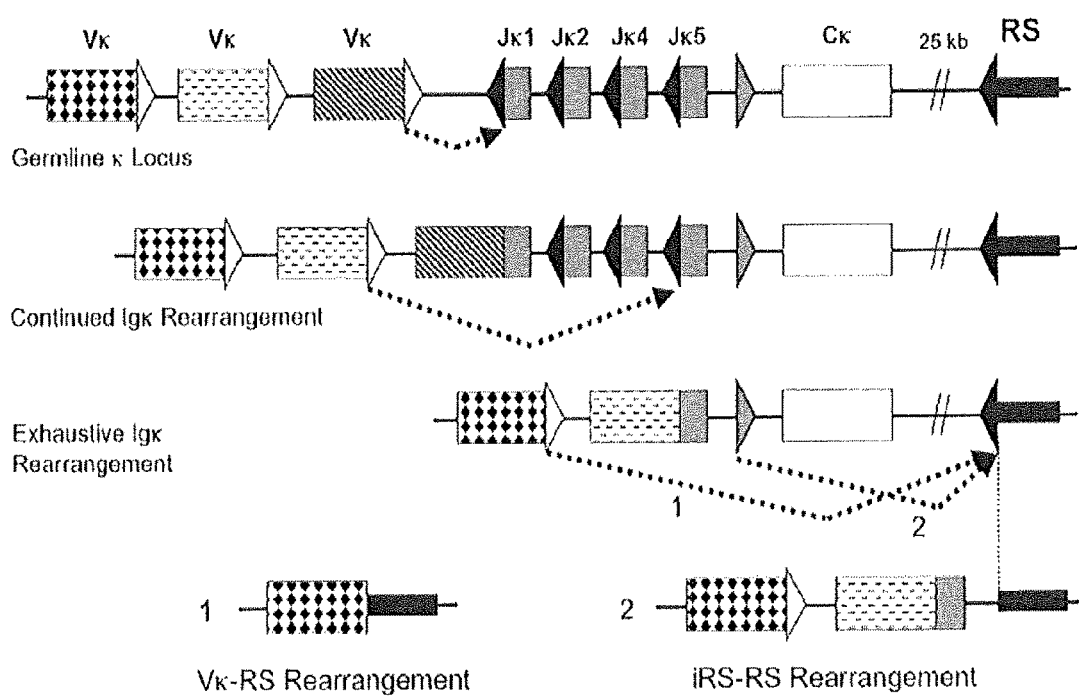
FIG. 1 is a schematic depicting RS rearrangement as a marker of extensive κ light chain rearrangement.

The present invention relates to methods and materials for assaying B cell tolerance as a diagnostic and pathological marker for an autoimmune disease including, but not limited to, systemic lupus erythematosus (SLE) and Type 1 diabetes. Autoreactive B cells contribute to autoimmunity by producing autoantibodies against "self" antigens that attack the body's own cells. B cell tolerance "checkpoints" have been identified during different stages of B cell development, and checkpoint abnormalities have been reported in patients having an autoimmune disease (Yurasov et al., 2005 JEM 201: 703-711).

The present invention provides methods and materials of detecting central (early) B cell tolerance using Recombination Sequence (RS) rearrangement frequency as a marker for B cell tolerance. RS rearrangement is a recombination of a non-coding gene segment in the κ antibody light chain locus that accompanies light chain receptor editing, a mechanism of early B cell tolerance. In some instance, RS rearrangement is the receptor editing process by which an antibody κ light chain that is directed against an autoantigen is inactivated. Thus in one embodiment, the invention provides a quantitative assay for measuring the frequency of RS rearrangement associated with κ light chain rearrangement. In some instances, the quantitative assay is quantitative PCR.

The present invention is based on the discovery that RS rearrangement is a marker for B cell tolerance. RS rearrangement can also be used as a marker for ongoing antibody light chain rearrangement. In some instances, a lower overall level of RS rearrangement is an indication of central B cell tolerance defect.

The invention includes a method for measuring RS rearrangement frequency in different B cell subsets from a mammal. Measuring RS rearrangement frequency in different B cell subsets from a mammal provides insight as to where tolerance is broken and therefore may enable elucidation of the cause of disease by identifying the B cell subset and/or developmental stages in which selection stringency may be relaxed and lead to autoimmunity. Thus, measuring RS rearrangements allows for the prediction of who is at increased risk of developing autoimmunity.

The invention also provides a method of measuring RS rearrangement frequency as a biomarker to allow for improved treatment of patients by providing a rationale for targeting therapy towards a particular B cell subset or a non-B cell compartment.

The invention provides compositions and methods for identifying markers of response to therapy of autoimmunity in a mammal. The invention includes methods of assessing RS frequency as a diagnostic tool to determine whether a patient is a candidate to receive the appropriate therapy. A lower RS frequency in a biological sample compared to a normal RS frequency of an otherwise identical healthy biological sample is predictive that the patient will be responsive to therapy directed against the autoimmune disease or B cells or both. The diagnostic test to determine responsiveness to the desired therapy is applicable to not only autoimmune diseases, but is applicable to all diseases or conditions associated with a defect in lymphocyte maturation.

The invention provides a quantitative PCR assay for measuring the frequency of RS rearrangement associated with κ light chain rearrangement. Preferably, the PCR assay includes the use of PCR based calibrators rather than flow cytometry to measure B cell fraction and the extent of antibody gene rearrangement (for example, the κ/λ ratio). More preferably, the assay is performed on genomic DNA from peripheral blood or whole blood.

The invention provides a diagnostic test for distinguishing diseases or conditions that are associated with lower RS frequency from normal RS frequency. In some instances, the diagnostic test is able to identify a subset of patients with a more aggressive disease state and/or is resistant to therapy.

The invention provides a diagnostic test for correlating the level of RS rearrangement with the level of disease. A low RS level identifies a subset of patients who have B cell abnormalities that can be treated with the appropriate therapy. For example, an appropriate therapy can be targeting early B cells such as targeting pre-B and transitional stages of B cell development.

The invention provides a quantitative PCR based assay that measures the frequency of RS rearrangement for diagnosing an autoimmune disease in a mammal. In some instance, this assay may be performed on purified B cells, on whole blood or on cells derived from a tissue or biopsy specimen. Flow cytometry or magnetic bead separation may be used to purify B cells and/or characterize the B cell fraction and kappa/lambda light chain ratio (κ/λ). In some instances, the assay may use PCR-based calibrators to control for DNA content, B cell fraction and κ/λ ratio to obtain the absolute RS frequency. In some instances, the assay may use ratios of different rearrangement products to define the level of light chain rearrangement in a given sample. For example, the ratio of Vκ-Jκ1 abundance to Vκ-RS abundance (where Vκ can represent one, a group or the entire set of Vκ gene segments) can be used to describe the level of rearrangement wherein low levels of rearrangement have high Vκ-Jκ1 to Vκ-RS ratios where as high levels of rearrangement have low Vκ-Jκ1 to Vκ-RS ratios. In some instances, primers and probes for other light chain gene rearrangements such as Vκ-Jκ5, Jκ1UP and lambda, can be used to evaluate the level of light chain rearrangement in a sample.

The invention provides a method for evaluating bone marrow function in a mammal. Because the RS rearrangement occurs principally in pre-B cells and pre-B cells reside in the bone marrow, the RS rearrangement assay of the invention can be used to provide insight into developmental processes in the bone marrow. These developmental processes are not necessarily intrinsic or restricted to the B cell lineage. Abnormal bone marrow processes include but are not limited to the following: dysregulated, accelerated, delayed or asynchronous mono, bi- or tri-lineage hematopolesis and/or a pathologic state in which bone marrow development or function is impaired such as myelofibrosis, myelodysplasia, anemia, pancytopenia or hematopoietic malignancy.

DEFINITIONS

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, to "alleviate" a disease means reducing the severity of one or more symptoms of the disease.

The term "amplification" refers to the operation by which the number of copies of a target nucleotide sequence present in a sample is multiplied.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules.

An "antibody heavy chain," as used herein, refers to the larger of the two types of polypeptide chains present in all antibody molecules in their naturally occurring conformations.

An "antibody light chain," as used herein and sometimes abbreviated L chain, refers to the smaller of the two types of polypeptide chains present in all antibody molecules in their naturally occurring conformations. κ and λ light chains refer to the two major antibody light chain isotypes.

By the term "applicator," as the term is used herein, is meant any device including, but not limited to, a hypodermic syringe, a pipette, an iontophoresis device, a patch, and the like, for administering the ligand of the invention to a mammal.

The term "auto-antigen" means, in accordance with the present invention, any self antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

As used herein, "autoantibodies" bind self-antigens and may contribute to autoimmune disease pathology.

The term "B-cell" in the present invention comprises all lymphocytes that develop in the adult bone marrow destined to produce antibodies. All different stages in the development of a B cell are included, such as pre B cells, naive, unprimed B-cells, which have not come into contact with an antigen yet or mature B cells, as well as plasma cells, which have been activated to proliferate and mature through antigen contact.

A "B cell progenitor" is a cell that can develop into a B cell. B cell progenitors include stem cells, early and common lymphoid progenitors. Cells that are committed to the B cell lineage include early pro-B cells, late pro-B cells, large pre-B cells, small pre-B cells, immature B cells, transitional B cells, follicular B cells, marginal zone B cells, B1 B cells, memory B cells, plasmablasts and plasma cells. Generally, early pro-B cells (that express, for example, CD43 or B220) undergo immunoglobulin heavy chain rearrangement to become late pro B cells. Following expression and signaling through the pre-BCR, B cells (now called pre-B cells) undergo immunoglobulin light chain gene rearrangement. Immature B cells include B220 (CD45R) expressing cells wherein the light and the heavy chain immunoglobulin genes are rearranged and expressed on the cell surface as IgM. In one embodiment, immature B cells express CD45R, class II, IgM, CD19 and CD40. Immature B cells can develop into mature B cells, which can produce immunoglobulins (e.g., IgA, IgG or IgM). Mature B cells have acquired surface IgM and IgD, are capable of responding to antigen, and express characteristic markers such as CD21 and CD23. Common biological sources of B cells and B cell progenitors include bone marrow, peripheral blood, spleen and lymph nodes. Plasma cells and plasmablasts are terminally differentiated B cells that are the predominant antibody-secreting cells. Memory B cells are, long-lived B lymphocytes produced following antigen stimulation. Typically, memory B cells express high affinity antigen-specific immunoglobulin (B cell receptor) on their cell surface.

As used herein, "B cell receptor editing" is the process of ongoing antibody gene rearrangement in a B cell. Receptor editing usually involves rearrangement at the κ or λ light chain locus and can modify the specificity of the antibody or B cell receptor (BCR). RS rearrangement is a kind of receptor editing rearrangement in the κ locus of mouse and man. RS rearrangement inactivates the κ locus in cis (on the same κ allele). Sometimes light chain editing results in the expression of more than one light chain per B cell (light chain allelic inclusion).

The term "coding sequence" as used herein means a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom.

The term "non-coding sequence" as used herein means a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, and the like.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, "clonal expansion" refers to the increase in number of one kind of B cell that harbors the same antibody.

As used herein, the term "diagnosis" refers to the determination of the nature of a case of disease. In some embodiments of the present invention, methods for making a diagnosis are provided which permit determination of SLE. In other embodiments of the present invention, methods for making a diagnosis are provided which permit determination of Type 1 diabetes.

As used herein, the term "disease" refers to a physiological state of an organism with any abnormal biological state of a cell. Disease includes, but is not limited to, an interruption, cessation or disorder of cells, tissues, body functions, systems or organs that may be inherent, inherited, caused by an infection, caused by abnormal cell function, abnormal cell division and the like. A disease that leads to a "disease state" is generally detrimental to the biological system, that is, the host of the disease. With respect to the present invention, any biological state, such as an infection (e.g., viral, bacterial, fungal, etc.), inflammation, autoinflammation, autoimmunity, anaphylaxis, allergies, premalignancy, malignancy, surgical, transplantation, physiological, and the like that is associated with a disease or disorder is considered to be a disease state. A pathological state is generally the equivalent of a disease state.

Disease states may also be categorized into different levels of disease state. As used herein, the level of a disease or disease state is an arbitrary measure reflecting the progression of a disease or disease state as well as the physiological response upon, during and after treatment. Generally, a disease or disease state will progress through levels or stages, wherein the affects of the disease become increasingly severe. The level of a disease state may be impacted by the physiological state of cells in the sample.

"An effective amount" as used herein, means an amount which provides a therapeutic or prophylactic benefit.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between).

As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

The term "gene" refers to a nucleic acid (e.g., DNA) sequence that includes coding sequences necessary for the production of a polypeptide (e.g.), precursor, or RNA (e.g., mRNA). The polypeptide may be encoded by a full length coding sequence or by any portion of the coding sequence so long as the desired activity or functional property (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 2 kb or more on either end such that the gene corresponds to the length of the full-length mRNA and 5' regulatory sequences which influence the transcriptional properties of the gene. Sequences located 5' of the coding region and present on the mRNA are referred to as 5'-untranslated sequences. The 5'-untranslated sequences usually contain the regulatory sequences. Sequences located 3' or downstream of the coding region and present on the mRNA are referred to as 3'-untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "housekeeping gene" as used herein refers to genes that are generally always expressed and thought to be involved in routine cellular metabolism. Housekeeping genes are well known and include such genes as glyceraldehyde-3-phosphate dehydrogenase (G3PDH or GAPDH), albumin, actins, tubulins, cyclophilin, hypoxanthine phsophoribosyl-transferase (HRPT), 28S, and 18S rRNAs and the like.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

As used herein, the term "hybridization" is used in reference to the pairing of complementary nucleic acids. Hybridization and the strength of hybridization (i.e., the strength of the association between the nucleic acids) is impacted by such factors as the degree of complementarily between the nucleic acids, stringency of the conditions involved, the $T_m$ of the formed hybrid, and the G:C ratio within the nucleic acids. A single molecule that contains pairing of complementary nucleic acids within its structure is said to be "self-hybridized." A single DNA molecule with internal complementarity could assume a variety of secondary structures including loops, kinks or, for long stretches of base pairs, coils.

The term "immunoglobulin" or "Ig", as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most mammals. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

"Mammal" as used herein refers to any warm-blooded vertebrate animal of the class Mammalia. Mammals include but are not limited to rodents, feline, cannines, caprines, camelids, equines, bovines, porcine, ovines, ungulates, cetaceans, and primates (e.g., monkeys, apes, and humans).

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant" as used herein, refers to either a nucleic acid or protein comprising a mutation.

A "nucleic acid" refers to a polynucleotide and includes poly-ribonucleotides and poly-deoxyribonucleotides.

The term "oligonucleotide" typically refers to short polynucleotides of about 50 nucleotides or less in length. It will be understood that when a nucleotide sequence is represented herein by a DNA sequence (e.g., A, T, G, and C), this also includes the corresponding RNA sequence (e.g., A, U, G, C) in which "U" replaces "T".

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences, provided that such changes in the primary sequence of the gene do not alter the expressed peptide ability to elicit passive immunity.

The term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

The term "reaction mixture" or "PCR reaction mixture" or "master mix" or "master mixture" refers to an aqueous solution of constituents in a PCR reaction that can be constant across different reactions. An exemplary PCR reaction mixture includes buffer, a mixture of deoxyribonucleoside triphosphates, primers, probes, and DNA polymerase. Generally, template RNA or DNA is the variable in a PCR.

As used herein, the term "Recombining Sequence" or "RS" (known as the Kappa Deleting Element (KDE) in humans) refers to a non-coding gene segment located downstream of Cκ in the κ locus that is rearranged during continued Ig light chain gene rearrangement, (Durdik et al., 1984, Nature 307 (5953):749-752; Siminovitch et al., 1985, Nature 316(6025): 260-262).

As used herein, "substantially purified" refers to being essentially free of other components. For example, a substantially purified cell is a cell which has been separated from other cell types with which it is normally associated in its naturally occurring state. In some instances, a population of substantially purified cells refers to a homogenous population of cells. In other instances, this term refers simply to a cell that have been separated from the cells with which they are naturally associated in their natural state.

As used herein, the terms "therapy" or "therapeutic regimen" refer to those medical steps taken to alleviate or alter a disease state, e.g., a course of treatment intended to reduce or eliminate the affects or symptoms of a disease using pharmacological, surgical, dietary and/or other techniques. A therapeutic regimen may include a prescribed dosage of one or more drugs or surgery. Therapies will most often be beneficial and reduce the disease state but in many instances the effect of a therapy will have non-desirable or side-effects. The effect of therapy will also be impacted by the physiological state of the host, e.g., age, gender, genetics, weight, other disease conditions, etc.

The term "therapeutically effective amount" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

"Immune response," as the term is used herein, means a process that results in the activation and/or invocation of an effector function in either the T cells, B cells, natural killer (NK) cells, and/or antigen-presenting cells (APCs). Thus, an immune response, as would be understood by the skilled artisan, includes, but is not limited to, any detectable antigen-specific or allogeneic activation of a helper T cell or cytotoxic T cell response, production of antibodies, T cell-mediated activation of allergic reactions, and the like.

"Immune cell," as the term is used herein, means any cell involved in the mounting of an immune response. Such cells include, but are not limited to, T cells, B cells, NK cells, antigen-presenting cells (to include dendritic cells, B cells and macrophages), monocytes, neutrophils, eosinophils, basophils, and the like.

"Instructional material," as that term is used herein, includes a publication, a recording, a diagram, or any other medium of expression which can be used to communicate the usefulness of the nucleic acid, peptide, and/or compound of the invention in the kit for effecting alleviating or treating the various diseases or disorders recited herein. Optionally, or alternately, the instructional material may describe one or more methods of alleviating the diseases or disorders in a cell or a tissue of a mammal. The instructional material of the kit may, for example, be affixed to a container that contains the nucleic acid, peptide, and/or compound of the invention or be shipped together with a container that contains the nucleic acid, peptide, and/or compound. Alternatively, the instructional material may be shipped separately from the container with the intention that the recipient uses the instructional material and the compound cooperatively.

By the term "modulating" an immune response, as used herein, is meant mediating a detectable increase or decrease in the level of an immune response in a mammal compared with the level of an immune response in the mammal in the absence of a treatment or compound, and/or compared with the level of an immune response in an otherwise identical but untreated mammal. The term encompasses perturbing and/or affecting a native signal or response thereby mediating a beneficial therapeutic response in a mammal, preferably, a human. By way of example, modulating an immune response of a human includes increasing the number of suppressor T lymphocytes present in the human, increasing secretion of immunosuppressive factors by a suppressor T lymphocyte in the human, decreasing the number of cytotoxic T lymphocytes present in the human, decreasing the cytotoxic activity of a cytotoxic T lymphocyte in the human, decreasing the amount of an antibody in the human, decreasing the amount of a complement protein in the human, decreasing the ability of a complement protein to interact with a cell in the human, and the like.

As used herein, the term "polymerase chain reaction" ("PCR") refers to the method of K. B. Mullis (U.S. Pat. Nos. 4,683,195 4,683,202, and 4,965,188, hereby incorporated by reference), which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the terms "PCR product," "PCR fragment," "amplification product" or "amplicon" refer to the resultant mixture of compounds after two or more cycles of the PCR steps of denaturation, annealing and extension are complete. These terms encompass the case where there has been amplification of one or more segments of one or more target sequences.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely related sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

To "treat" a disease as the term is used herein, means to reduce the frequency of the disease or disorder reducing the frequency with which a symptom of the one or more symptoms disease or disorder is experienced by an animal.

As used herein, "V(D)J recombination" refers to a mechanism of genetic recombination, which selects and assembles segments of genes encoding specific proteins with important roles in the immune system. This site-specific recombination reaction generates a diverse repertoire of T cell receptor (TCR) and immunoglobulin (Ig) molecules that are necessary for the recognition of diverse antigens from bacterial, viral, and parasitic invaders, and from dysfunctional cells such as tumor cells. V(D)J recombination is a site-specific DNA recombination carried out by the complex of RAG (recombinase activating gene) enzymes and non-homologous end joining machinery in developing B cells. Receptor editing also occurs by this mechanism.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

DESCRIPTION

Receptor editing is an important mechanism for tolerizing autoreactive B cells. Receptor editing results in the alteration of B cell receptor specificity and is achieved by ongoing immunoglobulin (Ig) gene rearrangement, most often at the Ig light chain loci. Light chain rearrangement proceeds in an ordered fashion as B cells develop in the bone marrow, with κ genes recombining first, followed by rearrangement of the Recombining Sequence and λ genes. The Recombining Sequence (known as the Kappa Deleting Element (KDE) in humans, hereafter RS) is a non-coding gene segment located about 25 kb downstream of Cκ in the κ locus that is rearranged during continued Ig (immunoglobulin or antibody) light chain gene rearrangement.

Continued antibody gene rearrangement, or otherwise receptor editing, is an important mechanism of central B cell tolerance. The present invention is based on the discovery that RS rearrangement frequency can be used as a marker for B cell tolerance defects.

In one embodiment, RS rearrangement frequency can be measured using a quantitative PCR based technique to measure a RS rearrangement product. In some instances, the RS rearrangement product is produced from a Vκ to RS rearrangement. In some instances, the RS rearrangement is produced from an iRS to RS rearrangement (iRS refers to intron to RS rearrangement or otherwise a rearrangement between the cryptic recombination heptamer in the Jκ-Cκ intron to the RS). In order to measure a Vκ to RS rearrangement, the PCR reaction includes a first primer that is directed to RS and a second primer that is directed to Vκ. Similarly, in order to measure an iRS to RS rearrangement, the PCR reaction includes a first primer that is directed to RS and a second primer that is directed to iRS. Amplicon abundance is quantified by the use of hydrolysis probes and compared either to a polyclonal B cell population in the case of Vκ-RS rearrangements or to a cloned iRS-RS rearrangement in the case of iRS-RS. Genomic DNA samples are also analyzed for DNA copy numbers by amplification for a housekeeping gene (β-actin).

Alternatively, or in addition, the level of RS rearrangement can be compared to other light chain gene rearrangements in DNA derived from either purified B cells, B cell subsets, tissue or whole blood. For example, to estimate the overall level of light chain gene rearrangement in a sample, one can measure the frequency of Vκ-Jκ1, Vκ-Jκ5, Vκ-RS and iRS. After normalization to β-actin and cloned amplification standards for each rearrangement product, the levels of these rearrangement products can be compared in the sample of interest. For example, a high ratio of RS, iRS and/or Vκ-Jκ5 to Vκ-Jκ1 or Jκ1UP indicates a high level of κ light chain rearrangement in the sample.

In one embodiment, RS rearrangement frequency can be used to estimate levels of antibody light chain receptor editing in various B cell populations. In some instances, RS rearrangement is a recombination event that inactivates the κ light chain locus. In another embodiment, the invention provides an assay for detecting central B cell tolerance in an autoimmune disease including, but not limited to systemic lupus erythematosus (SLE) and type 1 diabetes (T1D).

Autoimmune diseases that can be diagnosed according to the methods of the invention include, but are not limited to myasthenia gravis, idiopathic inflammatory myopathy, chronic neutropenia, rheumatoid arthritis, idiopathic thromcytopenia purpura, autoimmune hemolytic syndromes, antiphospholipid antibody syndromes, inflammatory bowel disease, Crohn's disease, ulcerative colitis, myocarditis, Guillian-Barre Syndrome, vasculitis, multiple sclerosis, neuromyelitis optica (Devic's syndrome), lymphocytic hypophysitis, Graves' disease, Addison's disease, hypoparathroidism, type 1 diabetes, systemic lupus erythematosus, pemphigus vulgaris, bullous pemphigoid, psoriasis, psoriatic arthritis, endometriosis, autoimmune orchitis, autoimmune erectile dysfunction, sarcoidosis, Wegener's granulomatosis, autoimmune deafness, Sjogren's disease, autoimmune uveoretinitis, interstitial cystitis, Goodpasture's syndrome, and fibromyalgia. However, the invention should not be limited to the aforementioned diseases. Rather, the invention is applicable to any autoimmune disease in which bone marrow-derived cells play a pathogenic role.

The RS rearrangement assay of the invention can be combined with immunophenotyping to analyze editing levels in different peripheral B cell subsets. As such, the invention provides a method of monitoring and staging defects in B cell tolerance.

Isolating and Culturing B Cells

The invention encompasses detecting RS rearrangement frequency as a marker for B cell tolerance, preferably early B cell tolerance. This is because an aspect of the invention serves to monitor pathways that B cells take as they become autoreactive, rather than monitoring relatively later events such as when the cells are producing autoantibodies.

The RS rearrangement assay of the invention gives an estimate of the overall level of light chain rearrangement in a defined population of B cells.

B cells can be isolated for a biological sample using methods known in the art. For example, a biological sample comprising the B lymphocyte population is usually the B lymphocyte population present in the blood of a subject, but may also be a tissue sample of the lymphoid system, such as for example lymph nodes or tonsils. The process for determining the quantitative and qualitative profile of the present invention does not necessarily require prior purification of the B lymphocyte population from the biological sample, thus greatly facilitating its implementation. Accordingly, the process may be performed on a heterogeneous cellular population, on a previously purified B lymphocyte population, or on a B lymphocyte subpopulation. Such B lymphocyte subpopulations include, for example, naive B lymphocytes, memory B cells, or according to the antigenic specificity antibodies they express, by performing previous classical purification techniques such as magnetic sorting or any cellular sorting technique.

In some instances, enriched populations of B cells are desired. The term "enriched", as used herein refers to at least 20%, preferably at least 30%, more preferably at least 40%, even more preferably at least 50%, even more preferably at least 60%, even more preferably at least 70%, even more preferably at least 80%, even more preferably at least 90%, and even more preferably 100% more than a sample that is not enriched with respect to B cells of a particular phenotype.

In some instances, the B cell population can be have the range of 0.1% to 100% B cells.

B cells can be isolated from peripheral blood using any known methods in the art. For example, an anti-κ light chain antibody can be used to isolate $κ^+$ cells from a peripheral blood sample. One skilled in the art would recognize that any desired B cell surface marker can be used to isolate a population of B cells of interest.

As a non-limiting example, an antibody specific for a B cell surface marker may be attached to a solid support to allow for separation. Procedures for separation may include magnetic separation, using antibody-coated magnetic beads or magnetic beads, affinity chromatography, cytotoxic agents joined to a monoclonal antibody or used in conjunction with a monoclonal antibody, e.g., complement and cytotoxins, and "panning" with antibody attached to a solid matrix, e.g., plate, or other convenient technique. Techniques providing accurate cell separation include fluorescence activated cell sorters, which can have varying degrees of sophistication, e.g., a plurality of color channels, low angle and obtuse light scattering detecting channels, impedance channels, etc., as well as magnetic activated cell sorters.

The separation techniques employed should maximize the purity and yield of the B cells in the specimen. The particular technique employed will, of course, depend upon the efficiency of separation, cytotoxicity of the method, the ease and speed of separation, and what equipment and/or technical skill is required. In some instances, the assay of the invention is used to measure DNA rather than RNA from a cell. Therefore, maximizing purity and cell yield is more desirable than cell maximizing viability.

Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well within the skill in the art.

Antibodies can be conjugated to biotin, which can then be removed with avidin or streptavidin bound to a support, or fluorochromes, which can be used with a fluorescence activated cell sorter (FACS), to enable cell separation. For example, cells expressing the κ light chain are separated from other cells by the expression of κ when using an anti-κ monoclonal antibody. Conveniently, the desired antibodies may be conjugated with markers, such as magnetic beads, which allow for direct separation, biotin, which can be removed with avidin or streptavidin bound to a support, fluorochromes, such as FITC, which can be used with a fluorescence activated cell sorter, or the like, to allow for ease of separation of the particular cell type. Any cell separation technique discussed herein may be employed which is not unduly detrimental to the yield or integrity of the remaining B cells. Other cell separation techniques include, but are not limited to, dense particles for density centrifugation, panning, an adsorption column, an adsorption membrane, and the like.

Alternatively or in addition, unseparated cells or tissues may be used in conjunction with either flow cytometry or a PCR-based calibration of the B cell fraction and extent of light chain rearrangement (κ/λ ratio, if flow is used). As a non-limiting example, white cells can be purified from whole blood by Ficoll-Hypaque or some other density centrifugation technique. Purified cells can then be analyzed for the B cell fraction and κ/λ ratio and these measurements can be used to interpret the RS rearrangement frequency. Alternatively, peripheral blood can be drawn into a tube for storing DNA (such as PAXgene) and the level of light chain gene rearrangement quantified by quantitative PCR assays for Vκ-Jκ1, Vκ-Jκ5, lambda, Vκ-RS, IRS and Jκ1UP.

The effectiveness of developmental and functional studies of individual subsets of cells has increased dramatically owing to the identification of additional subset markers and the extension FACS capabilities to simultaneously measure the expression of more markers on individual cells. Advancements in FACS allows for the unambiguously identification of most of the currently defined B-cell developmental subsets in the bone marrow (Hardy fractions A-F) and the functional B-cell subsets, including but not limited to transitional, B-1a, B-1b, B-2, marginal zone (MZ), IgM memory, switch memory, resting memory, and plasmablasts in the periphery. Additionally, the assay may be applied to phenotypically abnormal B lymphocyte populations that can be found at increased frequencies in autoimmune disease. Examples of such populations include 9G4 idiotype+ B cells, plasmablasts and naive D or allergic cells. However, the invention is not limited to these cells, but is applicable to any B cell populations. For example abnormal B cell populations that are associated with an autoimmune disease.

As a non-limiting example, where the anti-κ antibody is conjugated to a magnetic bead, a population of peripheral blood derived mononuclear cells is contacted with the magnetic bead-antibody conjugate under conditions suitable for binding of the antibody conjugate to κ antibodies displayed on the surface of the B cells. After incubation under conditions suitable for binding, such as but not limited to, an incubation at 4° C. for 20 minutes, the population of B-cells expressing the κ antibody (κ+) are selected by passing the entire sample through a magnetic-based separation apparatus. Upon evacuation or elution of free solution from the apparatus, only the magnetically-retained marker-containing cells remain. The κ+ B cells are then eluted from the apparatus, resulting in an enriched, isolated or purified population of κ+ B cells.

Primary B cells can be cultured for short periods of time using mitogens such as lipopolysaccharide (LPS) according to standard tissue culture procedures. For example, following their isolation, B cells are incubated in cell medium in a culture apparatus for a period of time or until the cells achieve a blast-like morphology and increase in number. The culturing apparatus can be any culture apparatus commonly used in culturing cells in vitro. Cultured B cells can be enriched for a particular (auto)specificity by co-culture with particular autoantigens and/or co-stimulation and/or the use of one or more cytokines.

Diagnostic

The invention provides methods for diagnosing a mammal, preferably a human, as having an autoimmune disease or an increased susceptibility for the future development of an autoimmune condition or for classifying patients with autoimmunity as having a particular form of lymphocyte tolerance defect. In one embodiment, the invention provides a method of diagnosing a mammal as having a defect in immune tolerance. In one embodiment, a mammal may be at increased risk for the development of autoimmunity if it is determined that the mammal contains B cells that exhibit a reduced RS rearrangement frequency compared to the RS rearrangement frequency of B cells from an otherwise similar but healthy mammal.

In one embodiment, the invention provides a diagnostic tool, such as an assay to detect RS rearrangement frequency and more specifically RS rearrangement associated with the κ light chain locus. In some instances, the diagnostic tool is an assay to detect genomic DNA from a population of B cells in order to detect the frequency of RS rearrangement. RS rearrangement is associated with recombination between RS and an upstream Vκ segment, whereby RS is a non-coding gene segment located downstream of a Cκ in the κ locus. An advantage of using an assay to detect RS rearrangement is that RS rearrangement does not encode any functional proteins therefore monitoring RS rearrangement provides a specificity-independent method of measuring repeated rearrangement attempts at the κ locus. The assay of the present invention does not evaluate B cell tolerance by way of monitoring serum autoantibodies, which are products of mature B cells. Therefore the assay of the present invention is able to monitor autoimmunity that arises during primary B cell maturation. Preferably, when antibody light chain gene rearrangement is taking place.

The mammal can be any mammal such as a human or mouse. That is, the mammal can be any animal that is determined to have an RS gene segment that undergoes recombination in lymphocytes. Any cell type can be isolated and evaluated. For example, peripheral blood mononuclear cells (PMBC), total white blood cells, lymph node cells, spleen cells, or tonsil cells can be isolated from a human patient and evaluated to determine if that patient has B cells that exhibit a decrease in RS rearrangement frequency. Typically, a reduced RS rearrangement frequency can be classified as being expressed at a level that is lower than or less than the average level observed in control samples if the RS rearrangement frequencies differ by at least 1-fold (e.g., 1.5-fold, 2-fold, 3-fold, or more than 3-fold). In addition when necessary, the control samples typically are the same type of cells as those isolated except that the sample is from an otherwise healthy mammal. When diagnosing an autoimmune disease, the control cells can be isolated from healthy mammals such as healthy humans who do not have an autoimmune disease. Any number of control mammals can be used to obtain the control cells. For example, control cells can be obtained from one or more healthy mammals (e.g., at least 5, at least 10, at least 15, at least 20, or more than 20 control mammals).

In some instances, the assay of the invention does not require control cells. This is because when performing the iRS assay, RS rearrangement can be titrated using cloned iRS-RS DNA.

In one aspect of the invention, the RS rearrangement levels are determined in a particular patient sample for which either diagnostic or prognostic information is desired. The level of RS rearrangement provides a profile of κ light chain rearrangements in B cells. Comparison of relative levels of RS rearrangement between B cell subsets or B cell populations from different samples can be useful in determining the manner or developmental stage in which tolerance is broken and/or the presence or susceptibility of B cells in a given patient to become autoimmune, and as such permits for diagnostic and prognostic analysis.

Moreover, by comparing relative RS rearrangement profiles from samples of subjects suffering from different disease states, information can be obtained regarding RS rearrangement frequency and the potential contribution of defective central B cell tolerance for each disease. Because the RS rearrangement is not functional or tied to any particular autoantibody specificity, it can be applied to any disease in which B cells may play a pathogenic role. The identification of RS rearrangement levels that are differentially present in diseased versus non-diseased tissues, as well as differential levels of RS rearrangement resulting in different prognostic outcomes, allows the use of this invention in a number of ways. For example, the use of a particular treatment regime may be informed by whether the patient exhibits an abnormal RS rearrangement frequency. Furthermore, the serial measurement of RS rearrangement frequencies in an individual subjected to standard or experimental therapies may serve as a biomarker for B cell tolerance or B cell repertoire shifts resulting from therapy.

The discovery of differential RS rearrangement frequencies allows for screening of drug candidates with an eye to mimicking or altering a particular RS rearrangement frequency. For example, screening can be performed to identify drugs that will alter the RS rearrangement frequency pattern or convert a poor prognosis pattern to a better prognosis pattern.

The present invention is based, at least in part, on the observation that RS rearrangement frequency is increased in B cells with an autoreactive antibody heavy chain and that levels of RS rearrangement differ in different B cell subsets. Furthermore, it was observed that RS rearrangement is less frequent in B cells from autoimmune strains of mice. These observations support the notion that RS rearrangement can be used as a marker for ongoing antibody light chain rearrangement (e.g., receptor editing) and B cell tolerance.

The present invention contemplates the diagnosis of an autoimmune disease in a mammal, preferably a human. The diagnosis is accomplished by the detection of RS rearrangement frequency in B cells as a marker for B cell tolerance. In one aspect, the detection of RS rearrangement in B cells of the human patient comprises determining the frequency of Vκ-RS rearrangement. In another aspect, the detection of RS rearrangement in B cells of the human patient comprises determining the frequency of intron to RS rearrangement (a rearrangement between the cryptic recombination heptamer in the Jκ-Cκ intro to the RS, referred to as iRS).

Detection of RS rearrangement or the corresponding PCR product can be accomplished using a nucleic acid probe. The nucleic acid probe, which in some instances recognizes internal sequence to the PCR produce, can have a sequence of about 10 to about 100 nucleotides in length. More preferably, the nucleic acid probe is about 15 nucleotides to about 20 nucleotides in length.

The probes and primers according to the invention can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of $^{32}P$, $^{33}P$, $^{35}S$ or $^{3}H$. The nonradioactive entities are selected from ligands such as biotin, avidin, streptavidin or digoxigenin, haptenes, dyes, and luminescent agents such as radioluminescent, chemoluminescent, bioluminescent, fluorescent or phosphorescent agents. The probe can also contain multiple moieties, for example both a fluorophore and a quencher for use as a hydrolysis probe in real-time PCR. Additionally, the PCR primers themselves can have moieties such as fluorophores for spectratyping applications (for use in capillary electrophoresis to determine clonality, oligoclonality or polyclonal distributions of rearrangement products).

Suitable nucleic acid molecules also can encode a B cell receptor (BCR) or one or more variable portions of a BCR (e.g., a variable portion of a light chain of an immunoglobulin, including any single Vκ, Vκ family or degenerate primer that recognizes most VκS, as well as sequences in the Jκ-Cκ region or in or near RS). For example, a primer that detects a single Vκ gene segment might be situated in CDR1 or CDR2 while a primer that detects a family of Vκ gene segments or many different Vκs might be situated in a less variable portion of the Vκ gene segment such as a framework or leader region.

Populations of nucleic acid molecules encoding a BCR, or a variable portion of a BCR, can be isolated from mononuclear cells. In general, a population of mononuclear cells can be obtained from a biological sample then nucleic acids can be extracted from the mononuclear cells. For example, blood (e.g., peripheral blood) or a tissue sample (e.g., biopsy) can be obtained from a subject (e.g., a human) and mononuclear cells isolated from such samples using known techniques. For example, density gradient separation medium (e.g., Ficoll-Paque (Amersham Biosciences, Piscatanaway, N.J.)) can be used to isolate mononuclear cells. Alternatively, negative or positive selection strategies can be used to obtain particular populations of lymphocytes (e.g., B cells).

Nucleic acids can be obtained from the cells using known techniques. Nucleic acid herein refers to DNA, including genomic DNA. The nucleic acid can be double-stranded or single-stranded (i.e., a sense or an antisense single strand) and can be complementary to a nucleic acid encoding a polypeptide. The nucleic acid content may also be a DNA extraction performed on a fresh or fixed tissue sample.

Routine methods also can be used to extract genomic DNA from a blood or tissue sample, including, for example, phenol extraction. Alternatively, genomic DNA can be extracted with kits such as the QIAamp™ Tissue Kit (Qiagen, Chatsworth, Calif.), the Wizard™ Genomic DNA purification kit (Promega, Madison, Wis.), the Puregene DNA Isolation System (Gentra Systems, Inc., Minneapolis, Minn.), and the A.S.A.P.™ Genomic DNA isolation kit (Boehringer Mannheim, Indianapolis, Ind.).

There are many methods known in the art for the detection of specific nucleic acid sequences and new methods are continually reported. A great majority of the known specific nucleic acid detection methods utilize nucleic acid probes in specific hybridization reactions. Preferably, the detection of hybridization to the duplex form is a Southern blot technique. In the Southern blot technique, a nucleic acid sample is separated in an agarose gel based on size (molecular weight) and affixed to a membrane, denatured, and exposed to (admixed with) the labeled nucleic acid probe under hybridizing conditions. If the labeled nucleic acid probe forms a hybrid with the nucleic acid on the blot, the label is bound to the membrane.

In the Southern blot, the nucleic acid probe is preferably labeled with a tag. That tag can be a radioactive isotope, a fluorescent dye or the other well known materials. Another type of process for the specific detection of nucleic acids of exogenous organisms in a body sample known in the art are the hybridization methods as exemplified by U.S. Pat. No. 6,159,693 and No. 6,270,974, and related patents. To briefly summarize one of those methods, a nucleic acid probe of at least 10 nucleotides, preferably at least 15 nucleotides, more preferably at least 25 nucleotides, having a sequence complementary to a desired region of an RS rearrangement is hybridized in a sample, subjected to depolymerizing conditions, and the sample is treated with an ATP/luciferase system, which will luminesce if the RS rearrangement polynucleotide sequence is present. In quantitative Southern blotting, RS levels can be compared to the germline (unrecombined) band for Jκ-Cκ or to other antibody genes or their rearrangements (Coleclough et al., 1981 Nature 290: 372-378).

A further process for the detection of hybridized nucleic acid takes advantage of the polymerase chain reaction (PCR). The PCR process is well known in the art (U.S. Pat. No. 4,683,195, No. 4,683,202, and No. 4,800,159). To briefly summarize PCR, nucleic acid primers, complementary to opposite strands of a nucleic acid amplification target sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe.

In PCR, the nucleic acid probe can be labeled with a tag as discussed before. Most preferably the detection of the duplex is done using at least one primer directed to a RS. In yet another embodiment of PCR, the detection of the hybridized duplex comprises electrophoretic gel separation followed by dye-based visualization.

With respect to the sensitivity of PCR, the process of the present invention allows a skilled artisan to determine the quantitative and qualitative profile of the RS rearrangement of a given type of an immunoglobulin light chain in B cells, thereby determining the frequency of RS rearrangement. This determination allows one to assess tolerance defects in the patient.

DNA amplification procedures by PCR are well known and are described in U.S. Pat. No. 4,683,202. Briefly, the primers anneal to the target nucleic acid at sites distinct from one another and in an opposite orientation. A primer annealed to the target sequence is extended by the enzymatic action of a heat stable DNA polymerase. The extension product is then denatured from the target sequence by heating, and the process is repeated. Successive cycling of this procedure on both DNA strands provides exponential amplification of the region flanked by the primers.

Amplification is then performed using a PCR-type technique, that is to say the PCR technique or any other related technique. Two primers (e.g., Vκ and RS primers for the amplification of Vκ-RS rearrangement; JCint and KDE primers for the amplification of iRS-RS rearrangement), complementary to the RS segment and the variable segment or the Jκ-Cκ intron and the RS segment, respectively, of a given type of Igκ, are then added to the nucleic acid content along with a polymerase, and the polymerase amplifies the DNA region between the primers.

The expression specifically hybridizing in stringent conditions refers to a hybridizing step in the process of the invention where the oligonucleotide sequences selected as probes or primers are of adequate length and sufficiently unambiguous so as to minimize the amount of non-specific binding that may occur during the amplification. The oligonucleotide probes or primers herein described may be prepared by any suitable methods such as chemical synthesis methods.

Hybridization is typically accomplished by annealing the oligonucleotide probe or primer to the DNA under conditions of stringency that prevent non-specific binding but permit binding of this DNA which has a significant level of homology with the probe or primer.

Among the conditions of stringency is the melting temperature (Tm) for the amplification step using the set of primers, which is in the range of about 55° C. to about 70° C. Preferably, the Tm for the amplification step is in the range of about 59° C. to about 72° C. Most preferably, the Tm for the amplification step is about 60° C.

Typical hybridization and washing stringency conditions depend in part on the size (i.e., number of nucleotides in length) of the DNA or the oligonucleotide probe, the base composition and monovalent and divalent cation concentrations (Ausubel et al., 1994, eds Current Protocols in Molecular Biology).

In a preferred embodiment, the process for determining the quantitative and qualitative profile according to the present invention is characterized in that the amplifications are real-time amplifications performed using a labeled probe, preferably a labeled hydrolysis-probe, capable of specifically hybridizing in stringent conditions with the segment of the RS rearrangement (e.g., Vκ-RS rearrangement; iRS-RS rearrangement). The labeled probe is capable of emitting a detectable signal every time each amplification cycle occurs, allowing the signal obtained for each RS rearrangement to be measured.

The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. Hydrolysis probes are preferred. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents. In the present invention, the inventors have employed a FAM-labeled probe, but other probes may be used in a convenient manner. For spectratyping and/or light chain calibration assays, different primers or probes may harbor different fluorophores and be used in multiplex PCR, using a real time thermal cycler such as the Roche LC480 that can measure multiple wavelengths of emitted light simultaneously and perform compensation for spectral overlap.

Among the stringent conditions applied for any one of the hydrolysis-probes of the present invention is the Tm, which is in the range of about 65° C. to 75° C. Preferably, the Tm for any one of the hydrolysis-probes of the present invention is in the range of about 67° C. to about 70° C. Most preferably, the Tm applied for any one of the hydrolysis-probes of the present invention is about 67° C.

In another preferred embodiment, the process for determining the quantitative and qualitative profile according to the present invention is characterized in that the amplification products can be elongated, wherein the elongation products are separated relative to their length. The signal obtained for the elongation products is measured, and the quantitative and qualitative profile of the labeling intensity relative to the elongation product length is established for each of the RS rearrangements.

The elongation step, also called a "run-off reaction," allows one to determine the length of the RS rearrangement. The length can be determined using conventional techniques, for example, using gels such as polyacrylamide gels for the separation, DNA sequencers, and adapted software. Because RS rearrangements display length heterogeneity, B cell populations can be analyzed for clonal diversity or, conversely, clonal restriction. This analysis may be required if RS frequencies fall well outside of the normal range.

Preferably, the process for determining the quantitative and qualitative profile according to the present invention is characterized in that the iRS-KDE or otherwise referred to as iRS-RS rearrangements are amplified with 5'-ATT GAT GCT GCC GTA GCC-3' (SEQ ID NO:1) and 5'-AGG CTT CCT AGG GAG GTC AG-3' (SEQ ID NO:2) primers and detected with 5'-TCT GCA GCT GCA TTT TTG CCA-3' FAM-labeled hydrolysis probe (SEQ ID NO:3).

In one aspect, the invention includes a primer that is complementary to an endogenous RS and more particularly the primer includes 12 or more contiguous nucleotides substantially complementary to the sequence of RS nucleotide sequence. Preferably, a primer featured in the invention includes a nucleotide sequence sufficiently complementary to hybridize to an RS nucleotide sequence of about 12 to 25 nucleotides. More preferably, the primer differs by no more than 1, 2, or 3 nucleotides from the RS nucleotide sequence. In another aspect, the length of the primer directed to RS can vary in length, preferably about 15 to 28 nucleotides in length (e.g., 16, 17, 18, 19, 20, 21, 22, 23, 24, 25, 26, or 27 nucleotides in length). The murine RS primer (2nd DS RSS) is 21 nucleotides long. The human RS primer (KDEQR1) is 20 nucleotides long.

In another aspect, the invention includes a primer that is complementary to an endogenous Vκ gene segment or a non-canonical recombination sequence (IRS) found in the Jκ-Cκ intron. More particularly the primer includes 12 or more contiguous nucleotides substantially complementary to the Vκ gene segment or iRS nucleotide sequence. Preferably, a primer featured in the invention includes a nucleotide sequence sufficiently complementary to hybridize to a Vκ gene segment or iRS nucleotide sequence of about 12 to 25 nucleotides. More preferably, the primer differs by no more than 1, 2, or 3 nucleotides from the Vκ gene segment or iRS nucleotide sequence. In another aspect, the length of the primer directed to Vκ gene segment or iRS target sequence can vary in length, preferably about 15 to 28 nucleotides in length (e.g., 16, 17, 18, 19, 20, 21, 22, 23, 24, 25, 26, or 27 nucleotides in length). The murine Vκ primer ($V_{Sch}$, designed and published by Schlissel et al., 1989 Cell 58: 1001-1007) is 32 nucleotides in length, is degenerate in sequence and amplifies approximately 80% of murine Vκ gene segments (Prak et al., 1994 J. Exp. Med, 180: 1805-1815). The human iRS primer, huJCintQF2, is 18 nucleotides long. In principle any degenerate Vκ, or Vκ family-specific, or Jκ-Cκ intron primer (upstream of the intron RSS) or Vκ-specific primer could be used in this assay.

In some instances, the present invention includes obtaining quantitative and qualitative information directly from a biological sample, preferably a blood sample, without the requirement of purifying a B cell type. In this instance, the measurement of RS rearrangement frequency may need to be adjusted for the B cell fraction and κ/λ ratio of the B cells in the sample. A quantitative DNA PCR on unfractionated cells provides a rapid method, and makes it possible to distinguish and quantify RS rearrangement frequency in B cells.

One aspect of the present invention is to provide a method for determining the quantitative and qualitative profile of RS rearrangement in a B cell population present in a tissue sample, characterized in that it comprises the following steps: (a) obtaining genomic DNA from a tissue sample or the cellular DNA extract of the tissue sample, (b) performing the amplification of the DNA obtained at the step (a) with a first and second primer wherein the primers are able to amplify an RS rearrangement, and (c) determining the quantitative and qualitative profile of RS rearrangement in the B cell. In parallel the sample may be analyzed for B cell content and the κ/λ ratio, as described above. Preferably, the DNA amplified is an iRS-KDE or otherwised referred to as iRS-RS rearrangement and more preferably, the first primer has the sequence of 5'-ATT GAT GCT GCC GTA GCC-3' (SEQ ID NO:1) and the second primer has the sequence of 5'-AGG CTT CCT AGG GAG GTC AG-3' (SEQ ID NO:2).

Another embodiment of the present invention is a method for the diagnosis of an autoimmune disease. In some instances, the autoimmune disease is associated with a defect in immune tolerance of a given autoantigen by a B lymphocyte population in a mammal. The method comprises: 1) determining the quantitative and qualitative profile of RS rearrangement from a tissue sample or cellular body fluid of a subject according to the present invention, and 2) comparing the quantitative and qualitative profile obtained in step 1) with a control quantitative and qualitative profile of RS rearrangement, the demonstration of a significant modification of the profile obtained at the step 1) being an indication of the autoimmune disease. Preferably, a lower level of RS rearrangement is an indication of an autoimmune disease.

In some instances, RS rearrangement frequency is increased in B cells with an autoreactive antibody heavy chain. As such, very high RS frequencies could point to altered lymphocyte selection or clonal expansion.

In other instances, RS rearrangement is less frequent in B cells from a mammal having an autoimmune disease or being at increased risk for the development of autoimmunity. This is because it is believed that a decrease in RS rearrangement frequency is associated with a defect in central tolerance.

The method for the diagnosis of an autoimmune disease according to the present invention is also applicable to the diagnosis of a B cell lymphoma, an immunodepressive disease or condition in which bone marrow based development of lymphocytes is altered bone marrow transplantation, an allergic reaction or vigorous immune response.

Another embodiment of the present invention is a method for a follow-up test of a treatment of a condition associated with expression of an autoantibody by a B lymphocyte population in a subject, the method comprising: (1) optionally determining the quantitative and qualitative profile of RS rearrangement from a tissue sample of the a subject according to the present invention before the treatment of the subject, (2) determining, during the treatment, the quantitative and qualitative profile of the given type of RS rearrangement at given times from tissue samples or body fluids of the subject according to the present invention, and (3) comparing the quantitative and qualitative profiles of RS rearrangement obtained in step (2) and optionally in step (1) with each other and optionally with a control quantitative and qualitative profile of RS rearrangement, the demonstration of a significant modification of the RS rearrangement profile obtained from each sample being an indication of a condition associated with alterations in central B cell tolerance, peripheral selection of B cells or shifts in the lymphocyte repertoire.

Preferably, a relative lower level RS rearrangement is an indication of an autoimmune disease.

Preferably, the method for the in vitro follow-up according to the present invention is characterized in that the condition is an autoimmune disease, a B cell lymphoma, an immunodepressive disease, a bone marrow transplantation, or an allergic reaction.

Another embodiment of the present invention is a kit for determining the quantitative and qualitative profile of the RS rearrangement in a B lymphocyte population present in a tissue sample, characterized in that it comprises a first primer associated with either a Vκ gene segment or iRS nucleotide sequence with a second primer associated with RS sequence. The kit further comprises an instruction material for the use thereof. The kit can also comprise a probe, optionally labeled. The kits may further comprise suitable reagents.

Another embodiment of the present invention is the use of the kit according to the present invention for the diagnosis of a condition associated with an abnormal RS rearrangement. Preferably, the condition is an autoimmune disease or an increased susceptibility to develop autoimmunity, a B cell lymphoma, or an immunodepressive disease. In another preferred embodiment, the condition is associated with a relatively lower RS rearrangement frequency.

Therapy

The immune system responds to foreign antigens by provoking immune responses while simultaneously remaining unresponsive to self-antigens. Although this immunologic discrimination is very efficient, failure of these basic immunoregulatory processes leads to chronic infectious diseases, autoimmune diseases and tumors. Systemic Lupus Erythematosus (SLE) is a systemic autoimmune disease characterized by the production of autoantibodies specific for many nuclear antigens including ssDNA, dsDNA, histones and Smith antigen (Sm). In some cases, these autoantibodies form immune complexes that contribute to multi-organ pathology. In any event, the event(s) that initiate disease remain unclear but tolerance mechanisms such as deletion (dsDNA), receptor editing (dsDNA), B1 formation (Sm), anergy (HEL) and suppression of T helper ($T_H$) cells by T regulatory ($T_{reg}$) cells have been described.

The present invention can be practiced for medical or veterinary purposes. Suitable mammalian subjects include but are not limited to humans, non-human primates, rats, mice, rabbits, hamsters, cats, dogs, sheep, cattle, pigs, goats and horses. In particular embodiments, the mammalian subject has an autoimmune disease (e.g., SLE) or other condition that is the result of aberrant B cell development, autoantibody production and/or secretion and/or is at risk for developing an autoimmune disease or other condition that is the result of aberrant B cell development or autoantibody production and/or secretion. At risk individuals can be identified using the RS rearrangement assays discussed elsewhere herein. The results from the RS rearrangement assays can be combined with family history, genetic analysis or the onset of early symptoms associated with the disease. The mammalian subject can further be an animal model (e.g., a mouse) of autoimmune disease or autoreactive B cell dysfunction (e.g., models of tolerance and loss of tolerance). The mammalian subject is optionally "in need of" the methods of the invention, for example, because the subject is suspected of having or has been diagnosed as having autoimmune disease or is at risk for autoimmune disease or has, is diagnosed with or is at risk for any other condition that results from aberrant B cell development or bone marrow developmental process, autoantibody production and/or secretion by autoreactive B cells.

One advantage of the methods of the invention as compared with traditional methods of treating autoimmune disease is that the inventive methods evaluate receptor editing and/or defects in early stage B cells. Identification of a bone marrow or transitional B cell tolerance checkpoint using the RS assay may help guide therapy for autoimmune disease. For example, Belimumab (anti-BLyS) may function to increase the stringency of the transitional B cell selection checkpoint. The RS assay may identify a subset of patients with autoimmunity who are responsive to anti-BLyS or bone marrow targeted therapy.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLES

The invention is now described with reference to the following Examples. These Examples are provided for the purpose of illustration only, and the invention is not limited to these Examples, but rather encompasses all variations which are evident as a result of the teachings provided herein.

The following examples demonstrate a method for assaying central B cell tolerance in an autoimmune disease such as systemic lupus erythematosus (SLE) and type 1 diabetes (T1D). In both of these diseases B cells play a critical pathogenic role. Autoantibodies are a prominent feature, whether they be directed against nuclear antigens (in SLE) (Bernstein et al., 1982, Clin Exp Immunol. 48(1):43-51) or pancreatic β-cell antigens such as GAD65 or insulin (in T1D) (Leslie et al., 2004, Diabetes 53(12):3033-3040). The results presented herein describe the status of central tolerance in individuals with SLE or T1D using RS rearrangement frequency as a marker.

The materials and methods employed in the experiments disclosed herein are now described.

Mice

B6.56R mice have been described previously (Sekiguchi et al., 2006, J Immunol 176(11):6879-6887). C57Bl/6, NOD, NOR, MRL/lpr, and MRL/MpJ mice were obtained from Jackson Laboratories. All animal experiments were performed on 3-4 month old mice in accordance with protocols approved by the University of Pennsylvania School of Medicine Animal Care and Use Committee.

Flow Cytometry

Figure 2A:
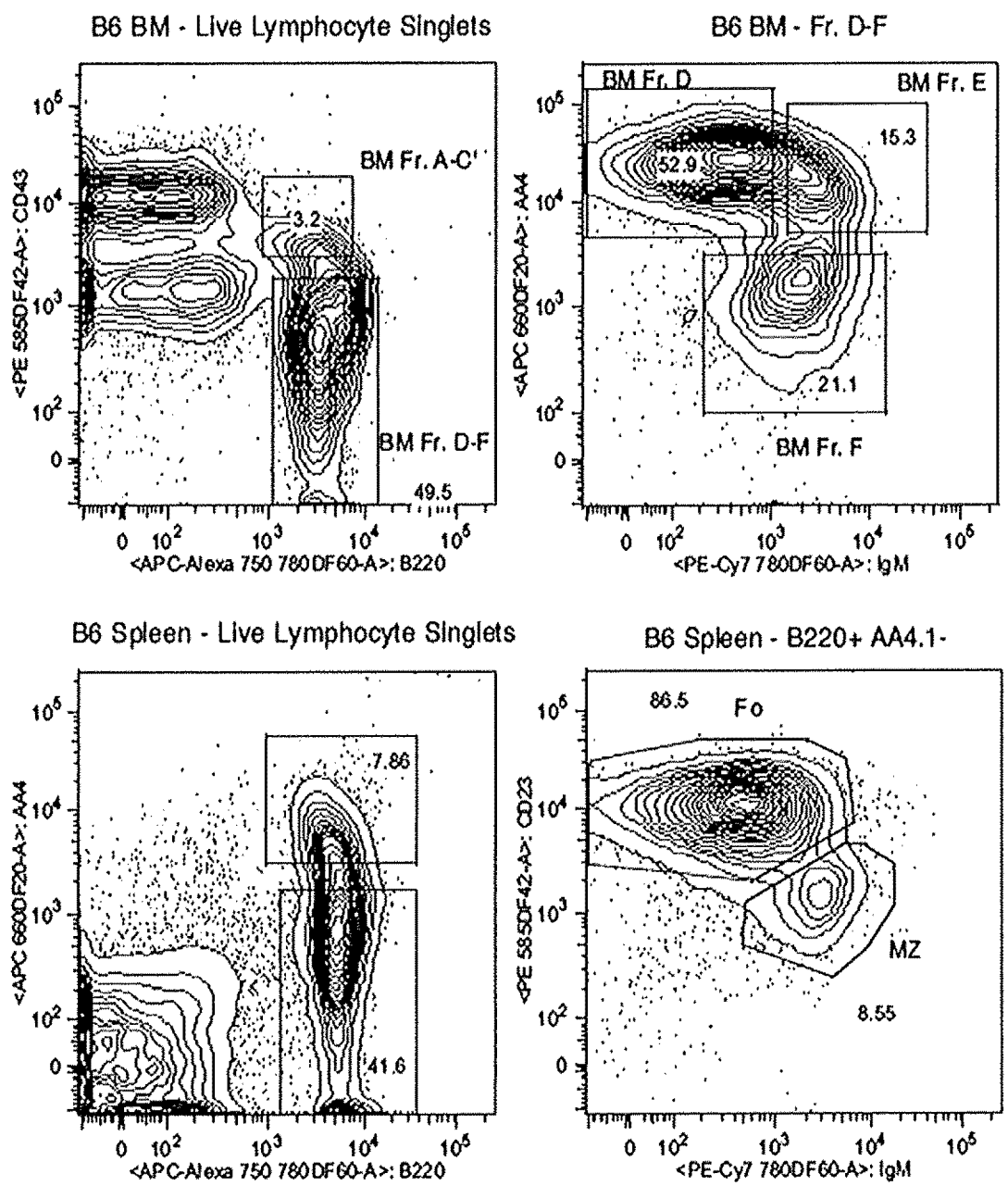
FIGS. 2A through 2D, is a series of images depicting flow cytometric analysis of murine and human lymphocytes. Cytometric analysis of bone marrow and splenic B cells from (FIG. 2A) C57Bl/6, (FIG. 2B) MRL/lpr, (FIG. 2C) NOD mice, and (FIG. 2D) healthy human subjects. DAPI staining was used for live-dead discrimination and doublets were excluded by pulse-width gating. Each plot represents 50,000 live singlet events.
Figure 2B:
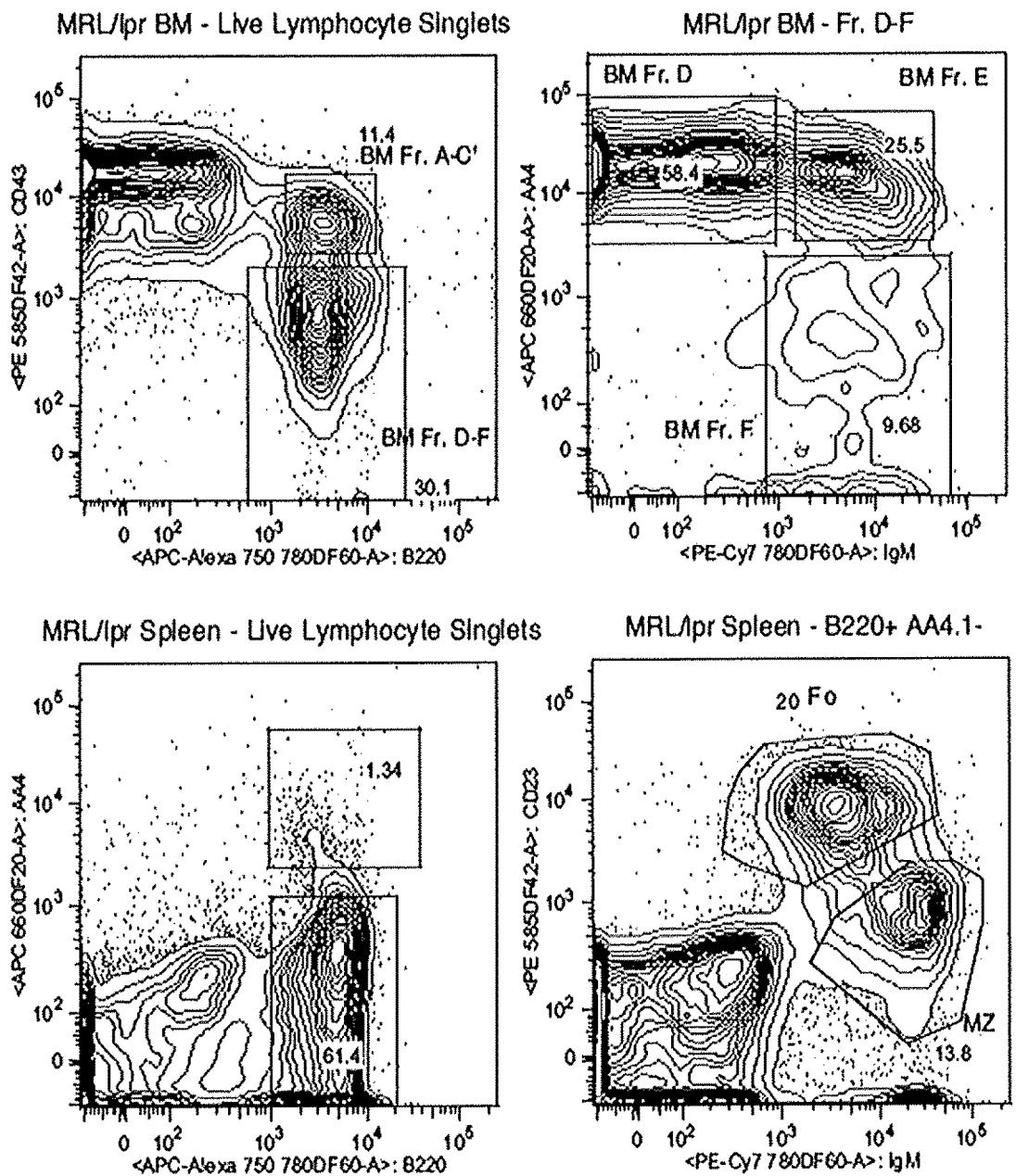
Figure 2C:
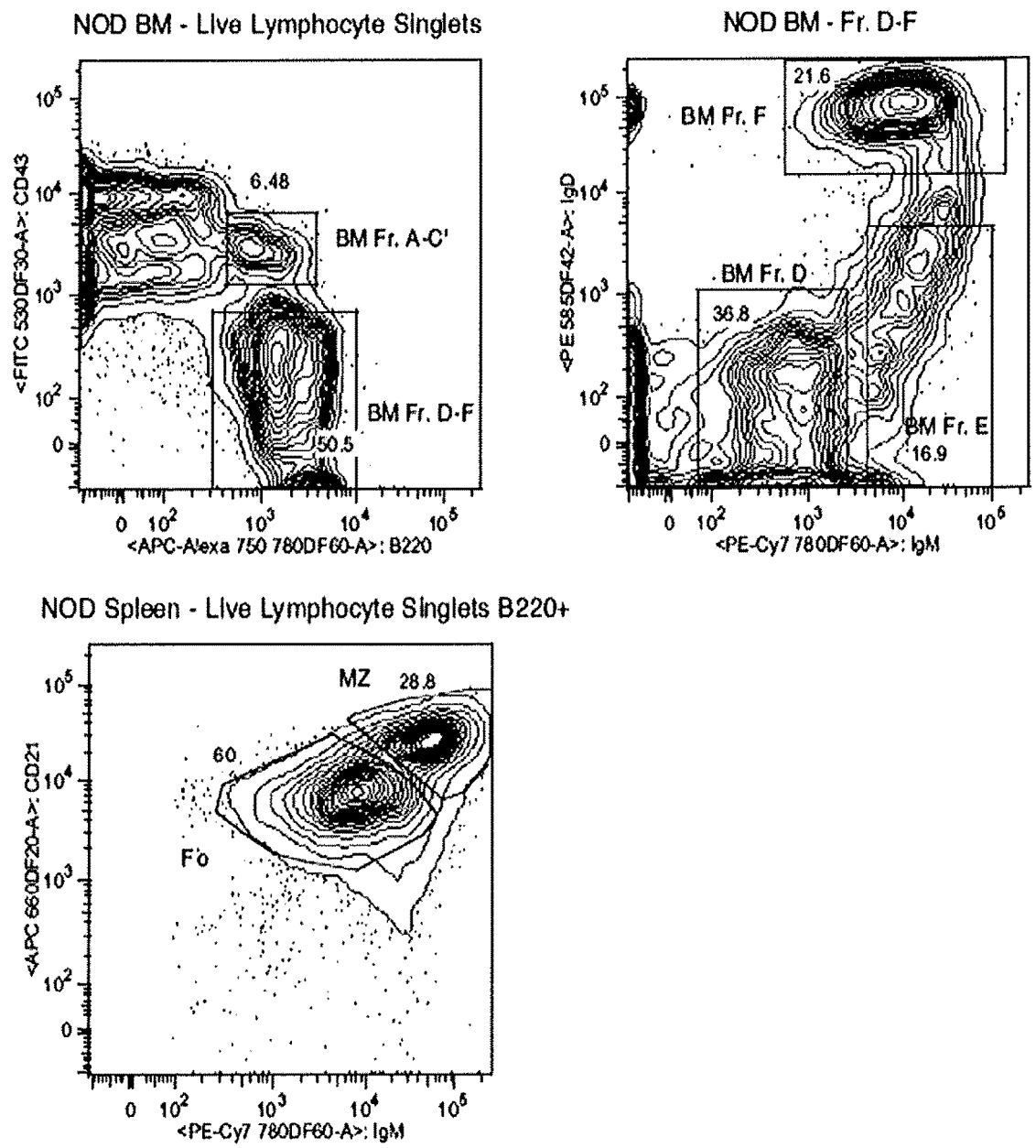
Figure 2D:
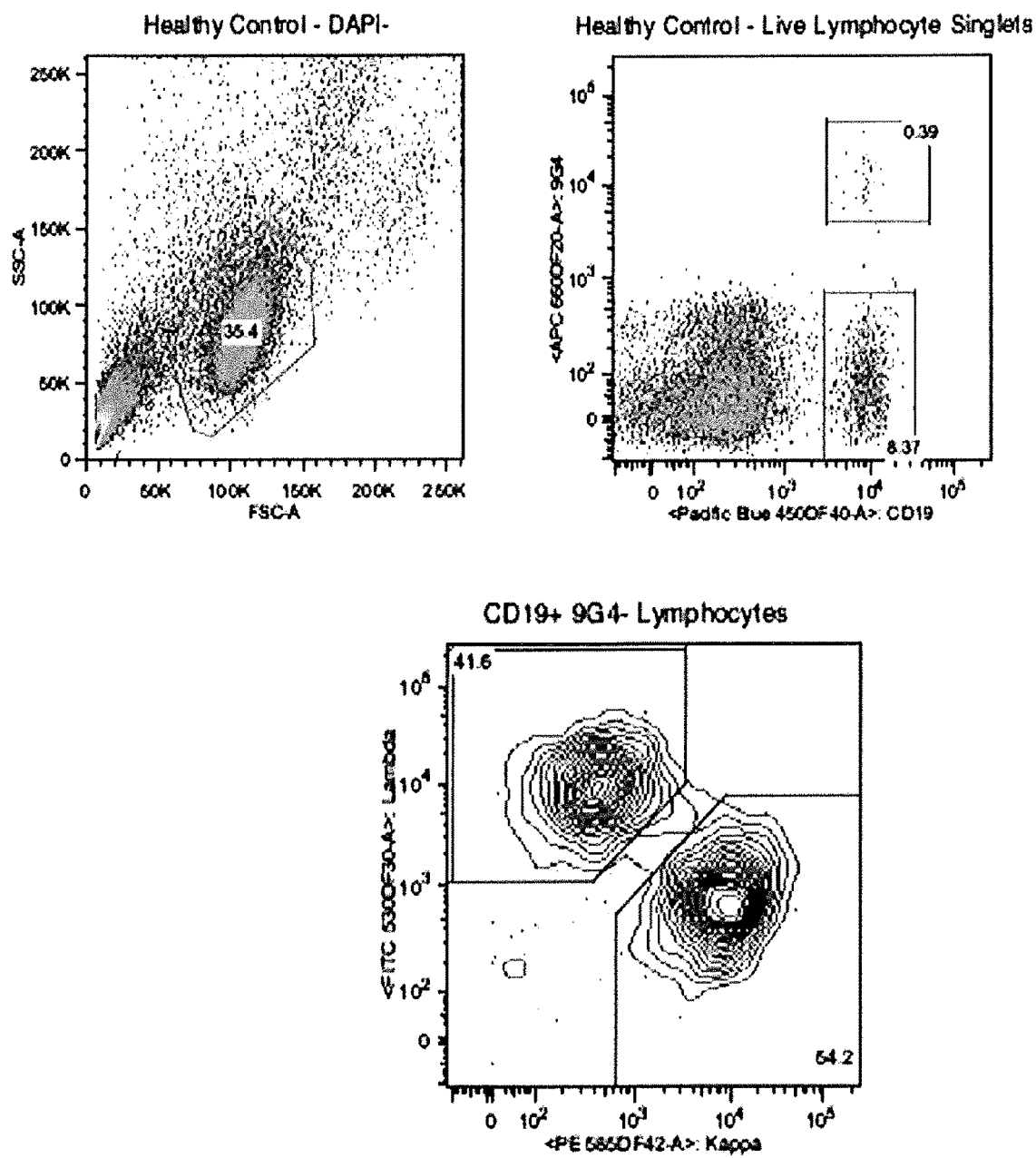

Murine cell suspensions were prepared from femurs, tibias, and spleens in FACS buffer (PBS, 0.5% BSA, 0.01% $NaN_3$, 1 mM EDTA) following hypotonic RBC lysis (ACK Lysing Buffer, BioWhittaker). B cell populations are depicted in FIG. 2. Due to poor reactivity of AA4.1 antibodies in NOD and NOR mice (Langmuir et al., 1993, Intl Immunol 5(2):169-177), bone marrow subsets in these mice were defined using IgD in place of AA4.1 (FIG. 2C). Human B cells were isolated from whole blood using Lymphocyte Separation Medium (MP Biomedicals, Solon, Ohio) followed by resuspension in FACS buffer. Murine lymphocytes were stained using anti-IgM-PE-Cy7 (II/41), anti-IgD-PE (11-26), anti-B220-APC-AF750 (RA3-6B2) (eBioscience), and anti-Igκ-FITC (187.1), anti-BP-1-FITC (6C3), anti-CD43-PE (S7), anti-CD23-PE (B3B4), anti-AA4.1-APC (BD-Pharmigen). Human lymphocytes were stained with anti-CD19-Pacific Blue (Caltag Laboratories) and anti-Igλ-FITC, anti-CD27-FITC, anti-Igκ-PE, anti-CD38-PE-Cy7 (BD Pharmingen). To maximize efficient use of patient samples for additional experiments not described here, CD19+ B cells marked by the anti-idiotypic monoclonal antibody 9G4, which recognizes $V_H$4-34 heavy chain rearrangements (Isenberg et al., 1993, Br J Rheumatol. 32(10):876-82), were excluded from human CD19+ B cell populations described herein (FIG. 2D). 9G4Id+ cells comprised 5.1%, 5.7%, and 4.2% of total CD19+ B cells from control, SLE, and T1D subjects, respectively. All cells were sorted using the BD FACSAria with sort purities over 90%.

Murine bone marrow subsets include Fr. A-C' (B220+, CD43+), Fr, D (B220+, CD43−, AA4.1+, IgM−), Fr. E (B220+, CD43−, AA4.1+, IgM+), and Fr. F (B220+, CD43−, AA4.1−, IgM+). Murine splenic populations were identified as follows: follicular B cells (B220+, AA4.1−, IgM$^{int}$, CD23+), and marginal zone B cells (B220+, AA4.1−, IgM$^{bri}$, CD23−). In NOD and NOR mice, bone marrow populations were defined as follows: Fr. D (B220+, CD43−, IgD+, IgM+), Fr. E (B220+, CD43−, IgD−, IgM+), and Fr. F (B220+, CD43−, IgD+, IgM+). Human peripheral B cells were isolated on the basis of CD19, κ, and λ expression. To maximize efficient use of patient samples for additional experiments, CD19+ B cells marked by the anti-idiotypic monoclonal antibody 9G4, which recognizes $V_H$4-34 heavy chain rearrangements (Isenberg et al., 1993 Br J Rheumatology 32: 876-882), were excluded from human CD19+ B cell populations described herein. 9G4Id+ cells comprised about 5.1%, 5.7%, and 4.2% of total CD19+ B cells from control, SLE, and T1D subjects, respectively. However, any antibody that recognized $V_H$4-34 heavy chain rearrangements can be used.

Quantitative PCR

Genomic DNA was isolated from sorted B cells using the Gentra PureGene Tissue Kit (Qiagen). Quantitative PCR (40° C. 10 min., 95° C. 10 min., followed by 60 cycles at 95° C. 10 sec., 60° C. 30 sec., 72° C. 1 sec.) was performed on 15-50 ng template DNA in a 20 μL reaction mix containing IX Light-Cycler 480 Probes Master Mix (Roche Applied Science), 0.5U LightCycler Uracil-DNA Glycosylase (Roche Applied Science), 0.5 μM forward primer, 0.5 μM reverse primer, and 0.2 μM hydrolysis probe using a LightCycler 480 real-time PCR system (Roche Applied Science). Primer and probes used for real-time PCR to monitor iRS-KDE rearrangements in B cell populations are as follows: iRS-KDE rearrangements were amplified with 5'-ATT GAT GCT GCC GTA GCC-3' (SEQ ID NO:1) primer and 5% AGG CTT CCT AGG GAG GTC AG-3' (SEQ ID NO:2) primer and detected with 5'-TCT GCA GCT GCA TTT TTG CCA-3' (SEQ ID NO:3) PAM-labeled hydrolysis probe. For each sample, the intronic region of the reference control gene β-actin was amplified in a separate well with forward primer 5'-CCC AGC ACA ATG AAG ATC AA-3' (SEQ ID NO:4) and reverse primer 5'-AGT ACT TGC GCT CAG GAG GA-3' (SEQ ID NO:5) and detected with a Cy5-labeled hydrolysis probe 5'-TGC CTG AGC TGA CCT GGG CA-3' (SEQ ID NO:6). A cloned iRS-KDE rearrangement was serially diluted in fibroblast DNA to 0.7% RS+ cells per 100 ng of input DNA.

Figure 3A:
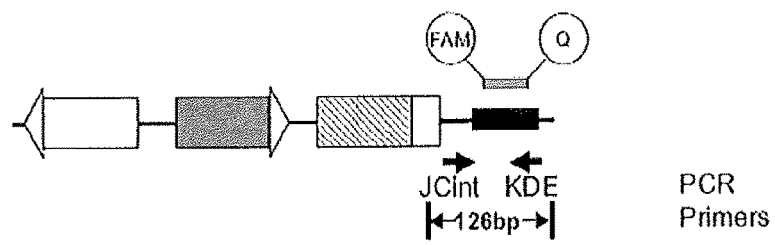
FIGS. 3A and 3B, is a series of images depicting Real-time PCR to monitor iRS-KDE rearrangements in B cell populations.
Figure 3B:
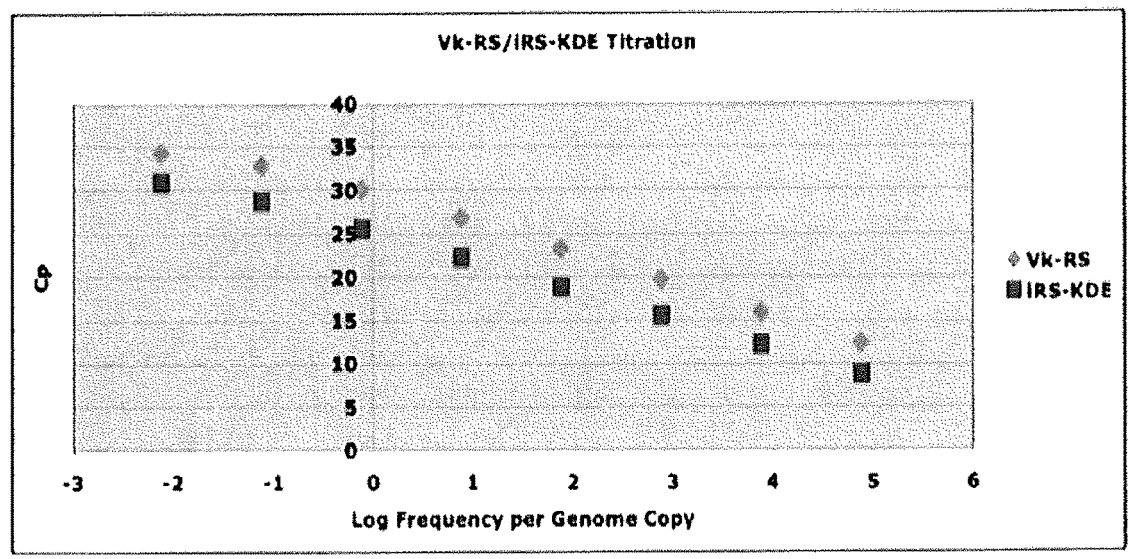

The amount of Vκ-RS product in each mouse sample was normalized to the amount of β-actin product and compared to the normalized target value in wild-type C57Bl/6 B220+ IgM+ splenocytes to determine a relative quantity (comparative $C_T$ (DDC$_T$) method). The frequency of iRS-KDE rearrangements in each human sample was determined via absolute quantification using a standard curve generated by serial dilution of a cloned iRS-KDE rearrangement resuspended with 100 ng human fibroblast DNA (FIG. 3). To determine the number of genome copies, β-actin was measured via absolute quantification using a standard curve consisting of serially diluted human fibroblast DNA. Reactions were performed in duplicate and samples with inconsistent replicates or β-actin cycle numbers greater than 35 were excluded.

Human Subjects

Volunteer healthy adult subjects with no history of autoimmune disease, no active viral or bacterial infection, or current use of immunomodulatory or immunosuppressive drugs were recruited. Women who were nursing, pregnant, or who were planning on becoming pregnant during the duration of this study were excluded. Adults with documented SLE (fulfilling the ARA criteria (Tan et al. 1982, Arthritis Rheum. 25(11): 1271-7)) were recruited from the Rheumatology clinic at the Hospital of the University of Pennsylvania. Blood draws from SLE patients receiving steroids were performed prior to their first morning dose. T1D patients were recruited from the Rodebaugh Diabetes Center at the Hospital of the University of Pennsylvania. Subjects were included if they had a clinical history compatible with autoimmune T1D, defined by insulin-dependence, the absence of obesity, and an age of onset <40 years or >40 years together with elevated levels of autoantibodies to GAD65. Subjects meeting these criteria but presently receiving immunosuppression drugs to support a kidney, pancreas, or islet cell transplant were excluded. The study protocol was approved by the Institutional Review Board of the University of Pennsylvania and all subjects gave their written informed consent to participate.

Statistical Analysis

Group comparisons were analyzed via one-way ANOVA followed by two-tailed Student's t-test. Correlation analyses were performed by calculating Spearman's rank correlation coefficients. Categorical data (gender, race) comparisons were analyzed using Fisher's exact test. For all tests a p value of ≤1.05 was considered significant.

Example 1

Recombination Sequence (RS) Rearrangement Occurs Late During Light Chain Gene Rearrangement The results presented herein demonstrate that recombination sequence (RS) rearrangement occurs late during light chain gene rearrangement. This is consistent with its role in light chain receptor editing. This result is further supported by higher levels of RS rearrangement in λ B cells than in κ expressing B cells and therefore supports the model of ordered progression of light chain rearrangements starting with κ, proceeding to RS and λ rearrangements.

The following examples describe a quantitative assay for RS rearrangement that can be used to estimate levels of antibody light chain receptor editing in various B cell populations. RS rearrangement is a recombination of a non-coding gene segment in the κ antibody light chain locus. It was observed that RS rearrangement levels are highest in the most highly edited B cells and inappropriately low in autoimmune mouse models of systemic lupus erythematosus (SLE) and type 1 diabetes (T1D), including those without overt disease. Low RS rearrangement levels were also observed in human subjects with SLE or T1D.

Light chain rearrangement proceeds in an ordered fashion as B cells develop in the bone marrow, with κ genes recombining first, followed by rearrangement of the Recombining Sequence and 2 (Lewis et al., 1982, Cell 30(3):807-816; Muller et al., 1988, J Exp Med. 168(6):2131-2137). The Recombining Sequence (known as the Kappa Deleting Element (KDE) in humans, hereafter RS) is a non-coding gene segment located 25 kb downstream of Cκ in the κ locus that is rearranged during continued Ig light chain gene rearrangement (Durdik et al., 1984, Nature 307(5953):749-752; Siminovitch et al., 1985, Nature 316(6025):260-262).

Due to the unique structure of the κ locus, primary Vκ-Jκ rearrangements that are non-functional or autoreactive can be replaced via "leap-frogging" recombination of un-rearranged upstream Vκ- and downstream Jκ-gene segments to form new κ light chains (FIG. 1). Additional rearrangement attempts can be made through recombination at the second κ allele or at λ. Recombination of RS to upstream Vκ-gene segments or a recombination signal sequence (RSS) within the Jκ-Cκ intron results in the deletion or inversion of Cκ and functional inactivation the κ locus (FIG. 1). Because RS rearrangements do not encode any functional proteins, monitoring RS rearrangement provides a specificity-independent means of measuring repeated rearrangement attempts at κ (receptor editing).

It is believed that RS recombination serves to promote λ rearrangement by either repressing κ rearrangement or activating the λ locus (Muller et al., 1988, J Exp Med. 168(6): 2131-2137). This is because light chain rearrangement proceeds in an ordered fashion as B cells develop in the bone marrow, with κ genes recombining first, followed by rearrangement of the Recombining Sequence and λ (Lewis et al., 1982, Cell 30(3):807-816; Muller et al., 1988, J Exp Med. 168(6):2131-2137). However, λ-expressing B cells can form without undergoing RS rearrangement, indicating that RS is not required for the production of λ (Zou et al., 1993, EMBO J. 12(3):811-20).

Current clinical assays that evaluate B lymphocyte tolerance focus on serum autoantibodies, which are products of mature B cells. Because secreted autoantibodies are an end-product rather than an intermediate, they do not distinguish between autoimmunity that arose during primary B cell maturation or later due to events such as somatic mutation. The distinction is important because a defect in primary B cell tolerance may predict disease development. Furthermore, diseases occurring as a result of a primary B cell tolerance defect may be associated with resistance to B cell targeted therapy because the primary repertoire is predicted to rapidly repopulate with autoreactive cells if B cell reconstitution is allowed to proceed.

Assay for Estimating Levels of Receptor Editing

The experiments focused on RS rearrangement as an assay for receptor editing because RS rearrangement is known to accompany extensive light chain rearrangement during primary B cell maturation (Klein et al., 2005, J Immunol 174 (1):367-375) and the major RS rearrangement products are defined and share a common DNA sequence. Most importantly, RS rearrangements do not encode a functional protein, and therefore are independent of antibody specificity, making their measurement potentially applicable to any disease in which B cells play a pathogenic role. By combining a quantitative PCR assay for RS rearrangement frequency with cell sorting, receptor editing can be analyzed in different B cell subsets (FIG. 2).

The most abundant class of RS rearrangements, which are Vκ to RS in mice and IRS to RS in humans was analyzed (Retter et al., 1998, J Exp Med. 188(7):1231-1238; Brauninger et al., 2001, Eur J Immunol. 31(12):3631-7). For the mouse studies, a degenerate Vκ primer was used for RS rearrangement measurements (Schlissel et al., 1989, Cell 58(5):1001-1007). Murine Vκ-RS rearrangements were quantified as fold difference relative to IgM$^+$, κ$^+$ spleen DNA from B6 mice (the spleen contains a mixture of different VκS). Fold differences were used rather than absolute frequencies based upon a cloned single Vκ-RS rearrangement in order to avoid confounds caused by differing amplification efficiencies for different Vκ genes. For the human studies, iRS to RS rearrangements were quantified relative to an absolute standard consisting of a cloned iRS-RS rearrangement that was serially diluted in fibroblast DNA. Log-linear amplification was observed over the range of 0.7-200% RS rearrangements per cell genome (FIG. 3). 200% corresponds to having two RS rearrangements, one on each κ allele. Typical RS frequency measurements were observed to fall within this log-linear range.

Figure 5A:
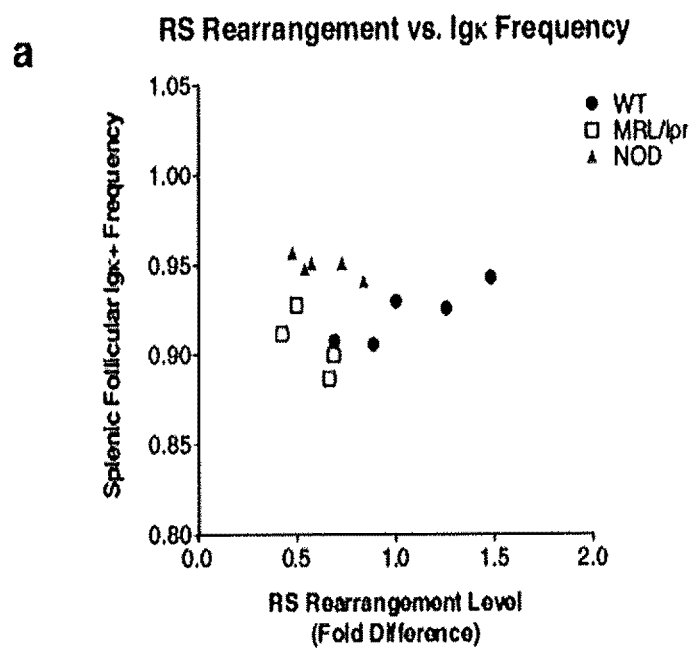
FIGS. 5A and 5B, is a series of images demonstrating that RS rearrangement levels amongst κ+ B cells are independent of Igκ/Igλ ratios.
Figure 5B:
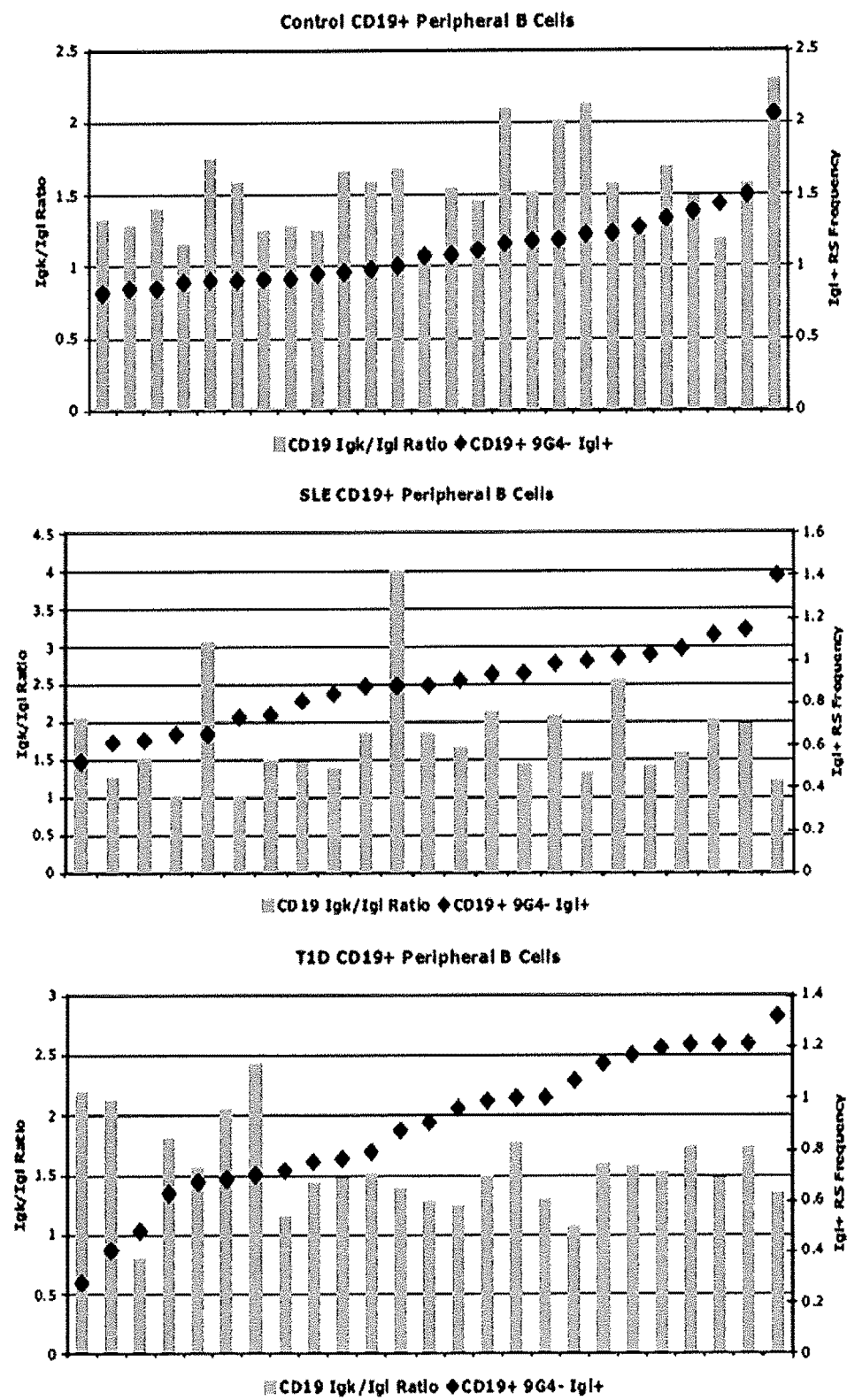

The correlation between RS rearrangement and extensive light chain rearrangement has been established (Durdik et al., 1984, Nature 307(5953):749-752; Siminovitch et al., 1985, Nature 316(6025):260-262; Retter et al., 1998, J Exp Med. 188(7):1231-1238; Brauninger et al., 2001, Eur J Immunol. 31(12):3631-7; Moore et al., 1985, Proc Natl Acad Sci USA. 82(18):6211-5; Dunda et al., 1997, J Immunol 159(9):4362-4366). Consistent with earlier reports, RS rearrangement was observed to be increased by 8-fold amongst λ$^+$ murine IgM$^+$ B cells compared to κ$^+$ cells (FIG. 4). Amongst CD19$^+$ human B cells, 16% of κ$^+$ B cells carried an RS rearrangement and the frequency of RS rearrangements amongst λ$^+$ B cells was greater than 100%, indicating that some λ$^+$ B cells have rearranged to RS on both κ alleles. Given the high levels of RS rearrangement found in B cells, RS analysis was performed separately in κ$^+$ or λ$^+$ cells to limit variability that could be introduced by differing κ/λ ratios, RS rearrangement frequency is not simply a reflection of the proportion of λ B cells. RS rearrangement levels in κ$^+$ or λ$^+$ cells varied independently from overall κ/λ ratios (FIG. 5). This is not surprising in mice, where the κ/λ ratio in peripheral B cells is too high to shift much, but in humans, where there are larger inter-individual differences in κ/λ, there also does not appear to be a correlation between RS rearrangement frequency in κ$^+$ or λ$^+$ cells and the κ/λ ratio. However, RS rearrangement frequencies are correlated in κ and λ-expressing B cells within single individuals. (This intra-individual correlation and the concept of an RS set point is described more fully elsewhere herein with respect to the analysis of human subjects).

Figure 6A:
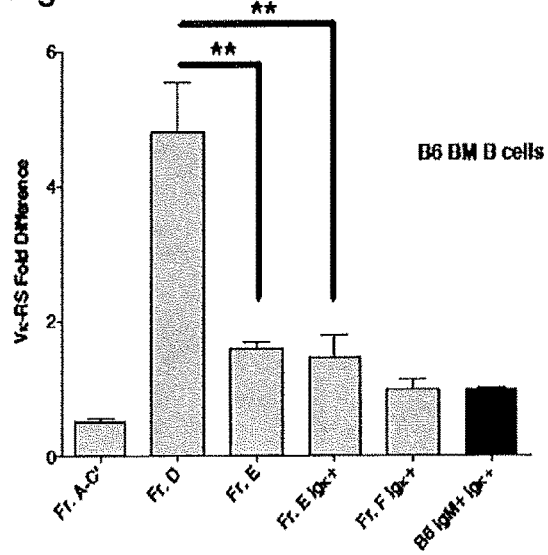
FIGS. 6A through 6C, is a series of images demonstrating that RS rearrangement levels are highest in late pre-B cells.
Figure 6B:
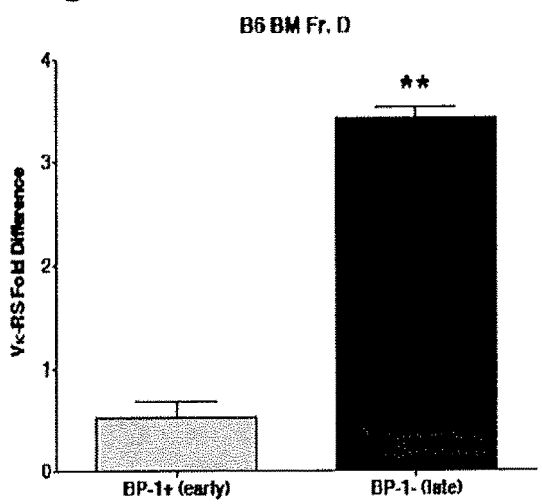

RS Rearrangement Levels Vary Between Developmental and Functional B Cell Subsets in Mice The following experiments were designed to determine whether RS rearrangement, as a marker of ongoing antibody light chain rearrangement, occurs at the time of late κ or λ rearrangement. It was observed that the highest level of RS rearrangement was found among bone marrow fraction D cells (small pre-B II cells (Hardy et al., 1991, J Exp Med., 173(5):1213-1225), hereafter Fr. D), which are cytoplasmic Igμ$^+$, but no longer expressing surrogate light chain and have re-expressed the Rag1 and Rag2 proteins for light chain gene rearrangement (FIG. 6A) (Hardy et al., 1991, J Exp Med., 173(5):1213-1225). Further subsetting within Fr, D based upon BP-1 expression, revealed that the majority of RS rearrangements most likely occurred towards the end of this period (FIG. 6B).

In the subsequent developmental subset, Fr. E (newly formed IgM$^+$ immature B cells), Vκ-RS rearrangement levels were reduced by 3-fold and closer to those of mature, circulating B cells (Fr. F). Without wishing to be bound by any particular theory, it is believed that the difference in Vκ-RS rearrangement levels between Fr. D cells and κ$^+$ Fr. E cells is due to the inclusion of pre-B cells undergoing or completing λ rearrangement within Fr. D. However, RS levels in total IgM$^+$ Fr. E cells were similar to κ$^+$ Fr. E cells, suggesting that exclusion of λ$^+$ cells from Fr. E cannot fully account for the decrease. Death of RS$^+$ cells or their rapid exit from the bone marrow to a peripheral pool may contribute to the decrease in RS rearrangement levels in Fr. E relative to Fr, D.

Example 2

RS Rearrangement Levels Differ Between Autoreactive and Non-Autoreactive B Cells The results presented herein demonstrate that RS rearrangement frequencies are higher in B cells from self-tolerant mice that express an autoreactive heavy chain (56R). This finding suggests that light chain rearrangement is increased in autoreactive B cells.

The experiments were designed to determine how or if RS rearrangement frequency is linked to autoreactivity. It is believed that editing is driven either by the potential of the antibody heavy light chain pair to form autoantibodies (active model), or it occurs without regard for receptor specificity (passive model). To distinguish between active and passive editing, RS rearrangement frequencies were analyzed in the 56R mouse model, where the B cell repertoire has been characterized extensively (Li et al., 2001, Immunity 15(6):947-957; Sekiguchi et al., 2006, J Immunol 176(11):6879-6887; Liu et al., 2007, J Immunol 179(2):1340-1352). This mouse carries a site-directed transgene encoding an anti-DNA specific immunoglobulin heavy chain. Using B6.56R$^{+/-}$ mice, one can distinguish B cells with an autoreactive Ig heavy chain (IgM$^{a+}$, mostly 56R expressing) and endogenous (IgM$^{b+}$, 56R$^-$) B cells (FIG. 7A). 56R-expressing B cells have a restricted light chain repertoire consisting of only a handful of light chains, termed editors, because they modify or reduce DNA binding (Li et al., 2001, Immunity 15(6):947-957; Sekiguchi et al., 2006, J Immunol 176(11):6879-6887; Liu et al., 2007, J Immunol 179(2):1340-1352). This restriction in light chain usage could arise if 56R B cells with non-editor light chains were counter-selected or if B cells with non-editor light chains were subjected to more receptor editing. The former alternative predicts equal levels of RS rearrangement in IgM$^{a+}$ and IgM$^{b+}$ cells, whereas the latter predicts higher levels of RS rearrangement in IgM$^{a+}$ B cells. Consistent with an active model of receptor editing, a two-fold increase in RS rearrangement levels was observed in IgM$^{a+}$ B cells (FIG. 7B).

Example 3

Mouse Strains Prone to Autoimmunity Display Lower Levels of RS Rearrangement

The results presented herein demonstrate that RS rearrangement frequencies are decreased in two different mouse models of autoimmunity, MRL/lpr and NOD. The low levels of RS rearrangement are also present in the control strains MRL/MpJ and NOR, which were not observed to developed autoimmunity. These results suggest that RS rearrangement frequency may predict disease development rather than arising as a consequence of disease.

Figure 8A:
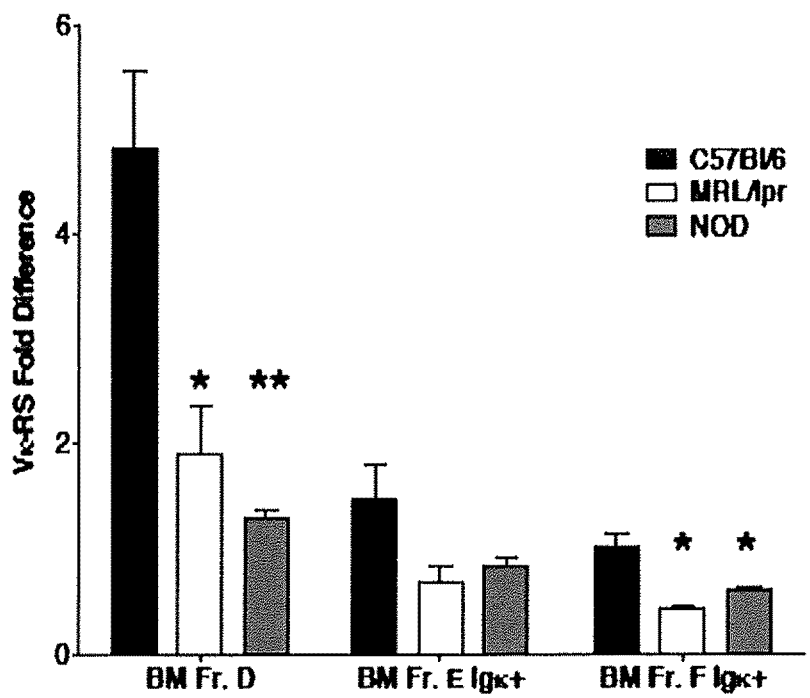
FIGS. 8A and 8B, is a series of images demonstrating that autoimmune-prone mouse strains display reduced levels of RS rearrangement.
Figure 8B:
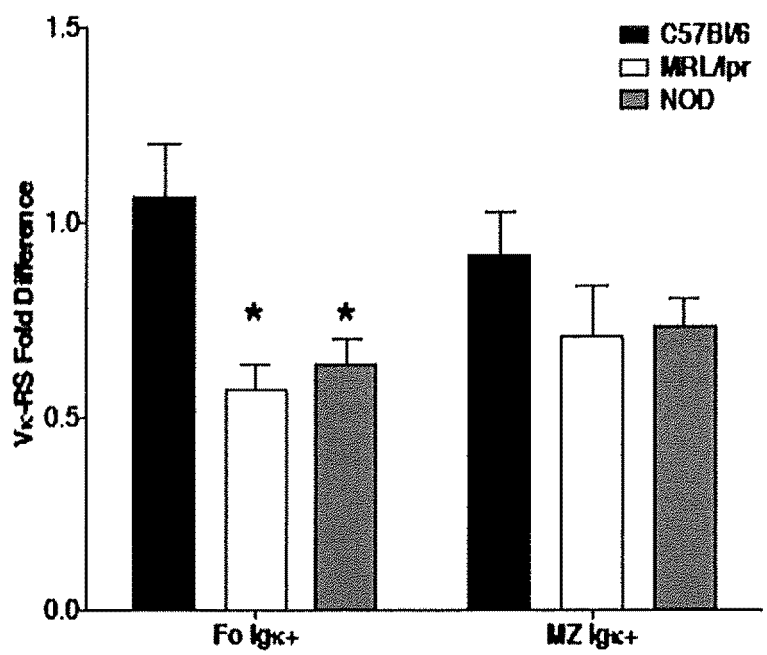

The experiments discussed elsewhere herein establish the developmental timing of RS rearrangement and demonstrate a positive correlation between RS rearrangement frequency and an autoreactive antibody heavy chain in inbred mice. To determine if RS rearrangement is altered in the context of autoimmunity, RS rearrangement frequency was measured in two different mouse models of autoimmune disease, MRL/lpr mice as a model of SLE and non-obese diabetic mice (NOD) mice as a model of T1D. Decreases in RS rearrangement levels were observed among Fr. D cells of both MRL/lpr (2.5-fold reduction, p<0.05) and NOD mice (3.7-fold reduction, p<0.01), when compared to C57Bl/6 mice (FIG. 8A). Interestingly, fewer RS rearrangements were also observed among Fr. E cells in both MRL/lpr and NOD mice relative to C57Bl/6 mice. This decrease was evident in the mature recirculating B cells of the bone marrow (Fr. F) as well, implying that unedited or minimally edited cells persisted through development. Measurement of RS levels in splenic B cell subsets further substantiated this finding (FIG. 8B).

Figure 9A:
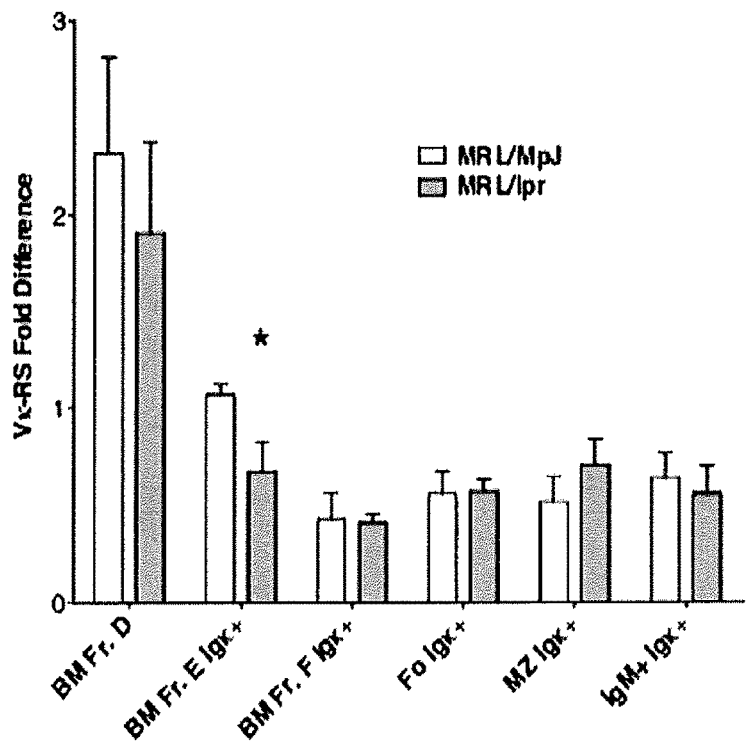
FIGS. 9A and 9B, is a series of images depicting RS rearrangement levels in MRL/MpJ and NOR strains.
Figure 9B:
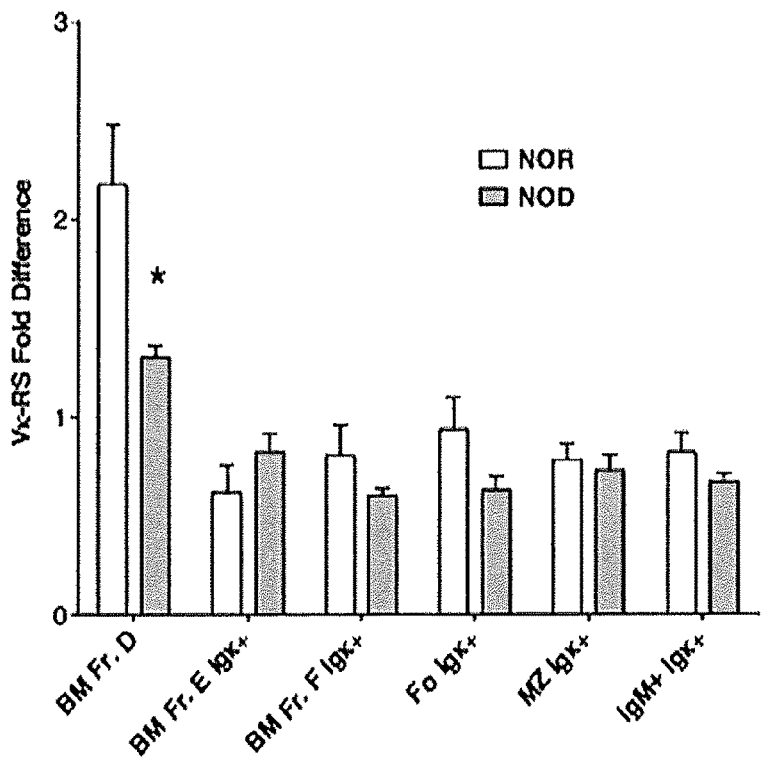
Figure 10B:
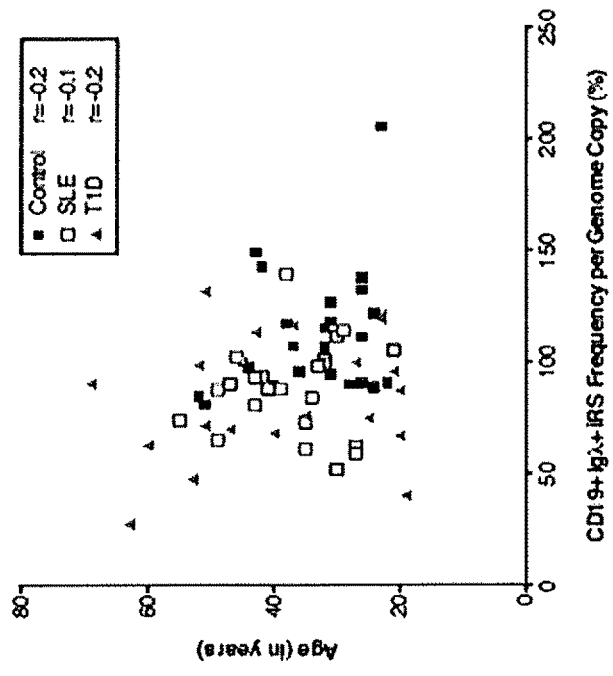
FIGS. 10A through 10D, is a series of images demonstrating that RS rearrangement levels do not correlate with patient group demographics.
Figure 10A:
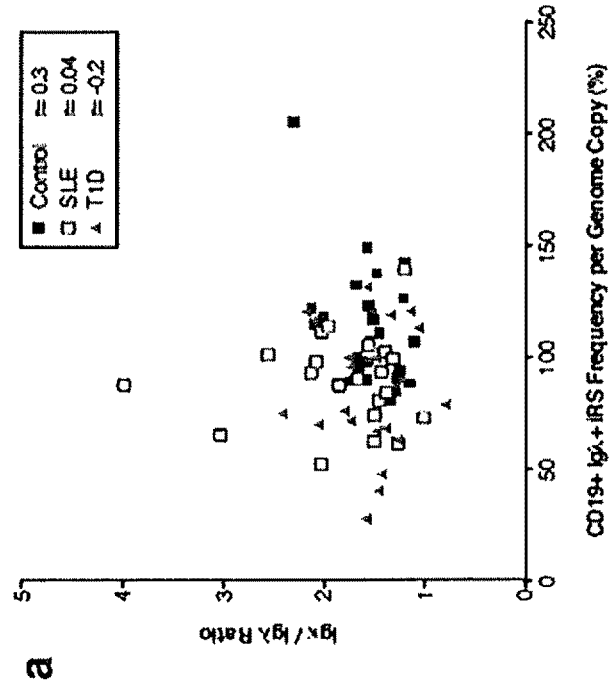
Figure 10D:
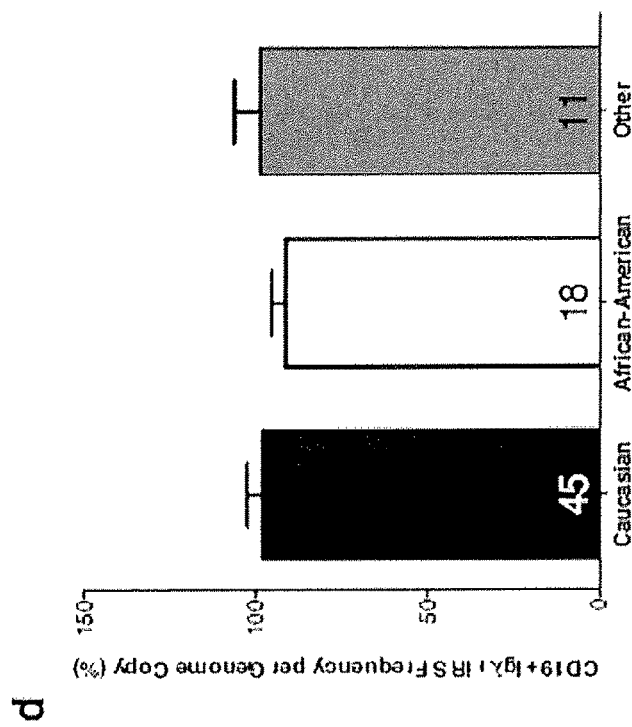
Figure 10C:
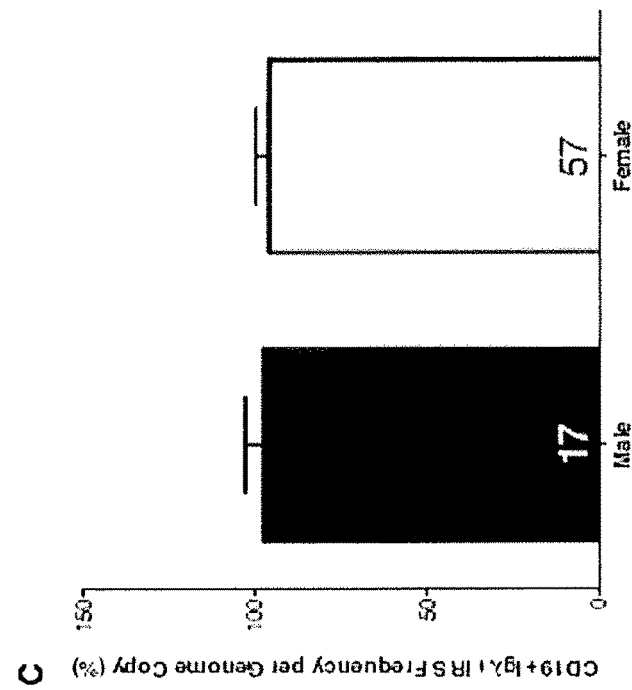

To determine if the lower levels of Vκ-RS rearrangements detected in MRL/lpr and NOD mice are attributable to strain effects, rather than as a consequence of an autoimmune state, RS levels were measured in MRL/MpJ mice, which share the same genetic background as MRL/lpr mice but lack the Fas mutation that is responsible for their lymphocytosis and accelerated systemic autoimmunity. Similarly, NOD mice were compared to NOR mice, which share the same diabetogenic WIC haplotype (H2$^{g7}$) with NOD mice but are insulitis-resistant and do not develop T1D (Prochazka et al., 1992, Diabetes 41(1):98-106) (FIG. 9). These "control" strains share the propensity to develop autoimmunity with MRL/lpr and NOD mice, but do so at a much slower pace. The control mice were analyzed at 3 months of age, a time at which autoimmunity is not yet evident. Although RS rearrangement levels were slightly increased among some bone marrow B cell subsets in the control mouse strains, levels in mature B cells were comparable in MRL/MpJ and NOR mice to their more autoimmune counterparts. The low frequency of RS rearrangement in MRL/MpJ and NOR mice suggests that a reduced level of receptor editing predisposes towards the development of autoimmunity rather than arising as a consequence of autoimmune disease.

Example 4

RS Rearrangement Levels are Lower in Human SLE and T1D

The results presented herein demonstrate that RS rearrangement frequencies are decreased in approximately 30% of patients with SLE and 30% of patients T1D and in fewer than 5% of healthy control subjects. These findings suggest that a significant fraction of SLE and T1D patients harbor defects in central B cell tolerance.

To further investigate the level of receptor editing in the context of defective tolerance, RS rearrangement levels in peripheral B cells from human subjects with established disease (SLE or T1D) were compared to healthy control subjects. For this analysis, 26 control subjects, 24 patients with SLE and 25 patients with T1D were evaluated. Demographic features of the subject groups were compared and no significant differences were observed between control and SLE groups with respect to age, gender, and race. However, the T1D group contained a larger proportion of men and Caucasians than the control and SLE groups (Table 1). Nonetheless, RS frequencies were not correlated with subject age, gender, or race (FIG. 10).

TABLE 1

|  | Control | SLE | T1D |
|---|---|---|---|
| Number of subjects | 26 | 24 | 25 |
| Average Age (years) | 33.8 (22-52) | 37.3 (21-55) | 38.5 (19-69) |
| % Female | 0.88 | 0.88 | 0.56 |

TABLE 1-continued

|  | Control | SLE | T1D |
|---|---|---|---|
| % Caucasian | 0.58 | 0.29 | 0.92 |
| % African-American | 0.27 | 0.42 | 0.04 |
| % Other | 0.15 | 0.29 | 0.04 |
| Average κ/λRatio (CD19+) | 1.5 (1.1-2.3) | 1.8 (1.0-4.0) | 1.6 (0.8-2.4) |
| Average B Cell Fraction (CD19+) | 0.11 (0.05-0.19) | 0.10 (0.01-0.2) | 0.10 (0.02-0.19) |
| Average Absolute B Cell Count (per μl)* | 221 ± 126 | 176 ± 163 | 190 ± 107 |

Figures 11A, 11B, 11C:
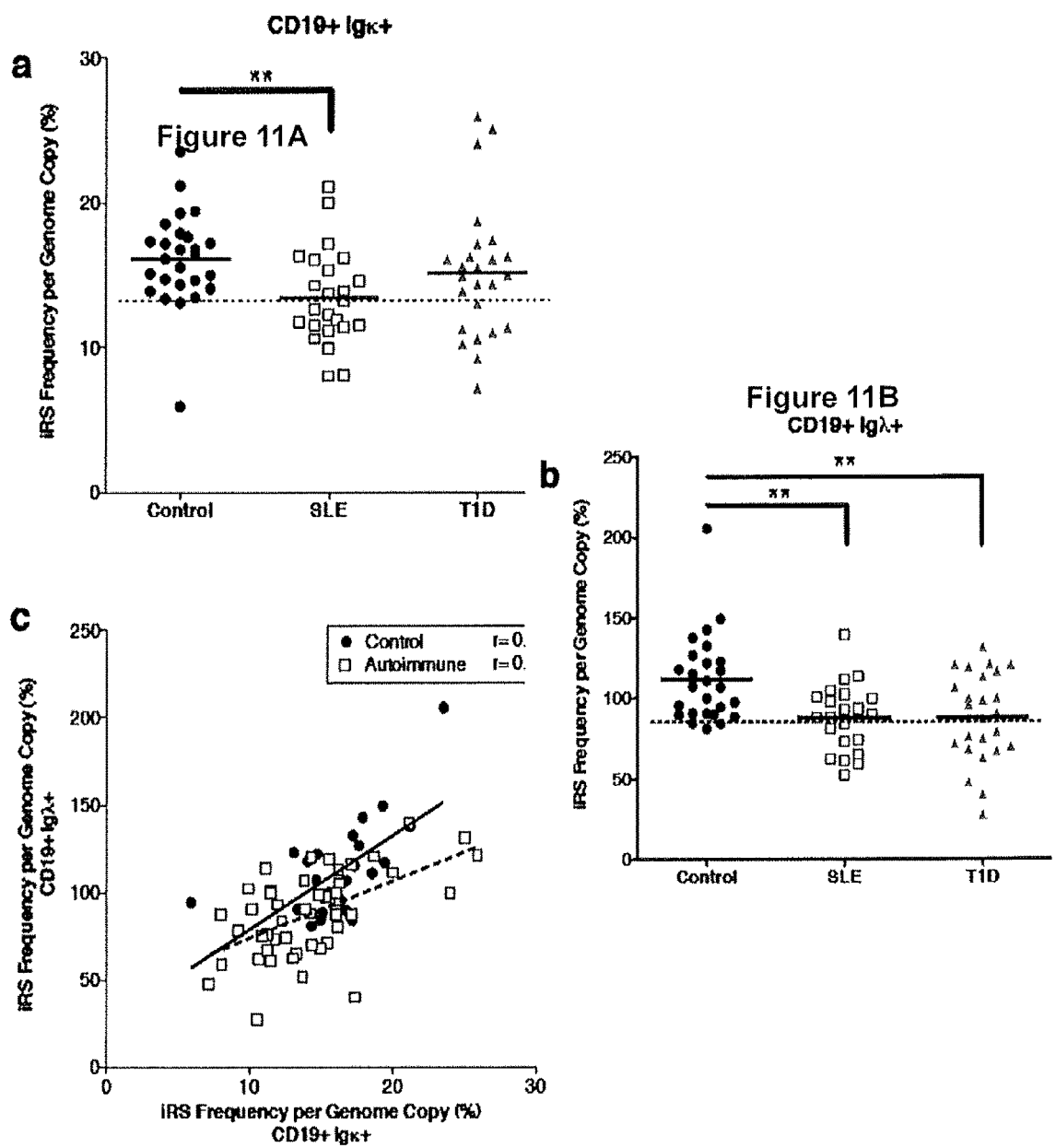
FIG. 11A through FIG. 11C, is a series of images indicating that RS rearrangement levels are lower amongst SLE and T1D patients.

Among CD19+ κ+ B cells, RS rearrangement frequencies from SLE patients were lower on average compared to levels from healthy controls (FIG. 11A, p<0.01). The RS rearrangement frequency in κ+ B cells from T1D was not significantly decreased compared to control subjects. In CD19+ λ+ B cells RS levels were lower in both SLE and T1D patients compared to control subjects (FIG. 11B, p<0.01). These results resemble those from the autoimmune mouse models and suggest that lower levels of RS rearrangement may be correlated with disease susceptibility.

Using the $10^{th}$ percentile of the normal population RS rearrangement frequency distribution for κ+ B cells, one can define a lower cut-off of 13% for the RS rearrangement frequency (κRS). Using this cut-off, the fraction of subjects with a low κRS value is 2/26 for the healthy control subjects, 13/24 for SLE and 8/25 for T1D. Using a similar λRS cut-off, 3/26 controls, 9/23 SLE patients and 11/25 T1D patients had low RS levels. Additionally, RS levels were low in both κ+ and λ+ B cells in 7/23 SLE and 7/25 T1D patients, indicating that subjects with low κRS levels tended to also have low λRS levels. Indeed, Spearman correlations between the κRS and λRS measurements were significant in both healthy subjects and patients with autoimmune disease (r=0.54, p<0.01 and r=0.52, p<0.01, respectively; FIG. 11C). Additionally, linear regression analysis revealed a lower degree of RS rearrangement in λ+ cells relative to levels in κ+ in patients with autoimmune disease compared to healthy controls. Together these findings suggest that some SLE and T1D patients have lower editing set points than those of most healthy individuals.

Example 5

RS Rearrangement Set-Point

The results presented herein demonstrate that RS rearrangement frequencies are correlated in κ and λ-expressing B cells in individuals, suggesting that each individual may have an RS rearrangement "set-point." The results presented herein demonstrate the successful development of an assay useful for monitoring B cell tolerance and selection stringency. This assay can inform the choice of B cell targeted therapy for autoimmune disease. This contention is based upon the idea that individual patient's with SLE and T1D have different tolerance defects (Harley et al., 2008, Nat Genet. 40(2):204-10; Florez et al., 2003, Annu Rev Genomics Hum Genet, 4:257-91). Previous assays that monitor B cell tolerance are problematic because they tend to measure relatively late events such as autoantibody production, rather than the pathways that B cells take on their way to becoming autoimmune.

The RS rearrangement assay presented herein takes two days to perform and provides insights into central (early) B cell tolerance. Furthermore, it can be combined with immunophenotyping to analyze editing levels in different peripheral B cell subsets. If the assay is modified to use PCR-based L chain rearrangement calibrators instead of flow cytometry, the assay can be completed within one day. As such, the assays described herein are useful for monitoring and staging defects in B cell tolerance.

The RS rearrangement assay described elsewhere herein gives an estimate of the overall level of light chain rearrangement in a defined population of B cells. The correlation between RS level and the light chain rearrangement level is based on earlier studies documenting that 10 to 15% of murine splenic B cells had undergone RS recombination, while virtually all λ+ splenic B cells harbored an RS rearrangement (Retter et al., 1998, J Exp Med. 188(7):1231-1238; Moore et al., 1985, Proc Natl Acad Sci USA. 82(18): 6211-5; Dunda et al., 1997, J Immunol 159(9):4362-4366). Similarly, studies of single human B cells and acute lymphoblastoid leukemia cell lines demonstrated that cells expressing λ harbored more RS rearrangements than ones that expressed κ (Brauninger et al., 2001, Eur J Immunol. 31(12): 3631-7; van der Burg et al., 2002, Leukemia 16(8):1448-1453). Furthermore, λ B cells took approximately 24 hours longer to label with BrdU than B cells with κ rearrangements (Arakawa et al., 1996, Int Immunol. 8(1):91-9). Finally, studies in B cell leukemia cell lines subjected to Bcr-Abl tyrosine kinase blockade exhibited temporally ordered light chain rearrangements: κ followed by RS followed by λ (Klein et al., 2005, J Immunol 174(1):367-375). The results presented here are consistent with all of these previous studies: RS rearrangement frequencies were higher in λ+ B cells than in κ+ B cells and were most frequent in late pre-B cells (Fr.D). Every other B cell subset, including Fr. E (which is where surface antibody is first detected) and more mature splenic B cells, exhibited lower RS levels. As RS rearrangements are non-revertible, these findings suggest that receptor editing fails to salvage some of the most highly edited B cells from clonal deletion. An increased RS rearrangement frequency was also observed in B cells with autoreactive H chains. Because RS rearrangements do not encode a protein that can be selected, this result indicates that the presence of an autoreactive H chain increases the likelihood of ongoing light chain rearrangement and is consistent with other reports favoring an active, autoantigen-driven model of receptor editing (Hertz et al., 1997, Immunity 6(4):429-436; Schram et al., 2008, J Immunol 180(7):4728-4741). These findings are consistent with earlier work in autoantibody transgenic mice, showing that some highly edited B cells are auto/multi-reactive (Liu et al., 2005, J Immunol 175(8):5067-5076). Without wishing to be bound by any particular theory, it is believed that the loss of B cells with more RS rearrangements could also reflect the failure to produce a functional antibody.

The results presented herein demonstrate decreases in RS rearrangement frequency occur in mouse models of SLE and T1D. Both MRL/lpr and NOD mice exhibited lower RS levels compared to wild-type C57Bl/6 mice. The finding of lower editing levels in MRL/lpr mice is consistent with recent work demonstrating decreased receptor editing in response to a ubiquitous membrane bound self antigen in transgenic MRL/lpr mice (Lamoureux et al., 2007, J Exp Med. 204(12):2853-2864). The finding of decreased RS rearrangement in NOD mice is at odds with a previous report in which editing was measured using a membrane bound facultative self-antigen (HEL) (Silveira et al., 2004, J. Immunol. 172(8):5086-5094). The RS assay, however, does not focus on one kind of self-antigen.

Although both MRL/lpr (Watanabe-Fukunaga et al., 1992, Nature 356(6367)314-317) and NOD (Kishimoto et al., 2001, Nat Immunol. 2(11):1025-31) strains harbor previously characterized defects in apoptosis, lower RS levels were not linked to these defects per se, as B cells from MRL/MpJ and NOR mice (both with intact apoptosis) also exhibited lower RS levels. In the case of MRL/lpr mice, the additional defect conferred by the lpr mutation (Watanabe-Fukunaga et al., 1992, Nature 356(6367):314-317) may lead to less stringent selection of minimally edited immature B cells. Similarly, the finding of low RS rearrangement levels in both the NOD and NOR strains suggests that a second tolerance defect present only in NOD mice is required for development of diabetes. However, the genetic backgrounds of these control strains predispose them to develop autoimmunity. Despite having an intact Fas gene, MRL/MpJ mice spontaneously develop autoimmunity including pancreatitis (Kanno et al., 1992, Clin Exp Immunol. 89(1):68-73) and glomerulonephritis (Hewicker et al, 1990, Z Versuchstierkd. 33(4):149-56), but the disease is milder and occurs later in life. NOR/LtJ mice share the diabetogenic $H2^{g7}$ haplotype with NOD mice and have altered macrophage and peripheral T cell compartments (Prochazka et al., 1992, Diabetes 41(1):98-106). All of the mice used for these experiments were 3 months of age, which is at a time that precedes disease development in NOR and MRL/MpJ mice. Together these findings suggest that decreased RS rearrangement levels in these mice reflect an altered propensity to develop autoimmunity.

In humans, lower RS rearrangement levels were also detected in both SLE and T1D patients compared to healthy control subjects. The decrease was most apparent in $\lambda^+$ B cells, but the level of RS rearrangement was correlated in $\kappa^+$ and $\lambda^+$ B cells in individual patients. The levels were not proportional to the $\kappa/\lambda$ ratio or to the fraction of B cells in the blood. These findings have theoretical and practical implications. The theoretical implication is that individuals may have different RS rearrangement "set-points." The set-points tend to be lower in T1D and SLE than in healthy subjects, but overlap to some degree. RS levels in different peripheral B cell subsets can be directly measured to determine if the differences can be correlated with B cell selection checkpoints or if, in a fashion similar to the mouse models, different subsets may show correlated RS levels. Prior to the present disclosure, selection checkpoints have been monitored by single cell antibody cloning and expression studies. However, use of the RS rearrangement assay described herein provides a method to more easily define B cell tolerance checkpoints in individual patients with autoimmune disease. The practical implication of having correlated RS rearrangement frequencies in $\kappa^+$ and $\lambda^+$ B cells is that it may be possible to measure RS rearrangement frequency in whole blood rather than in sorted B cell subsets and then to correct the measurement for the B cell fraction and $\kappa/\lambda$ ratio.

Given the concordance of RS rearrangement levels in T1D and SLE, it is believed that upstream genetic defects could decrease receptor editing in both disorders. One candidate is PTPN22 (protein tyrosine phosphatase non-receptor 22, also known as Lyp). PTPN22 is a lymphoid specific phosphatase that suppresses T cell activation. A variant of PTPN22 (R620W) is common in both SLE and T1D (Bottini et al., 2004, Nat Genet, 36(4):337-8; Lee et al, 2007, Rheumatology (Oxford). 46(1):49-56) and has a more active phosphatase in the setting of T1D (yang et al., 2005, Nat Genet. 37(12):1317-9). Without wishing to be bound by any particular theory, it is believed that there could be an increased BCR signaling threshold due to PTPN22 R620W that would result in decreased receptor editing. Other potential candidates include RAG or molecules that influence the intracellular localization or expression of RAG such as the nuclear importin KPNA1 (Glinsky, G. V., 2008, Cell Cycle. 7(16). [Epub ahead of print]), interferon regulatory factor 4 (Johnson et al., 2008, Immunity 28(3):335-45), or the transcription factor Foxo1 (Amin et al., 2008, Nat Immunol, 9(6):613-22; Herzog et al., 2008, Nat Immunol. 9(6):623-31). Because RS rearrangement frequency corresponds to a phenotype rather than a heritable genetic alteration, there could be several different defects, each of which could contribute independently to a low RS frequency.

Without wishing to be bound by any particular theory, it is believed that individuals with low RS levels (including a small subset of currently healthy subjects) are at increased risk of developing autoimmunity. In this regard, the prospective analysis of first-degree relatives of patients with autoimmunity would be especially informative.

Example 6

Evaluation of Clonal Expansion and L Chain Rearrangement Diversity

Experiments were designed to explore the reasons for having extreme RS rearrangement frequencies. If an expanded clone comprises a high fraction of the B cell compartment, the RS rearrangement frequency may be abnormally high or low, depending upon the RS genotype of the expanded clone. The traditional way of screening for clonal expansion is to use flow cytometry to look for evidence of L chain restriction (skewing away from the normal polyclonal $\kappa/\lambda$ ratio of 60/40). However, in the final form of the assay, flow cytometry is not used. Therefore, experiments were designed to evaluate clonal expansion using the length heterogeneity of the RS PCR products themselves. RS rearrangements in the mouse are known to be variable in length due to enzymatic activity of RAG and NHEJ enzymes (Retter et al., 1998, J Exp Med 188:1231-8). FIG. 12B indicates that RS rearrangements are also variable in length in humans. CD19+ cells were purified from whole blood of a normal subject by flow cytometry and analyzed for iRS rearrangements using primers as in the iRS qPCR assay, but with a fluorescent label on the RS reverse primer. Amplicon sizes were determined by capillary electrophoresis vs. a ROX-labeled ladder on an ABI3100 sequencer. FIG. 12B shows a roughly Gaussian distribution of rearrangement lengths at 1 bp intervals. In the case of clonal expansions, one peak dominates over the others. Alternatively, at limiting amounts of input DNA, independent amplifications yield the same sized peak (or peaks) repeatedly.

RS Spectratyping Analysis for Clonal Expansion

One reason for obtaining an abnormal RS frequency is if the overall level of L chain rearrangement is abnormal. If this is the case, RS is correlated with V$\kappa$-RS and inversely correlated with V$\kappa$-J$\kappa$1/2. Another reason for abnormal RS frequency is clonal expansion (the presence of many copies of the same B cell), which can occur in lymphoma, when there is an extremely exuberant immune response and in some instances are in patients with lupus. With clonal expansion, the various L chain calibrating assays may be affected by the L chain genotype of the expanded clone. If the clone is small (<1% of B cells), it is unlikely to substantially skew the results, but if the clone is large (>20%), the results are skewed. To determine the sensitivity the assay for detecting clonal expansion, DNA from a lymphoma cell line is titrated with one RS rearrangement into polyclonal B cell DNA from a normal subject and RS rearrangements are analyzed by spectratyping in duplicate at moderately high input DNA concentrations (~100 ng/reaction). At this DNA concentration, a polyclonal B cell repertoire yields an approximately Gaussian distribution of peaks. If a significant clonal expansion is present, one of the peaks (corresponding in size to the RS rearrangement in the lymphoma) stands out above the background (the monoclonal "spike"). If the spike is present in both amplifications and exhibits at least twice the fluorescence intensity of the highest peak from the polyclonal distribution, the sample meets criteria for clonal expansion. The target level of clonal expansion to be detected by this assay is 1%. If this assay meets that target, the samples with abnormally low or high RS levels for clonal expansion are evaluated using the RS spectratyping assay. This allows for determining if SLE patients have higher levels of significant B cell clonal expansion that may be skewing the RS assay. It will also allow for determining what fraction of the abnormal RS readings is attributable to clonal expansion. Approximately 30 low RS, 30 normal RS (to match the number of low RS) and fewer than 5 high RS samples can be analyzed. If the RS spectratyping assay does not meet the 1% target, conventional CDR3 spectratyping of H chain rearrangements can be used to detect clonal expansions (FIGS. 12C, 12D). H chain spectratyping is performed routinely in the clinical laboratory for lymphoma evaluation. Specificity of the RS spectratyping PCR is confirmed by DNA sequence analysis.

FIG. 12D is a summary of experiments conducted to examine VH81X-JH4 rearrangements. Briefly, VH81X-JH4 rearrangements were amplified from splenocyte DNA of a single B6.56R mouse and a single B6 mouse. B6.56R mice have an anti-dsDNA antibody heavy chain transgene and are used as a mouse model to study how disease-associated autoantibodies are regulated. Spectratypes plot fluorescence intensity (y-axis) as a function of product size in by (x-axis). The spectratypes from three independent PCR amplifications of B6.56R mice look very similar to one another, consistent with oligoclonal expansion. Based on their length diversity, a similar analysis can be performed with RS spectratyping to evaluate the sample for clonal expansion. This analysis is relevant because clonal expansions of B cells can be found in certain autoimmune diseases including lupus and Sjogren's syndrome.

Example 7

Light Chain Rearrangement Correlates with Immunophenotypic Changes in Naive B Cells and IgM Autoantibody Production Defects that occur during early B cell development are important because a high fraction of the primary B cell repertoire is autoreactive (Wardemann et al., 2003, Science 301: 1374-1377). If early tolerance checkpoints fail, autoreactive B cells rapidly re-form and accumulate in more mature B cell stages (downstream of the defect) (Cines et al., 2009, Blood 113(26):6511-21). This could account for some of the recent failures of B cell depletion therapy in lupus and suggest other treatment strategies.

The experiments discussed herein relate to measuring non-productive antibody gene rearrangements, which take place during early B cell development in the bone marrow. Early B cell development can be studied in mature B cells because traces of gene rearrangements remain in the DNA as B cells mature. Using the RS rearrangement assay discussed elsewhere herein, it has been observed that approximately 30% of patients with lupus have low levels of antibody light chain gene rearrangement, suggestive of an antibody receptor editing defect. It is believed that RS rearrangement assays can be used for read-outs of early B cell development and can be used to assess whether abnormalities in RS rearrangement correlate with phenotypic changes and/or autoantibody production in naive B cells in lupus patients.

Frequency of Non-Functional Antibody Light Chain Gene Rearrangements

Experiments have been designed to evaluate pre-B cell development in lupus. The extent of antibody light (L) chain gene rearrangement can be monitored using methods discussed elsewhere herein, for example, using quantitative PCR for detecting RS deletion in peripheral B cells. RS deletion in peripheral B cells from lupus patients is compare with peripheral B cells from healthy controls. RS is a non-functional rearrangement that accompanies extensive kappa or lambda L chain rearrangement.

In these experiments, early B cell defects in patients with SLE and demographically matched healthy controls are evaluated. Preferably, SLE patients are ANA+ and fulfill ACR criteria (Tan et al., 1982, Arthritis Rheum 25:1271-1277; Griffiths et al., 2005, Best Pract Res Clin Rheumatol 19:685-708; Hochberg, 1997, Arthritis Rheum 40:1725).

Subjects with lupus nephritis are recruited in order to increase the chances of studying patients who receive varying treatment regimens. Demographically matched controls are also recruited. Subjects who are pregnant or have cancer, acute or chronic infections, or rheumatologic diseases other than SLE are excluded from the experiments. The following information is collected from the subjects: name, contact information, date and time of sample, age, sex, race, body mass index (Chaiamnuay et al., 2007, J Clin Rheumatol 13:128-133), length of illness, clinical and serologic manifestations of SLE, validated measures of disease activity (SLEDAI-2K (Griffiths et al., 2005, Best Pract Res Clin Rheumatol 19:685-708; Wollaston et al., 2004, J Rheumatol 31:2390-2394; Bertoli et al., 2006, Lupus 15:13-18; Becker-Merok et al., 2006, J Rheumatol 33:1570-1577; Gladman et al., 2002, J Rheumatol 29:288-291)), medications, current state of health. Peripheral blood and serum are collected for complete blood count (CBC), B cell separation and genomic DNA extraction, flow cytometry and serum for B cell activating factor (BAFF, BLyS) levels and autoantibody profiles.

If patients are receiving steroids at the time of sample collection, the AM dose is held until blood is collected for B cell studies and CBC (Fauci, 1975, Transplant Proc 7:37-40; Cupps et al., 1984, J Immunol 132:170-175). All SLE subjects with active disease are studied on two separate occasions at least one month and up to one year apart.

As discussed elsewhere herein, approximately 30% of lupus patients have low levels of RS rearrangement. The RS rearrangement assay discussed elsewhere herein can be applied to a larger number of subjects to refine the RS frequency estimate in SLE and to stratify SLE patients into different groups in order to determine if defects in L chain rearrangement correlate with immunophenotypic changes in naive B cells and IgM autoantibody production. That is, by analyzing the frequency of RS rearrangement, a non-productive rearrangement at the κ locus, the pre-B cell stage of development can be evaluated. RS rearrangement frequencies in B cells and κ+ B cells from lupus patients (n=100) and healthy controls (n=50) are evaluated using the RS rearrangement assay.

By measuring the RS rearrangement frequency in individual SLE patients with active disease at two different time points, it may be possible to determine if therapy and/or disease activity alters the RS rearrangement frequency. In a subset of lupus patients with active disease, RS rearrangement frequency is measured at two separate time points. It is believed that these studies help to refine the estimate of the fraction of lupus patients with low RS rearrangement frequencies and determine if differences in disease activity are associated with differences in the RS rearrangement frequency within individual patients. The results are useful in correlating B cell rearrangement with disease activity in lupus.

In addition, the RS rearrangement assay is useful in determining whether RS rearrangement frequencies are stable in individual lupus patients over time. To that end, it is believed that the most rigorous test of variability in RS, is in lupus patients who have active disease (with SLEDAI-2K scores that are at or above 4 and change by 2 or more between study visits and/or have an alteration in disease activity that triggers a change in therapy). Without wishing to be bound by any particular theory, if RS levels do not vary in individual lupus patients over time, this suggests that RS frequency is not influenced by peripheral selection events or therapy. If RS levels do vary, experiments can be designed to explore whether the shift can be correlated with RS levels in particular peripheral B cell subsets.

Ontogenic Timing of L Chain Rearrangement

The next set of experiments was designed to confirm the ontogenic timing of L chain rearrangement measures in humans and to determine if defects in L chain rearrangement correlate with immunophenotypic changes in naive B cells and IgM autoantibody production. It is hypothesized that subjects with altered antibody rearrangement frequencies have defective early B cell tolerance. Bone marrow B cell subsets of healthy human subjects are analyzed to determine if the highest levels of RS rearrangement occur in the pre-B cell compartment (as was observed in mice, FIGS. 6A, 6B). Experiments were also designed to determine whether subjects with L chain rearrangement profiles exhibit alterations in naive peripheral B cells. Observations for accumulation of autoreactive B cells in the transitional compartment (these are the first B cells to exit the bone marrow, see FIG. 6C), an expansion of cells with an anergic phenotype, alterations in the κ/λ light chain ratio and IgM autoantibody production are recorded. In the alternative, experiments were designed to determine whether shifts in the transitional B cell fraction is due to alterations in the BAFF/BLyS B cell survival pathway.

RS frequencies were measured in different peripheral B cell subsets from lupus patients with low RS levels, with normal RS levels and any "normal" subjects with low RS levels. Based on the data in mice and in healthy humans discussed elsewhere herein, large variations in RS frequency in peripheral B cell subsets are not expected. However, if variations are observed in peripheral B cell subsets in human lupus, this would suggest that B cells with high or low levels of L chain receptor editing are subjected differential peripheral selection in lupus. If this occurs, RS frequencies can be analyzed in the following subsets to further explore the connection between the extent of L chain rearrangement and autoreactivity: IgMbright, CD24++, CD19++ as an ersatz marginal zone cell (Carsetti et al., 2004, Immunol Rev 197: 179-191); CD5+, CD38+, CD27+ as an activated B1-like cell and IgD+, IgM−, CD27− (which have an anergic and autoreactive phenotype in normal individuals, (Duty et al., 2009, J Exp Med 206:139-151)).

Without wishing to be bound by any particular theory, it is believed that early B cells are allowed to proceed through the bone marrow without adequate censoring in subjects with defective central tolerance. It is expect that these B cells will enter the periphery and accumulate, potentially overwhelming peripheral tolerance checkpoints. Thus, experiments were designed to determine if an increased number or fraction of B cells in the transitional compartment (the first B cells to exit the bone marrow as defined above), an expansion of anergic B cells, alterations in the κ/λ light chain ratio and IgM autoantibody production correlate with low RS levels. These studies are performed in equal numbers of lupus patients with and without antibody rearrangement defects (approximately 30 per group, based on the frequency of low RS rearrangement alone). In the patient group with abnormal rearrangements, it is expected that the transitional B cell compartment is increased (>15% of CD19+ lymphocytes). Furthermore, some autoreactive cells may "spill over" into the more mature B cell fractions. Thus, IgM autoantibody production is evaluated (ANA, dsDNA, histone, Sm, RNP, phosphorylcholine and galectin). The Hep2 ANA assay is modified with a FITC labeled anti-IgM secondary antibody. All of the other antibody assays are performed by ELISA or Luminex™, using a modified version of the Athena Multi-Lyte kit (Zeus). Serum IgM and IgG levels are measured either by nephelometry or by Luminex™. dsDNA, histone, Sm and RNP antigens are associated with SLE, Phosphorylcholine antibodies provide a measurement of B1 B cell function/activation and may be protective (Su et al., 2008, Rheumatology (Oxford) 47:1144-1150; Binder et al., 2005, Springer Semin Immunopathol 26:385-404). Galectin-1 is believed to facilitate binding of the pre-BCR to bone marrow stromal cells (Gauthier et al., 2002, Proc Natl Acad Sci USA 99:13014-13019). Galectins also appear to play roles in plasmablast and memory B cell differentiation (Tsai et al., 2008, J Immunol 181:4570-4579; Acosta-Rodriguez et al., 2004, J Immunol 172:493-502) and galectin antibodies have been found in serum and renal biopsies of lupus patients (Lim et al., 2002, Biochem Biophys Res Commun 295:119-124; Kang et al., 2009, Lupus 18:22-28; Massardo et al., 2009, Lupus 18:539-546). Higher serum levels of autoantibodies in SLE patients with abnormal L chain rearrangements are expected, consistent with defective central tolerance. Also, an increased fraction of transitional B cells in approximately one quarter of lupus patients is expected (Sutter et al., 2008, Clin Immunol 126:282-290).

If increases in the transitional fraction or naïve autoantibody repertoire are not correlated with abnormal L chain rearrangements, experiments can be designed to determine if the transitional B cell fraction is enlarged due to an excess of BAFF (Miller et al., 2006, J Immunol 176:6405-6410; Cancro et al., 2009, J Clin Invest 119:1066-1073), which is measure by ELISA on the serum (R&D Biosystems) or due to proliferation (measure by Ki67 staining, which we do not detect in the transitional compartment of healthy controls). Because B cells consume BAFF (Crowley et al., 2008, Immunol Res 42:75-83), BAFF levels are correlated with the absolute B cell count. The κ/λ L chain ratio in the transitional compartment, which, at least in theory, is independent of the absolute B cell count is also analyzed. If BAFF levels are high and B cells are protected from apoptosis in the pre-B cell stage, an increased fraction of λ-expressing transitional cells is expected. Conversely, if the transitional compartment is expanded due to an increased influx of un-edited B cells from the bone marrow, a decreased fraction of λ+ B cells is expected.

B cells play a critical role in lupus. B cell depletion has not been very successful in human lupus. There are many possible reasons for failure of B cell depletion in human lupus, including that autoreactive B cells may not be fully purged from the repertoire or that autoreactive B cells rapidly re-form following therapy. The latter alternative is likely if early B cell tolerance is defective. The experiments were designed to measure the frequency of early B cell defects in patients with lupus by surveying non-productive antibody gene rearrangements and for determining if these defects are correlated alterations in the phenotype and repertoire of naive B cells. Experiments were also designed to determine if alterations in antibody rearrangement are stable in lupus patients with active disease, and whether they vary in peripheral B cell subsets from patients with lupus. These experiments serve to at least provide insight into early B cell selection checkpoints and the IgM autoantibody repertoire in lupus. These studies also form the basis for identifying and ultimately treating a subset of lupus patients with early B cell tolerance defects, who may benefit from chronic B cell depletion or from therapies that prolong or modify bone marrow B cell development.

Example 8

Comparison of RS Rearrangement Frequency to Rearrangement Frequencies of Other L Chains The next set of experiments was designed to determine whether the levels of antibody L chain rearrangements globally decreased in B cells from SLE patients with low RS levels. Receptor editing is a B cell tolerance mechanism in which B cells with autoantibodies can correct their antibody specificity by undergoing further antibody gene rearrangement, most commonly at the L chain loci (Tiegs et al., 1993, J Exp Med 177:1009-1020; Casellas, et al, 2001, Science 291:1541-1544; Nemazee, 2006, Nat Rev Immunol 6:728-740; Radic, et al, 1993, J Exp Med 177:1165-1173; Gay et al., 1993, J Exp Med 177:999-1008). Without wishing to be bound by any particular theory, a receptor editing defect would predict that in addition to low levels of RS rearrangements, a higher frequency of germline (unrearranged) κ alleles, skewing towards proximal Jκ segments (Trak et al., 1994, J Exp Med 180:1805-1815) and fewer isotypically included peripheral B cells (Li, et al, 2002, J Exp Med 195:181-188) should be observed. A low level of L chain receptor editing would suggest that B cell tolerance is broken at the pre-B cell stage, when most L chain rearrangements occur.

Figure 14:
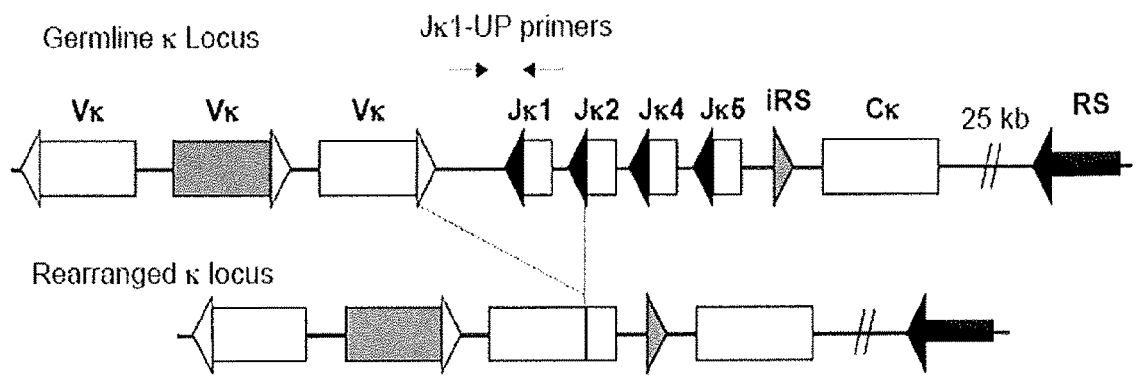
FIG. 14 is a schematic of an Jκ1-UP assay. Primers that amplify Jκ1 and the upstream genomic flanking sequences were used to quantify the frequency of unrearranged κ alleles.
Figure 15A:
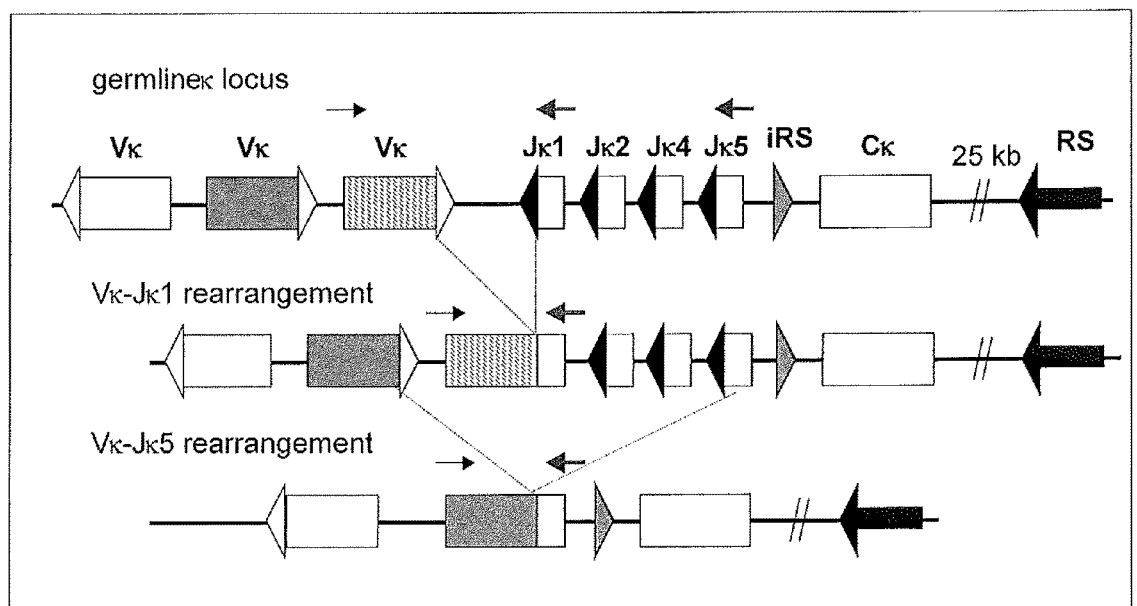
FIG. 15A is a schematic of the kappa light chain calibrating assays. Vκ-Jκ1 measures the frequency of primary (early) kappa light chain gene rearrangements. Vκ-Jκ5 measures the frequency of late kappa light chain gene rearrangements. We have performed these assays in non-quantitative form on murine B cells and B cell hybridomas.
Figure 15B:
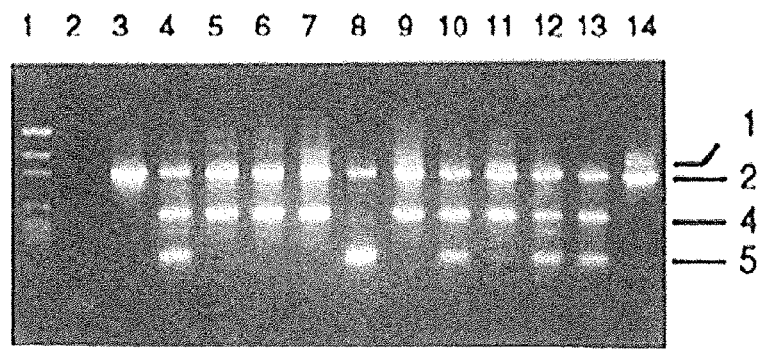
FIG. 15B is an image demonstrating the size of the amplified products. The Vk primer is a degenerate primer that detects approximately 80% of all mouse Vk genes (Schlissel and Baltimore Cell 1989; Luning Prak and Weigert, J. Exp. Med 1994). The reverse primer used in this figure was situated in Jk5 (Luning Prak and Weigert, J. Exp. Med 1994). Rearrangement to Jk1 yields a product of 1.6 kb, rearrangement to Jk2 1.2 kb, Jk4 600 bp and Jk5 270 bp. Lanes contain pGEM markers (lane 1), water (lane 2), various hybridoma samples (lanes 3-10). All of the hybridoma samples have a Jk2 band due to the Jk2 rearrangement in the Sp2/0 fusion partner.

In order to determine whether SLE patients with low RS levels have globally lower levels of L chain rearrangement, RS rearrangement levels are correlated with other assays for L chain gene rearrangement. Quantitative PCR assays (qPCR, hydrolysis probe method) are performed on genomic DNA from CD19+ peripheral blood lymphocytes purified by flow cytometry to measure the level of L chain gene rearrangement: Jκ1 germline (uses a forward primer in genomic DNA upstream of Jκ1 and a reverse primer in Jκ1; this assay measures mostly unrearranged κ alleles, see FIG. 14), Vκ-Jκ1 (measures primary κ L chain rearrangement), Vκ-Jκ5 (measures secondary κ L chain rearrangement; Jκ5 is the most distal Jκ segment; see FIG. 15), and Vκ-RS and iRS (both probably measure secondary or tertiary κ L chain rearrangement). L chain assays are established using primers for Jκ1 germline and RS assays and with primers from the BIOMED-2 consortium for the Vκ-Jκ assays (van Dongen et al., 2003, Leukemia 17:2257-2317). Amplicons are cloned and sequenced to confirm assay specificity. Cloned amplicons diluted into genomic DNA lacking the rearrangement being detected (murine MEFs) are used for absolute quantification. Input DNA is normalized with β-actin qPCR, Vκ-Jκ5 PCR is run at very short extension times (~2 seconds) to minimize amplification of upstream Jκ rearrangements.

Without wishing to be bound by any particular theory, if low IRS rearrangement levels are due to reduced L chain receptor editing, concomitant decreases in Vκ-RS and Vθ-Jκ5 are expected. Conversely, increased levels of Vκ-Jκ1 and Jκ1 upstream (germline κ alleles) are expected. It is believed that a low RS frequency corresponds to a lower average number of L chain gene rearrangements per B cell in the subset of SLE patients with low RS levels. The results are useful for understanding the nature of the B cell defect in SLE patients with low RS rearrangement frequencies.

Example 9

Bone Marrow B Cell Development

The next set of experiments was designed to determine whether bone marrow B cell development is accelerated in SLE patients with low RS levels. It is believed that one way in which early B cell tolerance can be by-passed is if bone marrow B cell development were accelerated, allowing B cells to exit without adequate censoring or receptor editing. Bone marrow development can be evaluated using flow cytometry of peripheral blood cells for left-shift (in B and non-B cell lineages) and cell division by Ki67 staining (see FIG. 13B). It has been observed that approximately one third of SLE patients have an elevated fraction of circulating transitional B cells (early bone marrow émigrés). This analysis is useful for assessing whether an increased fraction of transitional cells correlates with low RS levels and/or if B cells arise by accelerated B cell development, globally altered hematopoiesis or peripheral expansion in a subset of SLE patients.

Figure 13A:
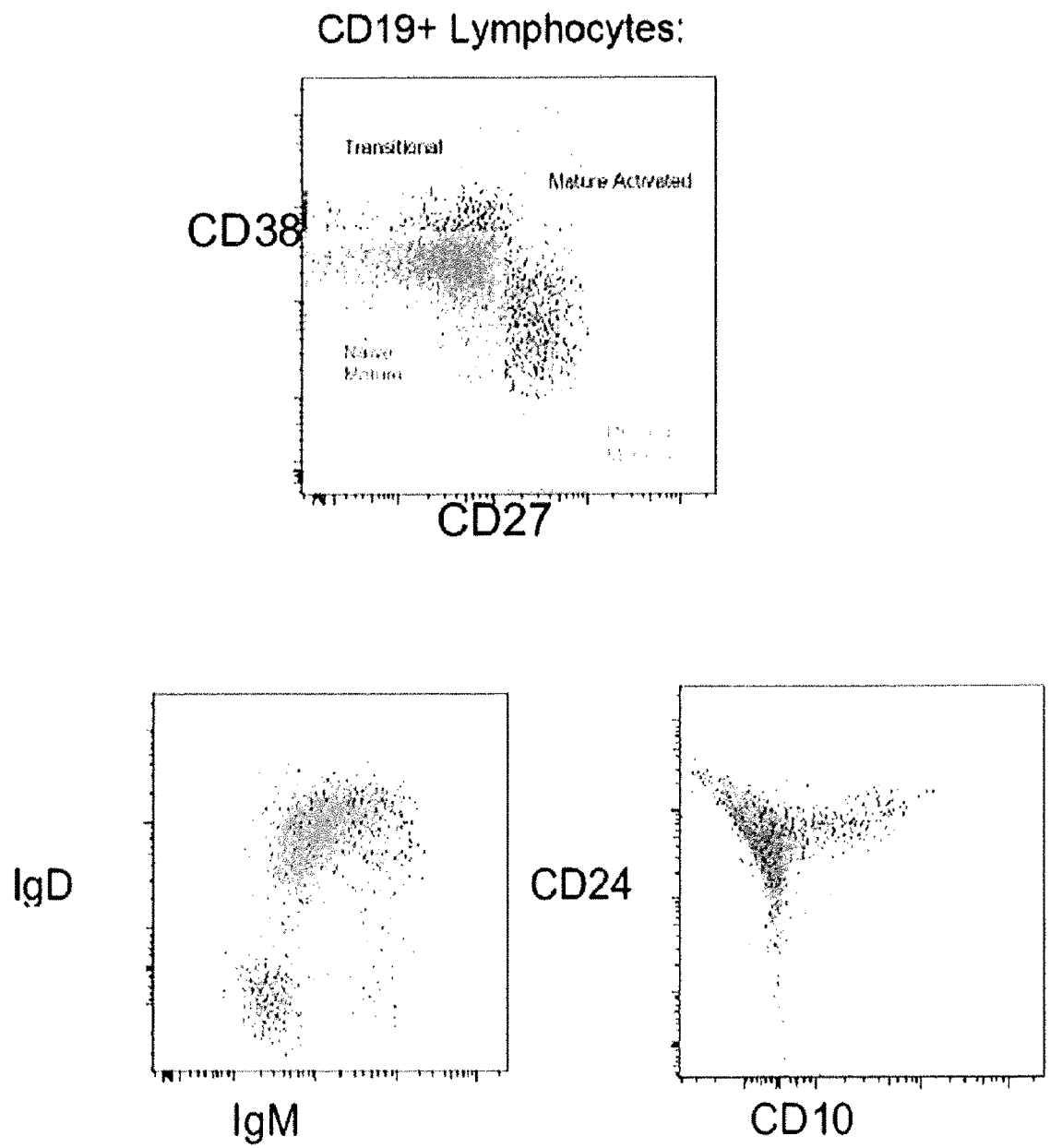
FIGS. 13A through 13C, is a series of images demonstrating transitional B cell analysis and increased relative fraction in SLE.
Figure 13B:
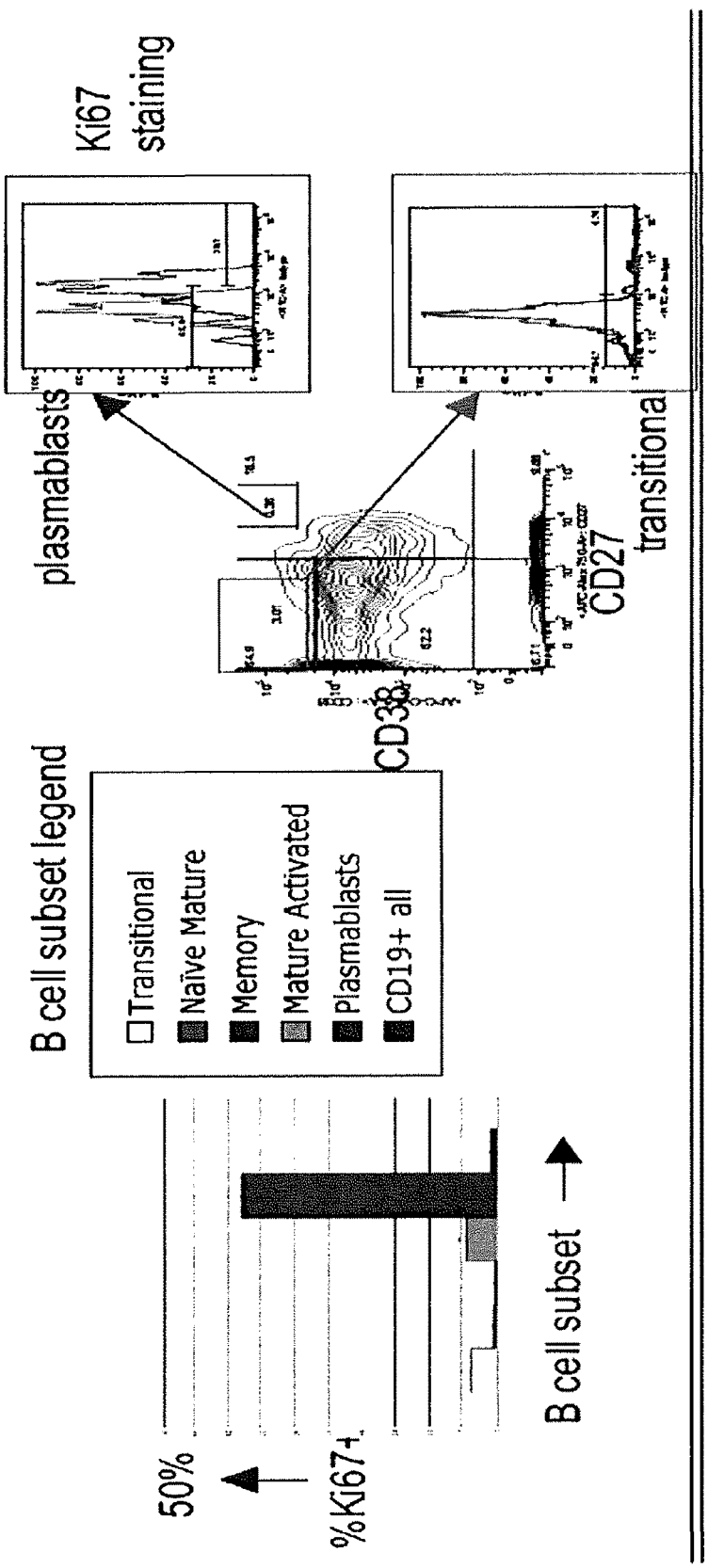
Figure 13C:
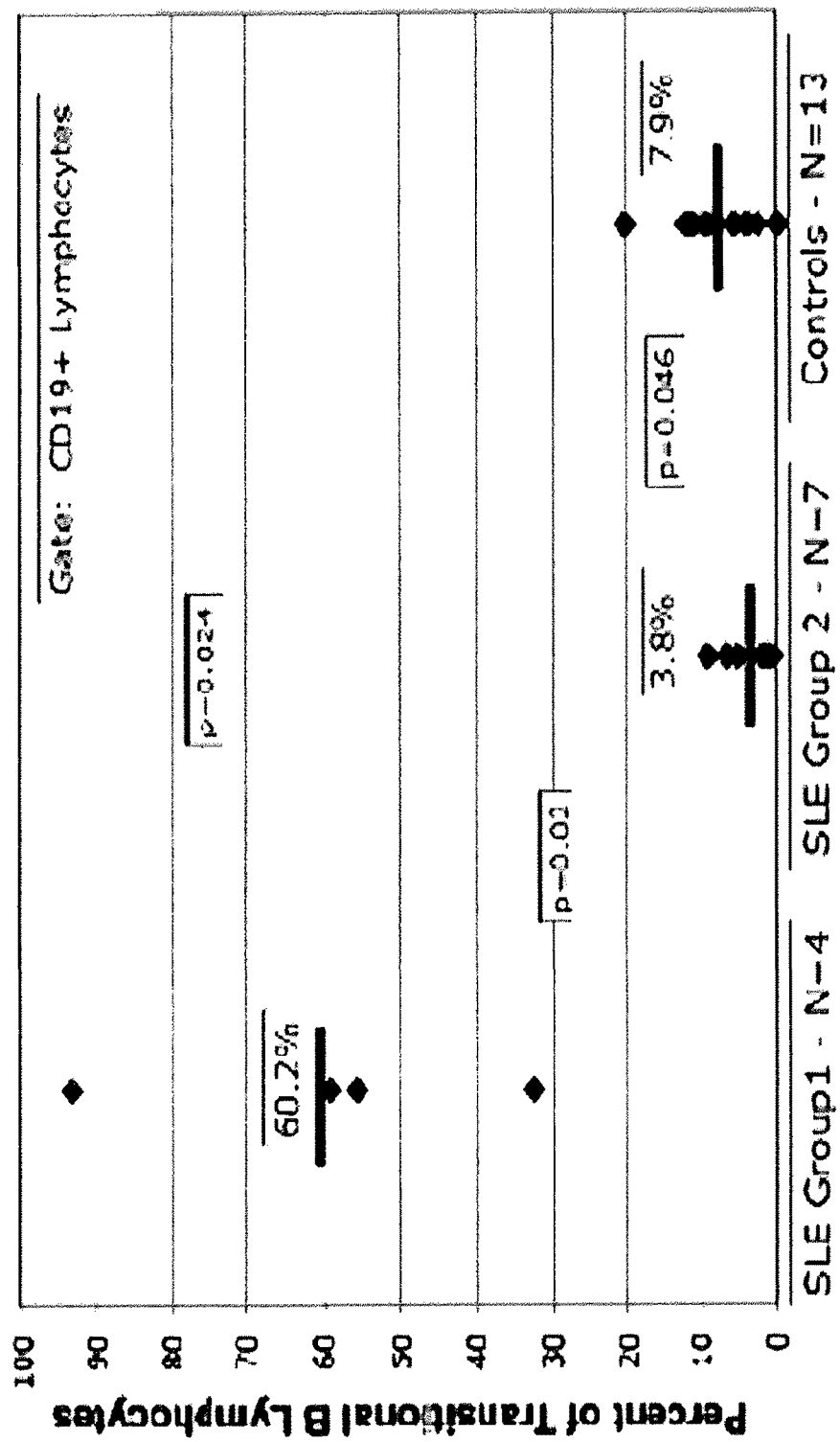

Peripheral B and non-B cell fractions are evaluated for evidence of a left shift in patients with a low RS frequency. In humans, the transitional B cell fraction can be reliably enumerated as shown in FIG. 13A (Abdallah et al., 2006, Clin Transpl 427-437). A relative increase in the transitional cell fraction in peripheral blood B cells in 3 out of 11 SLE patients have been observed (FIG. 13C). To evaluate the proliferative potential of the transitional compartment in humans, Ki67 staining on peripheral blood B cell subsets is performed (FIG. 13B).

Experiments were designed to determine if lupus patients with low RS frequencies have a left-shifted B cell compartment or other evidence of a left-shift across multiple hematopoietic lineages. For B cells, transitional cells, based upon CD27−, CD38++ and further subset as shown in FIG. 13 (with CD24++CD10+ representing the earliest stage) are measured. Whole blood for absolute counts are assayed and relative increases (suggestive of left shifts) in the following populations are measured: 1) RBC reticulocytes; 2) immature platelets; 3) fraction of neutrophil bands (CD33+, CD16int, CD13+, confirmed in elevated eases by manual counting); 4) fraction of NK cells that are bright for CD56 and CD27 and subset dim/negative for CD16; 5) fraction of promonocytes (CD64+, CD14$^{int}$, HLA-DR++).

Without wishing to be bound by any particular theory, it is belived that SLE patients with low RS levels have an increased relative frequency of transitional cells. The analysis of other hematopoietic lineages will indicate if bone marrow development in general is affected or if the defect is specific to the B cell lineage. There are many reasons to have left-shifted cells circulating in the peripheral blood including: infection, pregnancy and, in the case of reticulocytes, certain forms of anemia. These confounds can be minimized through a subject exclusion criteria discussed elsewhere herein. Additionally some lupus patients have platelet and RBC abnormalities (for example, Evan's Syndrome, (Cines et al., 2009, Blood 113:6511-6521)). Yet SLE patients with multiple hematologic abnormalities might indeed have a bone marrow defect. Another potential variable is if SLE patients are receiving therapy that affects the bone marrow. It is important to correlate these results with clinical parameters including current and past medications. If an elevated transitional B cell fraction with no significant evidence of a left shift in other hematopoietic lineages and/or no correlation or an inverse correlation with RS levels is observed, it is possible that the elevated transitional B cell fraction is due to expansion of B cells in the transitional compartment, rather than rapid or abnormal transit through the marrow. To address this possibility, Ki67 staining is performed using plasmablasts as a positive control and is compared with the Ki67 profile in SLE patients with elevated vs. normal transitional B cell fractions (see FIG. 13B). The size of the transitional compartment is correlated with the serum BLyS level and the $\kappa/\lambda$ ratio (which is expected to be skewed towards $\lambda$ in the setting of elevated BLyS, given recent data in mice that suggest that BLyS promotes the survival of B cells with $\lambda$ rearrangement).

Example 10

B Cell Proteome in SLE Patients with Low RS Levels

A high-definition mass spectroscopy approach (~2000 proteins per cell population) is used to determine whether there is an early B cell-like "signature" that accompanies low RS levels in SLE patients. The proteome of B cells treated with imatinib or belimumab, which target predominantly the pre-B and transitional stages of B cell development, respectively, are also evaluated.

Experiments were designed to determine if a low RS level identifies a subset of SLE patients who have B cell abnormalities that can be ameliorated by bone marrow-directed or early circulating B cell targeted therapy. The proteomic analysis may also lead to the identification of additional therapeutic targets for SLE and/or to a system for profiling individual B cell defects in SLE. This approach provides individualized therapy for some of the immunologic defects that currently take refuge under the SLE umbrella.

Figure 6C:
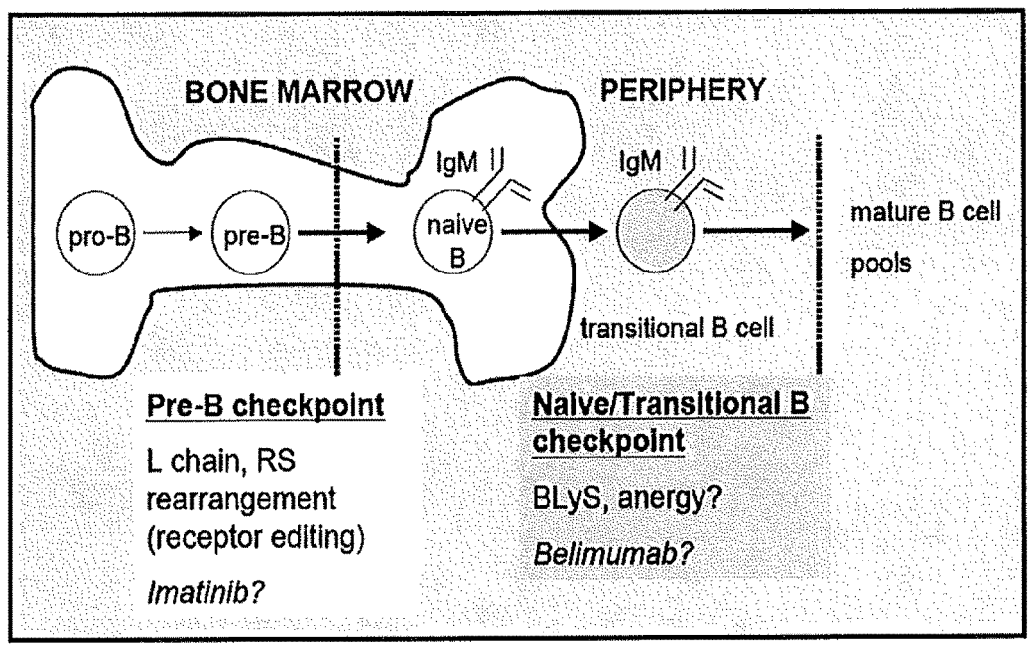

Imatinib and belimumab was used in these experiments on SLE B cells because both are promising drugs that appear to have therapeutic effects on early stage B cells and on SLE (see FIG. 6C).

Imatinib (aka Gleevec, STI571) is a small molecule inhibitor used for the treatment of chronic myelogenous leukemia (CML) and a subset of patients with gastrointestinal stromal tumors (GIST). Imatinib inhibits the BCR-ABL1 kinase, among others. Even in non-transformed cells, imatinib inhibits the ABL kinase and the ABL kinase can phosphorylate the BCR. It is believed that reduced BCR phosphorylation may in turn induce or re-induce RAG (i.e. promote L chain editing) in pre-B cells (Tze et al., 2005, PLoS Biol 3:e82). Consistent with this idea, pre-B ALL cells treated with imatinib in culture upregulate RAG1/2 and progressively shift from $\kappa$ to RS to $\lambda$ rearrangement with increasing lengths of imatinib treatment (Klein et al., 2005, J Immunol 174:367-375). Furthermore, imatinib has been reported to ameliorate nephritis and improve survival in MRL/lpr and NZB/W mice (Sadanaga et al., 2005, Arthritis Rheum 52:3987-3996; Zoja et al., 2006, Kidney Int 70:97-103). The beneficial effects that were reported for imatinib in these lupus-prone mouse strains were attributed to other properties of imatinib (such as its ability to inhibit the PDGF receptor), although both studies documented changes that could reflect improved B cell tolerance including reduced serum concentrations of anti-dsDNA antibodies. Therefore, it is believed that imatinib promotes receptor editing and/or improves the pre-B cell bone marrow tolerance checkpoint. Accordingly, experiments were designed to use proteomic profiling to identify the B-cell specific targets of imatinib, including potential targets of relevance to receptor editing in human B cells.

Belimumab (aka Benlysta, LymphoStat-B) is a fully humanized monoclonal antibody that blocks soluble BLyS (B Lymphocyte Stimulating, aka BAFF, TALL1, TNFSF13B). BLyS is a TNF superfamily member that binds to several receptors on B cells including BCMA, TACT and BR3. Within the transitional B cell compartment, the level of soluble BLyS dictates compartment size and stringency of selection, influencing whether autoimmune B cells are shunted off into an anergic/cell death pathway or are allowed to mature and enter the follicles. Mice that express elevated levels of soluble BLyS develop autoimmune features including lymphoid hyperplasia with elevated B cell numbers, autoantibody production, circulating immune complexes and inflammatory infiltrates. Furthermore, a positive correlation has been demonstrated between serum BLyS levels, serum autoantibody levels and disease activity in SLE patients. In a phase II multi-center trial ~70% of patients with baseline anti-dsDNA or ANA antibodies experienced a reduction in disease activity following treatment with belimumab over a one-year period (Ding et al., 2006, Curr Opin Investig Drugs 7:464-472; Mackay et al., 2009, Nat Rev Immunol 9:491-502).

Experiments were designed to compare the B cell proteome in SLE patients with low vs. normal RS levels. Perturbations in the B cell proteome that are caused by imatinib and belimumab are also analyzed. As an initial pilot experiment, two million cells were harvested from CCL-120 (a B cell lymphoblastoid line from an ALL patient) and CRL-2631 (a cell line derived from a patient with diffuse large B cell lymphoma-corresponding to a later, possibly post germinal center stage of B cell development). In addition, 0.5 million CD19+ and 0.5 million $\lambda$+ lymphocytes were purified from whole blood (from a healthy adult human subject) by magnetic bead separation. Cell pellets were lysed and run on SDS PAGE. Each sample lane was cut into 6 equal slices, and the proteins were digested using an in-gel trypsinization procedure (Ong et al., 2006, Nat Protoc 1:2650-2660). The resulting peptides were separated by nanoflow HPLC on a 15 cm RP column at 300 nL/min over 90 minutes and then analyzed using an LTQ-Orbitrap. The results were processed with MaxQuant (Cox et al., 2008, Nat Biotechnol 26:1367-1372) and searched against the IPI Homo sapiens database (v. 3.52).

In this pilot experiment, the total number of proteins identified (with a 2 unique peptide minimum) was 2,442. In each sample the total number of proteins identified was: 2018 (CCL-120); 1950 (CRL-2631); 1251 (CD19+ cells) and 1164 ($\lambda$+ cells). There were 728 unique proteins identified in only one of the two cell line samples. 1,639 proteins were identified in both 13 cell line samples. 445 proteins were found in 10-fold or greater abundance in CCL than in CRL (includes those not detected in CRL). Examples of CCL proteins include CD20, MHC class II and pre-B cell enhancing factor (PBEF, visfatin; a nicotinamide phosphoribosyl transferase that is found in elevated levels in inflammation. 442 proteins were found in 10-fold or greater abundance in CRL than in CCL (includes those not detected in CCL). 736 proteins were of similar abundance in both cell lines (below 2-fold change). 134 proteins were identified in the $\lambda$+ cells that were identified in the reference cell lines, but were absent in CD19+ cells. 51 proteins (identified in both CD19 and $\lambda$+ cells) were 10-fold greater in $\lambda$+ cells. These 51 proteins represent potential receptor editing and/or pre-B cell developmental targets, which can be further parsed by comparing their relative amounts in the pre-B cell line vs. the DLBL line. Roughly equal total numbers of proteins were identified in CD19 and λ+ cells (1251 vs. 1111). Only 59 of the proteins identified in the CD19 and λ+ cells were not found in either reference cell line (some of these could have been due to contaminating non-B cells in the cell samples).

The results from the protein quantification experiment illustrate that: 1) this technique identifies hundreds of proteins, many of which are B cell-specific; 2) the differences seen in B cell-specific proteins in each cell line are consistent with their described phenotype; 3) the similarity in the protein signature between the primary B cells and the cell lines suggests that using the cell lines as standards for quantification works well; and 4) differences between CD19+ vs. λ+ cells suggest potential proteomic differences that may correlate with RS levels and/or receptor editing. In short this is a powerful technique for comparing B cell populations and identifying shared groups of proteins that may be unique in SLE patients with low RS levels.

Analysis of the B cell proteome in SLE patients with low RS levels and B cells treated with belimumab or imatinib is as follows. First, standards for quantification of B cell-specific proteomes are defined. Second, sorted B cells from SLE patients with low RS levels are compared to B cells from SLE patients and normal controls with normal RS levels. Third, the effects of two candidate drugs that influence early B cell maturation/function (e.g., imatinib and belimumab) are analyzed. The overall goal of these experiments is to determine if SLE patients with low RS levels have an early B cell-like proteomic signature that is distinguishable from SLE patients with normal RS levels.

In order to refine standards for quantification of B cell specific proteomes, 2-3 different B cell lines are labeled using SILAC methodology with heavy (12C6) lysine and (13C6) arginine. The resulting protein lysates are compared to samples from SLE patients and control subjects for adequate protein coverage. The combination of cell lines providing maximal protein coverage are mixed in equal cellular quantities to yield labeled reference (Yu et al., 2009, J Proteome Res 8:1565-1576). This pooled reference is mixed in a 1:1 fashion (by cell count) with patient B cells. The cells are lysed and separated via SDS-PAGE (Ong et al., 2006, Nat Protoc 1:2650-2660). The resulting peptides are separated by nanoflow HPLC on a 15 cm RP column at 300 nL/min over 90 minutes and then analyzed using an LTQ-Orbitrap. The results are processed using MaxQuant (Cox et al., 2008, Nat Biotechnol 26:1367-1372) and searched against the IPI Homo sapiens database (v. 3.52) using Mascot.

B cell line profiles are compared to profiles from sorted B cell subsets from five healthy donors (bone marrow and apheresis samples are obtained): Pro-B (lymphocytes that are CD44−, CD27+, CD19+, IgM−, surface L chain−, CD138−, CD10+, dump− (dead, T cells, monocytes)), Pre-B cells (CD44+, CD27+/−, CD19+, IgM−, CD10+/−, CD24++, dump−(dead, T cells, monocytes)) and CD19+ peripheral blood B cell subsets: CD19+; CD19+ transitional, CD19+ κ+ and CD19+λ (See FIG. 13). Apheresis samples are used to increase the yield of transitional B cells, which are isolated using a negative enrichment by magnetic beads followed by flow cytometry for transitional markers. Stage-specific and shared proteins that are found in most individuals are used to construct a "consensus" proteome for each of the major early B cell stages: pro, pre and transitional. Next, B cell profiles from individual SLE patients are compared against cell line/sorted B cell standards to determine if there is overlap with pre-B cell line/early B cell population proteome profiles. A "consensus" profile is derived from peripheral blood CD19+ cells from low RS vs. normal RS and healthy subject B cells (approximately 10 subjects per group). Profiles in individual SLE patients are compared to their peripheral B cell subset immunophenotype. Proteins that are uniquely represented in any of the three subject groups will also be determined. By creating consensus profiles and comparing them to B cells of different developmental stages, a roadmap for interpreting some of the individual variability will be created.

Mass spectrometry will also be used to evaluate the changes induced by two candidate drugs for SLE, imatinib and belimumab. B cell proteomes in cell lines cultured in the presence or absence of drug using incubation conditions described in (Klein et al., 2005, J Immunol 174:367-375) are evaluated. The mass spectrometry technique is ideally suited for this application. Peripheral blood B cells from CML patients receiving imatinib (for at least 3 months—a human reconstitution time interval commonly used clinically) is also profiled. Peripheral blood B cells from patients awaiting renal transplant is also analyzed. In transplant patients, B cells from patients before vs. after receiving belimumab (time 0 vs. >3 months), in an effort to reduce their anti-HLA antibody levels, is also analyzed. The transplant study involves patients who are on the transplant waitlist, thus eliminating confounding effects of other immunosuppressive agents. The proteins that are altered by the drug are compared, focusing on shared changes between the cell lines and the primary B cells from patients. The imatinib and belimumab profiles to the SLE RS low vs. normal RS profiles and individual profiles are compared to determine if there are overlapping proteins that may be targets for therapy for SLE.

At the end of the process, molecules that meet the following criteria are identified: 1) expression of the molecule is developmentally correlated with early B cell maturation; 2) expression of the molecule is altered in a subset of lupus patients; 3) expression of the molecule is altered by either imatinib or belimumab. Candidate molecules meeting these criteria based upon the mass spectrometry analysis and the literature are analyzed further for expression using confirmatory Western blotting and/or quantitative reverse transcriptase PCR. If it is discovered that the profiles of imatinib or belimumab do not closely resemble the profiles of altered early B cell targets in SLE, additional compounds can be screened. For example, in the case of imatinib, there are other chemically related tyrosine kinase inhibitors such as dasatinib and nilotinib (which are offered as second-line therapy for imatinib-resistant CML), each with slightly different and not necessarily fully understood spectra of tyrosine kinase targets.

Example 11

Removal of Flow Cytometry from the Assay

The RS assay is significantly influenced by the B cell fraction (which can vary over an order of magnitude) and the proportion of λ+ B cells (see FIG. 4). The gold standard technique for determining the B cell fraction and the proportion of B cells that express λ light chains is flow cytometry. However, since logistical aspects of flow cytometry are anticipated to limit the number of labs that are able to perform the assay, it is desirable to develop and validate qPCR based calibrators to measure the B cell fraction and extent of antibody gene rearrangement in whole blood.

Experiments were designed to select and validate desirable primers. To measure the frequency of κ vs. λ B cells, qPCR assays are performed to measure κ and λ rearrangement, which are uniquely found in B cells. For λ, a degenerate V primer is used (situated either in the leader sequence or framework region 1, similar to what has been described in mice (Schlissel et al., 1989, Cell 58:1001-7)) and reverse primers in proximal (Jκ1), vs. distal (Jκ5) Jκ segments. Proximal Jκ rearrangements occur before distal Jκ rearrangements (Radic et al., 1993, J Exp Med 177:1165-73; Klein et al., 2005, J Immunol 174:367-75; Prak, et al, 1994, J Exp Med 180:1805-15). Thus Vκ-Jκ1 is used to measure the frequency of cells that have relatively few rearrangements, while Vκ-Jκ5 measures the frequency of cells with more extensive L chain rearrangements (see FIGS. 15A, 15B). The absolute levels of these rearrangements in a given amount of input DNA (relative to a cloned, diluted standard) is proportional to the B cell fraction whereas their ratio provides information on the extent of L chain rearrangement. Similarly, λ, VκRS and iRS (all of which usually occur after κ) measure the frequency of L chain rearrangements that occur in B cells that have undergone more extensive L chain rearrangement. The Jκ1-UP assay (shown in FIG. 14) measures the frequency of germline κ alleles, which is present in B cells and non-B cells in the sample. As such, the Jκ1-UP assay is valuable as a calibrator in samples that have been enriched for B cells. Vκ and Vλ primer sequences are obtained from the IMGT database (Lefranc et al., 2009, Nucleic Acids Res 37: D1006-12). Primer sequences are screened against the repetitive element database using repeatmasker (Jurka et al., 2005, Cytogenet Genome Res 110:462-7) and tested for complementary. The Jκ primers are situated downstream of the corresponding Jκ segments (in the intergenic region) so that probes may be anchored within the Jκ and downstream region. The Vκ-Jκ5 assay is performed at very short extension times (~2-5 seconds) in order to avoid amplifying rearrangements with upstream Jκ gene segments. The same RS reverse primer is used in the iRS and Vκ-RS assay. The reverse primers are engineered in J-C intergenic region. Because there is polymorphism in the human population in the λ J-C region (Lefranc et al., 2009, Nucleic Acids Res 37:D1006-12), the most common J-Cs are used. PCR amplifications are performed with 2-3 candidate primer pairs per assay type. Amplifications are performed on B cell DNA, non-B cell DNA (HeLa or other non-B cell line) and water. Primer sets that produce bands of the predicted mobility are subjected to gradient cycling to further optimize the reaction conditions, if needed. Amplicons from the best primer pairs for each assay is TA cloned and sequenced (TOPO TA, Invitrogen). Sequences are analyzed for homology with known germline V gene sequences with IgBLAST. Validated sequences are used for titration experiments. Experiments are performed to determine the optimal amount of DNA per reaction for each of the qPCR assays. Reaction volumes are scaled back to the smallest amount in which amplification can be reliably performed to minimize cost.

The next set of experiments are directed to primer titration studies for calibrator validation. Once each primer pair has been validated, the sensitivity, linearity and reproducibility of each PCR assay is evaluated in a series of titration experiments. First, the sensitivity of the assay is determined by diluting known amounts of cloned product into 100 ng of genomic DNA that lacks the rearrangement of interest (see FIG. 4). The minimum required sensitivity for each assay is to be able to detect one copy in 10,000 genomes. This minimum is based upon performing the assay in whole blood. Amongst white blood cells (that are the only cells in blood with DNA), lymphocytes comprise approximately 40%, B cells comprise 10-20% of lymphocytes, the L chain rearrangements occur in at least 10% of B cells. In some situations, some patients with SLE are lymphopenic, further reducing the frequency of the amplified product (0.04-0.08% or a minimum of 1 copy in 2,500). The second calibration involves mixing experiments with κ vs. λ expressing B cells. The individual L chain qPCR assays should be able to reliably discriminate a 10% shift in cell line composition (in other words, they should be able to distinguish a κ/λ mixture of 45/55 from 55/45). The cell mixing experiments are repeated using cell mixtures that are serially diluted into non-B cell DNA. In addition to being sensitive, PCRs must be highly reproducible (titrations are performed in triplicate and repeated at least three times for each assay). If there is high variability of the triplicate determinations (CV>5%), the sample quality and technical issues with the PCR is investigated. If variability persists, it may prompt re-design of the primers or further optimization of the assay conditions.

The next set of experiments is directed to compare sample types. The original RS assay was performed on fresh whole blood drawn into EDTA tubes, so this serves as the basis for comparison. The PAXgene tube provides stability for shipped specimens and is a target sample tube type for the new assay. Frozen PBMCs are useful because this sample type is often banked in large clinical trials. In addition, PBMCs accommodate B cell enrichment strategies (for example CD19 separation by magnetic beads, if required). The RS assay (including the calibrators) is run on these three sample types and the results between assays are correlated. Because cost is a limiting factor, 10 rounds of conventional RS assay is performed. Specifically, CD19+κ+ vs. CD19+λ+ cells are sorted from whole blood drawn into sodium EDTA and RS qPCR is performed on each fraction as described elsewhere herein. RS qPCR is performed along with all of the calibrators on whole blood EDTA, PAXgene and frozen PBMC samples from the same patient. For whole blood and frozen PBMCs. DNA is isolated using a Gentra Puregene kit (Qiagen). For the PAXgene tube, the PAXgene DNA blood kit (Qiagen) is used. Sample DNA concentrations is determined using spectroscopy (Nanodrop). All L chain PCRs are performed in triplicate. The iRS and VκRS frequencies in the different sample types are compared and correction factors based upon the B cell fraction is applied (absolute lymphocyte count (ALC) is obtained from the complete blood count (CBC), and multiply the ALC by the CD19+ lymphocyte fraction to obtain the absolute B cell count). The results obtained with the κ and λ PCR calibrators is compared to the flow cytometry based κ /λ , ratio, and the RS measurements on sorted cells are compared to those with the calibrator-based corrections on all sample types. For example, it is believed that an iRS frequency of 1 copy per genome is obtained using sorted λ+ B cells. On the unsorted whole blood sample in a subject with 4% of their WBCs being B cells and 40% of those being λ+, an iRS frequency of 0.016 copies per genome is expected. The closeness of the iRS and calculated iRS frequencies between the different sample types can be determined. Ratios between the copies per genome measurement of the different PCRs can also be determined. For example, in a sorted B cell population that is highly rearranged, the ratio of copies per genome for (iRS+VκRS+VκJκ5+λ)/(Jκ1UP+Vκ-Jκ1) should be high. The analysis of ratios also enable for determining if individual L chain PCR measurements occur in stable ratios. For example, the ratio of Vκ-Jκ1/2 to Vκ-Jκ4/5 might be 5:2 and not vary by more than 5-10% between individuals. If this is the case, it may be possible to drop some of the L chain assays without losing information content. On the other hand, having a stable ratio could serve as a quality control. It is also possible that L chain ratios are stable in normal subjects but variable in SLE patients, particularly in the setting of clonal expansion.

B cell separations are used to determine the quantitative similarity between the RS assay and the whole blood assay. It is expected that both assays produce similar results (within 10% of each other) or for the results of the new and the old assays to be linearly related (for example, old assay reading× 1.1=new assay reading). If they are not related, this parallel sample analysis is useful to hone in on the most robust primer sets. Analysis on the sorted cells serves as a gold standard for all of the calibrator PCRs. Flow cytometry (analysis for CD19 fraction and $\kappa/\lambda$ ratio) on up to 50 additional samples from patients with and without SLE (roughly 25 of each) can be performed to obtain a range of RS values and further validate the L chain calibrator assays.

RS Analysis on Whole Blood

The analysis of RS levels is performed on normal subjects and as described elsewhere herein. Samples are run in triplicate for each of the L chain PCR assays. Calibrators are used to determine the B cell fraction, $\kappa/\lambda$ ratio and extent of L chain rearrangement. A standard approach in the clinical laboratory for evaluating the "normal" or reference range of an assay is to perform the assay on 50 healthy controls and determine at which points measurements fall outside of the 95% confidence interval on either side of the distribution. Since PCR assays are often log-normally distributed, reference ranges are evaluated for statistical parameters using both mean and median values. Based upon our previous analysis of RS levels in 26 normal subjects, an average level in $\lambda$+ B cells of 1.11 RS copies per genome with an estimated S.D. of +/−0.27 copies was observed. If the whole blood assay is comparable to the old iRS assay, by recruiting 50 additional healthy subjects, the total sample size is 76 subjects for the normal reference range, which allows for a more precise mapping of the confidence interval.

Sample Quality Experiments

To evaluate the effects of common pre-analytical variables on the RS rearrangement assay, RS and other L chain PCRs are compared in at least five samples from healthy subjects that are processed in parallel. These comparisons are important for showing how the assay performs on shipped specimens (which occurs commonly in the clinical trial setting). Unprocessed samples (whole blood and spun PAXgene tubes) are stored at room temperature for 24 and 48 hours and compared with fresh samples. The effect of prepping PBMCs on fresh vs. 24-hour samples is also analyzed. To simulate hemolysis, aliquot of anticoagulated blood is pushed through a narrow bore syringe and the hemolyzed sample is compared to the non-syringe treated aliquot. Any of the above mentioned pre-analytical changes that result in greater than a 15% deviation from the freshly processed samples is deemed unacceptable.

Example 12

Association of Low RS Frequency with a Subset of SLE Patients with More Aggressive and/or Therapy Resistant Disease Experiments were designed to evaluate the utility of the assay in distinguishing clinical subsets of SLE. This assay can identify a subset of SLE patients with bone marrow B cell tolerance defects that require more aggressive, bone marrow targeted therapy.

SLE Subject Recruitment

Patients with treatment-resistant disease and/or lupus nephritis and patients with more benign SLE (limited organ damage, SLEDAI scores of 2 or below, no renal involvement, and/or good response to first-line therapy) are analyzed. The patients with active disease are monitored on two visits at least three months apart, with the aim of collecting data in the same subject on changes in disease activity and/or medication and the effects of these changes on the RS level. The logistics of subject recruitment and sample collection is discussed elsewhere herein. In addition, the following is collect from SLE subjects: autoimmune serology (from medical record; ANA, dsDNA, SSA, SSB, RF, anti-Sm, APLA, complement levels), other pertinent clinical lab studies if available (ESR, CRP, serum creatinine, DAT, LDH), past and current medications, years with diagnosis of SLE, organ systems affected/damaged by SLE, pathology reports (WHO nephritis score, if available), presence of coexisting autoimmune disorders, family history of autoimmune disease, SLEDAI score, current complaints (at the time of visit). Patients receiving oral steroids are asked to withhold their AM dose until after the blood draw because steroids acutely lower the lymphocyte count.

RS Analysis on SLE Subjects

Figure 16:
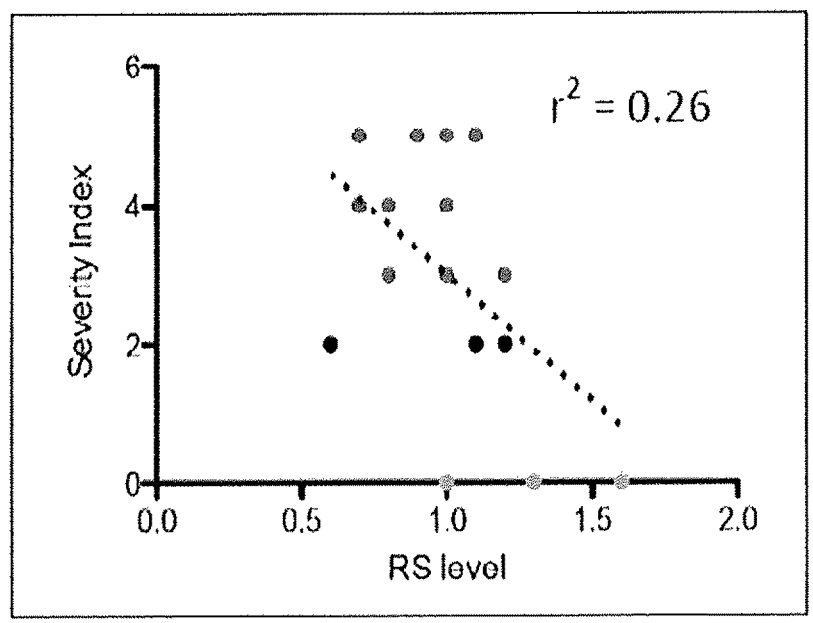
FIG. 16 is a graph demonstrating that RS level and severity of SLE disease are correlated. To determine if RS level and SLE disease activity were correlated, we reviewed the charts of 20 SLE patients on whom we had obtained both κ and λ RS levels. The RS level shown herein represents the sum of the κ RS and the λ RS. We calculated a disease severity index based upon a 5-point scale with 0 being the least and 5 being the most severe. The scale was based upon medications (with patients on major immunosuppressives such as cytoxan receiving higher scores, as did patients with evidence of multi-organ involvement, vasculitis, nephritis, or comments on treatment-resistance.) All patients who are listed for or received a renal transplant got a score of 5. Conversely, patients with only dermatologic signs of disease received a score of 0. Patients with mostly joint pain tended to fall in the 2-3 range, whereas those with vasculitis and/or antiphospholipid antibody syndrome tended to score as 3-4. Four of the data points overlap.

The RS analysis is performed on whole blood using the L chain calibrators, as described elsewhere herein. Specifically, RS level in the active and the quiescent SLE patients are compared and determine if the RS level is lower in the former group. It can also be determined if the RS level is lower in SLE than in the healthy control subjects. The three subject groups (SLE high disease activity, SLE quiescent and healthy controls) are compared for demographic similarity via one-way analysis of variance followed by 2-tailed Student's t test for age, sex, race, $\kappa/\lambda$ ratio, B cell fraction and absolute B cell count. Based upon FIG. 16, the average total RS level is approximately 0.95 copies per genome in the active group and ~1.25 copies per genome in the inactive group. With 50 SLE patients in each group, a standard deviation of 0.5 for each group, the estimated statistical power of this comparison is 85% ($\alpha$=0.05). If RS measurements are not normally distributed, medians of the measurements is compared using a non-parametric statistic such as the Mann-Whitney test. The level of variation in ratios of the different L chain copy numbers is analyzed and these ratios are compared to those obtained in normal controls. If very high RS levels or unusual L chain ratios are observed, the sample for clonal expansion is analyzed. RS and other L chain rearrangement frequencies in subjects with active SLE at two different time points are also compared. In many of these patients the therapy may have changed between the two time points. This allows for determining the stability of the RS measurement over time and whether or not therapy influences the RS or other L chain rearrangement levels. If the RS level changes from one time point to the next in the same patient, it will prompt additional future studies in larger numbers of SLE patients and controls to determine the source of the intra-individual variation.

Entry of all Data into Relational Database, Queries, Unblinding and Results Summary Data analysis templates are created within the first month of the study and data entry into the database occurs in nearly real time. Data entry templates have QC features including sum checks for flow cytometry quadrant statistics and results that are outside permissible data ranges are flagged automatically. Approximately 10% of the data are entered in duplicate to monitor data quality. For relational database queries, correlation analyses between each clinical parameter and the L chain PCR results are performed. Flow cytometry results is also correlated with L chain PCR results. These queries detect the most highly correlated variables providing early proof-of-concept data which provide direction for future studies.

The results presented herein demonstrate that the assay is useful for defining a subset of SLE patients with early B cell defects who may respond better to bone marrow targeted therapy. The whole blood RS assay is useful in clinical trials and in the general patient population as a test kit.

Example 13

Application of the RS Assay to Multiple Patient Populations

Imatinib targets pre-B cells, influences BCR signaling and has been shown to ameliorate disease in two different mouse models of lupus (Zoja et al., 2006, Kidney Int 70:97-103; Sadanaga et al., 2005, Arthritis Rheum 52:3987-96). If imatinib raises RS levels, it may be another candidate therapy for early B cells in SLE and other diseases in which imatinib is administered (for example, chronic myelogenous leukemia and gastrointestinal stromal tumors). In addition, the RS assay may be applicable to other autoimmune diseases, such as type 1 diabetes (T1D). In non-obese diabetic mice, which have low RS levels, diabetes is ameliorated by belimumab therapy and there are clinical trials underway to evaluate B cell targeted therapy in the treatment of T1D (Zekavat et al., 2008, J Immunol 181:8133-44). The RS assay is also being performed on T1D patients who are undergoing pancreatic islet transplantation (and some of whom are receiving B cell depletion therapy) as part of an ongoing multi-center clinical trial. In addition, RS frequency can be evaluated in belimumab treated patients who are awaiting renal transplantation. There are several other diseases in which B cells play a significant role including rheumatoid arthritis, immune thrombocytopenia, Sjogren's syndrome, myasthenia gravis, pemphigus vulgaris and multiple sclerosis. Another area for this assay is to predict autoimmune disease. This information could be used in the future to treat patients preventively or subject them to closer monitoring.

Example 14

Mass Spectrometry to Compare Kappa and Lambda B Cells

Figure 17:
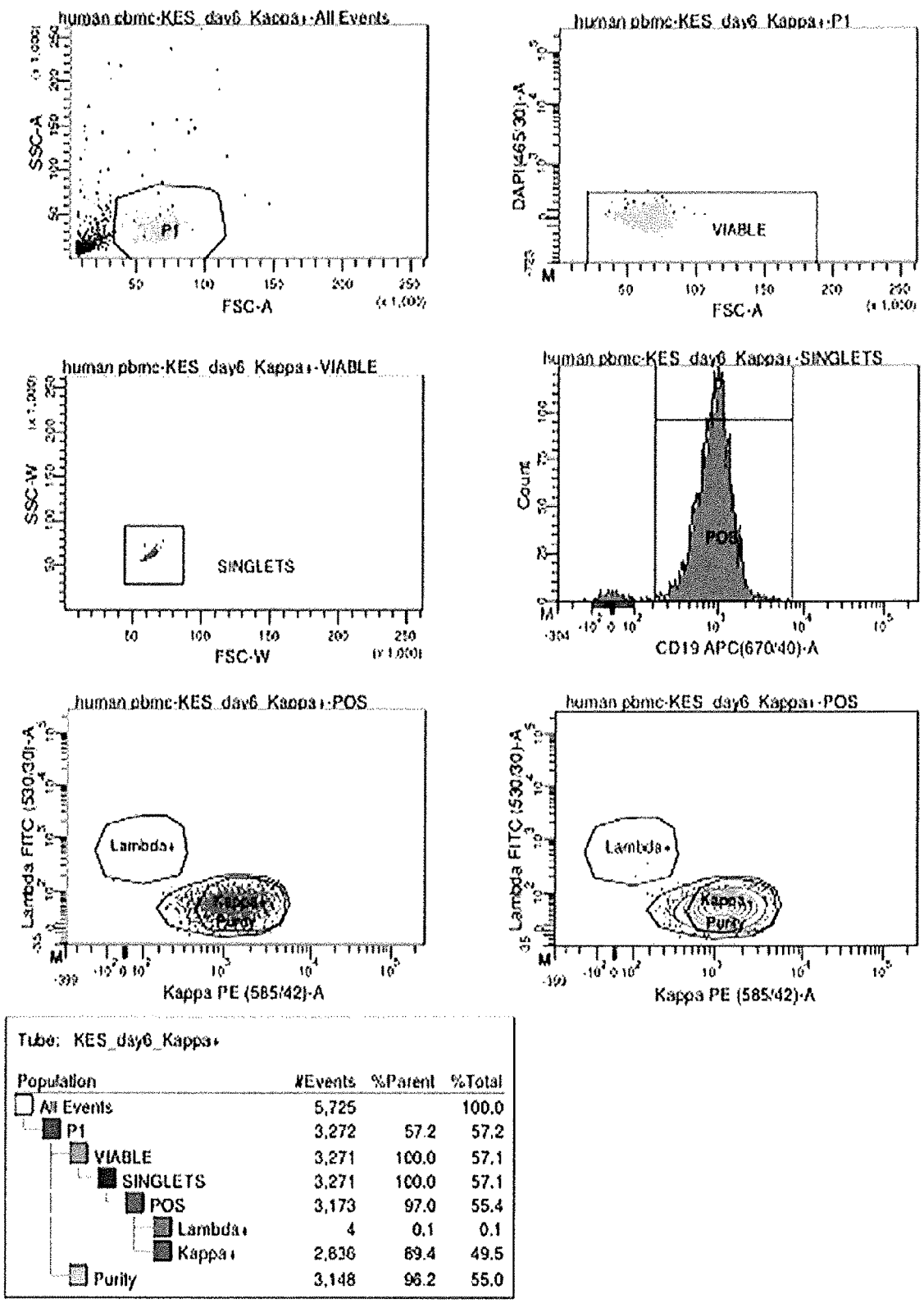
FIG. 17 is a series of images demonstrating B cell sorting scheme and purity check. CD19+ B cells were sorted from peripheral blood for expression of kappa vs, lambda light chains. The fractions obtained were more than 95% pure.

The following experiment was performed to compare the protein profile of kappa expressing to lambda expressing B cells from the same healthy adult human. Lambda expressing B cells have more extensive antibody light chain gene rearrangements and may be selectively enriched for factors that promote light chain receptor editing. To quantify the proteins in kappa and lambda B cells, CD19+ B cells from peripheral blood were sorted for expression of kappa vs. lambda light chains. The fractions obtained were more than 95% pure (FIG. 17).

B cells were separated from human peripheral blood based on forward vs. side scatter into lymphocytes. Dead cells were excluded by staining with DAPI. Cells of interest were enriched for singlet events based upon pulse width gating. CD19+ staining cells were separated on the basis of kappa vs. lambda light chain expression. The kappa sorted cells are shown in the purity checks for this representative FIG. 17.

Next, the kappa vs. lambda B cells were analyzed by mass spectrometry. To quantify the kappa vs. lambda B cell proteome, kappa vs, lambda sorted B cells were mixed with a mixture of three different labeled human B cell lines. The three lymphocyte cells lines (CCL-120, CRL-2631, and TIB-196 from the ATCC) were metabolically labeled using 13C6 15N4 arginine and 12C6 lysine. The three cell lines were combined in a 1:1:1 cellular ratio and the equivalent of 0.5× 10e6 cells were added to each patient sample. The proteins were collected through a combination of direct lysis and TCA precipitation. The protein mixture was subjected to the FASP protocol, using SDS and 8M urea for denaturation followed by iodoacetamide treatment and trypsin digestion (Wiś-niewski et al., 2009 Nature Methods 6: 359-362). The peptides were eluted from the filter, washed and subjected to isoelectric focusing an Agilent 3100 Offgel fractionator. The resulting 12 fractions were cleaned using StageTips (Rappsilber et al., 2007 Nat Protoc. 2(8): 1896-906), separated by nanoflow HPLC on a 10 cm RP column at 300 nL/min over 90 minutes and then detected using an LTQ-Orbitrap. The results were processed with MaxQuant v1.013.8 and searched against the IPI Homo sapiens database (v. 3.52) using Mascot). The protein ratios (Heavy:Light) were inverted, then processed through a log 2 transformation, followed by 3 rounds of median centering by sample and protein. Approximately 1,000 protein identifications were obtained per cell population from two different donors.

The results were then rank ordered with respect to the proteins that were most expressed in the lambda B cells. Table 2 represents selected proteins of potential immunologic interest from one of the two donors. The ranking is from most expressed in lambda compared to kappa B cells. Thus a rank of 1 is highly expressed in lambda+ B cells whereas a rank of 1,000 is highly expressed in kappa+ B cells. It was observed that lambda constant region protein expression is ranked highly in lambda+ cells, whereas kappa constant region protein expression is near the bottom of the list, indicating that it is expressed more abundantly in kappa+ B cells.

Interestingly, IRF4 was ranked highly expressed in lambda+ B cells. Lambda+ B cells are more highly edited and have higher levels of RS rearrangement than kappa B cells. IRF4 is a transcription factor and is involved in controlling light chain gene rearrangement and may represent a therapeutic target for influencing receptor editing. Additional proteins on this list and identified by the larger experiment (results not presented), are potential receptor editing targets.

TABLE 2

Proteins that are expressed more highly in lambda+ than kappa+ B cells

| Rank | Description |
| --- | --- |
| 3 | IRF4 |
| 10 | lambda constant region |
| 26 | serine threonine phosphatase 2A |
| 92 | STAT3 |
| 100 | HLA class I, Cw |
| 103 | proteosome-associated protein ECM29 homolog |
| 174 | proteosome subunit alpha type-7 |
| 207 | complement C1q binding protein |
| 217 | interferon-induced GTP binding protein Mx1 |
| 218 | proteosome subunit beta type-8 |
| 240 | CD44 |
| 241 | gamma IFN inducibe protein Ifi-16 |
| 243 | galectin 1 |
| 253 | 26S proteosome non-ATPase regulatory subunit 1 |
| 260 | proteosome subunit alpha type-1 |
| 271 | HLA-DQ |
| 274 | HLA-DR invariant chain, similar to CD74 |
| 276 | 26S proteosome non-ATPase regulatory subunit 2 |
| 293 | proteosome subunit alpha type-6 |
| 305 | MHC class I |
| 310 | tyrosine protein kinase CSK; C-SRC |
| 311 | proteosome 26S subunit ATPase-6 |
| 864 | proteosome subunit beta type-2 |
| 868 | calnexin |
| 879 | Ig kappa |
| 995 | 26S proteosome ATPase-5 |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of diagnosing an autoimmune disease in a mammal, the method comprising obtaining DNA from a blood sample obtained from the mammal; measuring the frequency of recombination sequence (RS) rearrangement in the DNA obtained from the mammal; and calibrating the measured frequency of RS rearrangement by at least one of B cell fraction and κ/λ ratio in the blood sample, wherein a reduced level of RS rearrangement compared to the level of RS rearrangement in an otherwise identical healthy mammal is an indication that said mammal has an autoimmune disease.

2. The method of claim 1, wherein the reduced level of RS rearrangement confers an increased risk of the future development of autoimmunity.

3. The method of claim 1, wherein said autoimmune disease is type 1 diabetes.

4. The method of claim 1, wherein said autoimmune disease is systemic lupus erythematosus (SLE).

5. The method of claim 1, wherein said mammal is a human.

6. The method of claim 1, wherein said RS rearrangement is measured based on quantitative PCR.

7. A method of diagnosing an autoimmune disease in a mammal, the method comprising obtaining DNA from a blood sample obtained from the mammal; measuring the frequency of recombination sequence (RS) rearrangement in the DNA obtained from the mammal; and calibrating the measured frequency of RS rearrangement by at least one of B cell fraction and κ/λ ratio in the blood sample, without the use of flow cytometry, wherein a reduced level of RS rearrangement compared to the level of RS rearrangement in an otherwise identical healthy mammal is an indication that said mammal has an autoimmune disease.

* * * * *